United States Patent
Popow et al.

(10) Patent No.: US 9,340,779 B2
(45) Date of Patent: May 17, 2016

(54) USE OF A HSPC117 MOLECULE AS RNA LIGASE

(75) Inventors: Johannes Popow, Vienna (AT); Stefan Weitzer, Vienna (AT); Javier Martinez, Vienna (AT); Karl Mechtler, Landendorf (AT); Alexander Schleiffer, Vienna (AT)

(73) Assignee: IMBA—INSTITUT FÜR MOLEKULARE BIOTECHNOLOGIE GMBH, Vienna (AT)

( * ) Notice: Subject to any disclaimer, the term of this patent is extended or adjusted under 35 U.S.C. 154(b) by 237 days.

(21) Appl. No.: 13/814,854

(22) PCT Filed: Aug. 30, 2011

(86) PCT No.: PCT/EP2011/064884
§ 371 (c)(1),
(2), (4) Date: Feb. 7, 2013

(87) PCT Pub. No.: WO2012/028606
PCT Pub. Date: Mar. 8, 2012

(65) Prior Publication Data
US 2013/0156748 A1 Jun. 20, 2013

(30) Foreign Application Priority Data
Aug. 30, 2010 (EP) ..................... 10174549

(51) Int. Cl.
*C12N 9/00* (2006.01)
*C12Q 1/68* (2006.01)

(52) U.S. Cl.
CPC ... *C12N 9/93* (2013.01); *C12Q 1/68* (2013.01)

(58) Field of Classification Search
None
See application file for complete search history.

(56) References Cited

U.S. PATENT DOCUMENTS

| 9,074,203 B2 * | 7/2015 | Zeiner | C12N 9/93 |
| 2007/0204352 A1 | 8/2007 | Caldwell et al. | |
| 2013/0280763 A1 * | 10/2013 | Popow | C07K 14/4705 435/91.3 |

FOREIGN PATENT DOCUMENTS

| JP | 2008531019 | 8/2008 |
| WO | 2004/087884 A2 | 10/2004 |
| WO | 2006091964 | 8/2006 |

OTHER PUBLICATIONS

Hirokawa, Nobutaka "mRNA Transport in Dendrites: RNA Granules, Motors, and Tracks" The Journal of Neuroscience, Jul. 5, 2006, 26(27),pp. 7139-7142.*

Larsen, Delmar and Soderberg, Tim, "Phosphate diesters" UC Davis ChemWiki, §10.4, <URL:http://chemwiki.ucdavis.edu/Organic_Chemistry/Organic_Chemistry_With_a_Biological_Emphasis/Chapter_10%3A_Phosphoryl_transfer_reactions/Section_10.4%3A_Phosphate_diesters>, archived Sep. 15, 2011 (accessed online Dec. 15, 2015), 6 pages.*

Ambion , "KinaseMax™ Kit", Protocol Brochure, P/N. 1520M (Revision B), Jul. 18, 2008, pp. 1-18.*

Terpe, K. "Overview of tag protein fusions:from molecular and biochemical fundamentals to commercial systems" Appl Microbiol Biotechnol, 2003 (published online Nov. 7, 2002),60, pp. 523-533, DOI 10.1007/s00253-002-1158-6.*

Porecha, R. and Herschlag, D. "RNA Radiolabeling", Methods in Enzymology, 2013, vol. 530, chapter 14, pp. 255-279, DOI: 10.1016/B978-0-12-420037-1.00014-2.*

Englert, M; Sheppard, K; Aslanian, A; Yates, III, JR; Sölla, D"Archaeal 3'-phosphate RNA splicing ligase characterization identifies the missing component in tRNA maturation", PNAS, 2011, 108(4), pp. 1290-1295 and si pp. s1-s2 (doi: 10.1073/pnas.1018307108.*

Nabile Bouzaidi-Tiali et al., "Elongation factor 1a mediates the specificity of mitochondrial tRNA import in *T. brucei*", The EMBO Journal, 2007, pp. 4302-4312, vol. 26.

Patricia P. Chan et al., "GtRNAdb: a database of transfer RNA genes detected in genomic sequence", Nucleic Acids Research, 2009, D93-D97, vol. 37, Database Issue, (published online Nov. 4, 2008).

Victoria Drewett et al., "DNA-bound transcription factor complexes analysed by mass-spectrometry: binding of novel proteins to the human c-fos SRE and related sequences", Nucleic Acids Research, 2001, pp. 479-487, vol. 29, No. 2.

Markus Englert, "Mechanisms des pre-tRNA Spleißens Struktur und Funktion pflanzlicher und animaler RNA Ligasen", In PhD thesis, Faculty of Chemistry and Pharmaceutics (Würzburg, Bayerische Julius-Maximilians-Universität), pp. 139, 2005.

Michael Y. Galperin et al., "'Conserved hypothetical' proteins: prioritization of targets for experimental study", Nucleic Acids Research, 2004, pp. 5452-5463, vol. 32, No. 18.

Pascal Genschik et al., "Characterization of the *Escherichia coli* RNA 3'-Terminal Phosphate Cyclase and Its $\sigma^{54}$-Regulated Operon", The Journal of Biological Chemistry, 1998, pp. 22516-22526, vol. 273, No. 39.

John Abelson et al., "tRNA Splicing", The Journal of Biological Chemistry, 1998, pp. 12685-12688, vol. 273, No. 21.

Witold Filipowicz et al., "Origin of Splice Junction Phosphate in tRNAs Processed by HeLa Cell Extract", Cell, 1983, pp. 547-557, vol. 32.

Frank A. Laski et al., "Characterization of tRNA Precursor Splicing in Mammalian Extracts", The Journal of Biological Chemistry, 1983, pp. 11974-11980, vol. 258, No. 19.

Miyuki Kato et al., "Crystal Structure of the 2'-5' RNA Ligase from *Thermus thermophilus* HB8", Journal of Molecular Biology, Jun. 2003, pp. 903-911, vol. 329, No. 5, XP004457717.

Chiaki Okada et al., "Crystal Structure of an RtcB Homolog Protein (PH1602-Extein Protein) From *Pyrococcus horikoshii* Reveals a Novel Fold", Proteins: Structure, Function, and Bioinformatics, 2006, pp. 1119-1122, vol. 63, No. 1, XP-002628803.

(Continued)

*Primary Examiner* — Thane Underdahl
*Assistant Examiner* — Aaron J Kosar
(74) *Attorney, Agent, or Firm* — Sughrue Mion, PLLC

(57) ABSTRACT

The present invention relates to the use of HSPC117 molecules as RNA ligase, methods of ligating RNA molecules, kits for these methods and uses and transgenic cells.

15 Claims, 26 Drawing Sheets

(56) References Cited

OTHER PUBLICATIONS

John M. Pascal, "DNA and RNA ligases: structural variations and shared mechanisms", Current Opinion in Structural Biology, Feb. 2008, pp. 96-105, vol. 18, No. 1, XP022485997.

Johannes Popow et al., "HSPC117 is the Essential Subunit of a Human tRNA Splicing Ligase Complex", Science, Feb. 2011, pp. 760-764, vol. 331, No. 6018, XP007917547.

Li Kai Wang et al., "Structure-function analysis of yeast tRNA ligase", RNA, 2005, pp. 966-975, vol. 11, No. 6, XP002628775.

Carl E. Reid et al., "A host-specific function is required for ligation of a wide variety of ribozyme-processed RNAs", PNAS, Jan. 2000, pp. 424-429, vol. 97, No. 1.

International Search Report for PCT/EP2011/064884 dated Dec. 28, 2011, 5 pages.

* cited by examiner

SEQUENCE LISTING

<160> NUMBER OF SEQ ID NOS: 23

<210> SEQ ID NO 1
<211> LENGTH: 505
<212> TYPE: PRT
<213> ORGANISM: Homo sapiens

<400> SEQUENCE: 1

Met Ser Arg Ser Tyr Asn Asp Glu Leu Gln Phe Leu Glu Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Ala Arg Ala Lys Lys Arg Gly Leu Pro Gln Leu Gly Thr Leu Gly Ala
210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Phe Asp Leu His Val Ile Tyr Asp Val Ser
            340                 345                 350

His Asn Ile Ala Lys Val Glu Gln His Val Val Asp Gly Lys Glu Arg
        355                 360                 365

```
Thr Leu Leu Val His Arg Lys Gly Ser Thr Arg Ala Phe Pro Pro His
    370                 375                 380

His Pro Leu Ile Ala Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Met Gly Ile Ala Ile Arg Val Ala Ser Pro
450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
                500                 505

<210> SEQ ID NO 2
<211> LENGTH: 505
<212> TYPE: PRT
<213> ORGANISM: Mus musculus

<400> SEQUENCE: 2

Met Ser Arg Asn Tyr Asn Asp Glu Leu Gln Phe Leu Asp Lys Ile Asn
1               5                   10                  15

Lys Asn Cys Trp Arg Ile Lys Lys Gly Phe Val Pro Asn Met Gln Val
                20                  25                  30

Glu Gly Val Phe Tyr Val Asn Asp Ala Leu Glu Lys Leu Met Phe Glu
            35                  40                  45

Glu Leu Arg Asn Ala Cys Arg Gly Gly Val Gly Gly Phe Leu Pro
        50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
                100                 105                 110

Pro Gly Gly Val Gly Phe Asp Ile Asn Cys Gly Val Arg Leu Leu Arg
            115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Pro Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240
```

```
Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
        260                 265                 270

Ala Leu Val Ala Met Glu Lys Ala Met Lys Arg Asp Lys Ile Ile Val
            275                 280                 285

Asn Asp Arg Gln Leu Ala Cys Ala Arg Ile Ala Ser Pro Glu Gly Gln
290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Leu Asp Leu His Val Ile Tyr Asp Val Ser
            340                 345                 350

His Asn Ile Ala Lys Val Glu Gln His Val Val Asp Gly Lys Glu Arg
        355                 360                 365

Thr Leu Leu Val His Arg Lys Gly Ser Thr Arg Ala Phe Pro Pro His
    370                 375                 380

His Pro Leu Ile Ala Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
        435                 440                 445

Leu Asp Lys Leu Ala Asp Met Gly Ile Ala Ile Arg Val Ala Ser Pro
    450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
            500                 505

<210> SEQ ID NO 3
<211> LENGTH: 505
<212> TYPE: PRT
<213> ORGANISM: Xenopus laevis

<400> SEQUENCE: 3

Met Ser Arg Ser Tyr Asn Asp Glu Leu Gln Tyr Leu Asp Lys Ile His
1               5                   10                  15

Asn Asn Cys Trp Arg Ile Arg Lys Gly Phe Val Pro Asn Met Gln Val
                20                  25                  30

Glu Gly Val Phe Tyr Val Asn Asp Pro Leu Glu Lys Leu Met Phe Glu
            35                  40                  45

Glu Leu Arg Asn Ala Ser Arg Gly Ala Ala Gly Gly Phe Leu Pro
        50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Glu Asn Pro Asp Ala Val Val Ser
            100                 105                 110
```

Pro Gly Gly Val Gly Phe Asp Ile Asn Cys Gly Val Arg Leu Leu Arg
            115                 120                 125

Thr Asn Leu Asp Glu Ser Asp Val Gln Pro Val Lys Glu Gln Leu Ala
130                 135                 140

Gln Ser Met Phe Asp His Ile Pro Val Gly Val Gly Ser Lys Gly Val
145                 150                 155                 160

Ile Pro Met Gly Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
                180                 185                 190

Cys Glu Glu Tyr Gly Arg Met Leu Gln Ala Asp Pro Ser Lys Val Ser
                195                 200                 205

Ser Lys Ala Lys Lys Arg Gly Leu Pro Gln Leu Gly Thr Leu Gly Ala
210                 215                 220

Gly Asn His Tyr Ala Glu Val Gln Val Val Asp Glu Ile Tyr Asp Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
                260                 265                 270

Ala Leu Val Ala Met Glu Lys Ala Met Lys Arg Asp Lys Ile Thr Val
                275                 280                 285

Asn Asp Arg Gln Leu Ala Cys Ala Arg Ile Ser Ser Asp Glu Gly Gln
                290                 295                 300

Asp Tyr Leu Lys Gly Met Ala Ala Ala Gly Asn Tyr Ala Trp Val Asn
305                 310                 315                 320

Arg Ser Ser Met Thr Phe Leu Thr Arg Gln Ala Phe Ser Lys Val Phe
                325                 330                 335

Asn Thr Pro Pro Asp Asp Leu Asp Met His Val Ile Tyr Asp Val Ser
                340                 345                 350

His Asn Ile Ala Lys Val Glu Gln His Val Val Glu Gly Lys Glu Met
                355                 360                 365

Thr Leu Leu Val His Arg Lys Gly Ala Thr Arg Ala Phe Pro Pro His
                370                 375                 380

His Pro Leu Ile Pro Val Asp Tyr Gln Leu Thr Gly Gln Pro Val Leu
385                 390                 395                 400

Ile Gly Gly Thr Met Gly Thr Cys Ser Tyr Val Leu Thr Gly Thr Asp
                405                 410                 415

Gln Gly Met Thr Glu Thr Phe Gly Thr Thr Cys His Gly Ala Gly Arg
                420                 425                 430

Ala Leu Ser Arg Ala Lys Ser Arg Arg Asn Leu Asp Phe Gln Asp Val
                435                 440                 445

Leu Asp Lys Leu Ala Asp Leu Gly Ile Ala Ile Arg Val Ala Ser Pro
450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
                500                 505

<210> SEQ ID NO 4
<211> LENGTH: 508

<212> TYPE: PRT
<213> ORGANISM: Strongylocentrotus purpuratus

<400> SEQUENCE: 4

```
Met Ala Ala Thr Val Arg Glu Tyr Lys Glu Glu Leu Lys Tyr Leu Asn
1               5                  10                  15

Lys Leu Ser Asp Asn Cys Trp Gln Ile Lys Lys Gly Phe Val Asp Asn
            20                  25                  30

Met Lys Val Glu Gly Arg Phe Tyr Val Asp Ser Lys Leu Glu Lys Leu
        35                  40                  45

Met Phe Glu Glu Leu Gln Gln Ala Cys Arg Ser Lys Gly Val Gly Gly
    50                  55                  60

Phe Leu Pro Ala Val Lys Gln Ile Ala Asn Val Ala Ala Leu Pro Gly
65                  70                  75                  80

Ile Thr Gly Tyr Ser Ile Gly Leu Pro Asp Ile His Ser Gly Tyr Gly
                85                  90                  95

Phe Ala Ile Gly Asn Met Ala Ala Phe Asp Met Ser Asn Pro Glu Ala
            100                 105                 110

Val Val Ser Pro Gly Gly Val Gly Phe Asp Ile Asn Cys Gly Val Arg
        115                 120                 125

Leu Leu Arg Thr Asn Leu Thr Glu Lys Asp Val Lys Pro Val Lys Glu
130                 135                 140

Gln Leu Ala Gln Ser Leu Phe Asp His Ile Pro Val Gly Val Gly Ser
145                 150                 155                 160

Lys Gly Val Ile Pro Met Gly Ala Lys Glu Leu Glu Glu Ala Leu Glu
                165                 170                 175

Met Gly Met Asp Trp Ser Leu Arg Glu Gly Tyr Ala Trp Ala Glu Asp
            180                 185                 190

Lys Glu His Cys Glu Glu Tyr Gly Arg Met Leu Gln Ala Asp Pro Asn
        195                 200                 205

Lys Val Ser Ala Arg Ala Lys Lys Arg Gly Leu Pro Gln Leu Gly Thr
210                 215                 220

Leu Gly Ala Gly Asn His Tyr Ala Glu Ile Gln Val Val Asp Glu Ile
225                 230                 235                 240

Tyr Asn Asp His Ala Ala Lys Lys Met Gly Ile Asp Arg Lys Gly Gln
                245                 250                 255

Val Cys Leu Met Ile His Ser Gly Ser Arg Gly Leu Gly His Gln Val
            260                 265                 270

Ala Thr Asp Ala Leu Val Gln Met Glu Lys Ala Met Lys Arg Asp Lys
        275                 280                 285

Ile Glu Val Asn Asp Arg Gln Leu Ala Cys Ala Arg Ile His Ser Gln
290                 295                 300

Glu Gly Gln Asp Tyr Leu Lys Ala Met Ala Ala Ala Asn Tyr Ala
305                 310                 315                 320

Trp Val Asn Arg Ser Ser Met Thr Phe Leu Thr Arg Gln Ala Phe Ala
                325                 330                 335

Lys Gln Phe Asp Thr Thr Pro Asp Asp Leu Asp Met His Val Ile Tyr
            340                 345                 350

Asp Val Ser His Asn Ile Ala Lys Val Glu Glu His Met Val Asp Gly
        355                 360                 365

Val Gln Lys Thr Leu Leu Val His Arg Lys Gly Ser Thr Arg Ala Phe
370                 375                 380

Pro Pro His His Pro Leu Ile Pro Val Asp Tyr Gln Met Thr Gly Gln
385                 390                 395                 400
```

```
Pro Val Leu Ile Gly Gly Thr Met Gly Thr Cys Ser Tyr Val Leu Thr
                405                 410                 415

Gly Thr Glu Ser Gly Met Ala Thr Thr Tyr Gly Thr Thr Cys His Gly
            420                 425                 430

Ala Gly Arg Ala Trp Ser Arg Ala Lys Ser Arg Arg Asn Leu Asp Tyr
            435                 440                 445

Gln Thr Val Leu Lys Asn Leu His Glu Leu Gly Ile Ser Ile Arg Val
450                 455                 460

Ala Ser Pro Lys Leu Val Met Glu Glu Ala Pro Glu Ser Tyr Lys Asp
465                 470                 475                 480

Val Thr Ser Val Val Asn Thr Cys His Asp Val Gly Ile Ser Lys Lys
                485                 490                 495

Val Leu Lys Leu Arg Pro Ile Ala Val Ile Lys Gly
                500                 505

<210> SEQ ID NO 5
<211> LENGTH: 506
<212> TYPE: PRT
<213> ORGANISM: Drosophila melanogaster

<400> SEQUENCE: 5

Met Val Val Arg Pro Tyr Asn Asp Glu Leu Arg Tyr Leu Glu Lys Val
1               5                   10                  15

Ser Asp His Cys Trp Arg Ile Lys Lys Gly Phe Gln Pro Asn Met Asn
                20                  25                  30

Val Glu Gly Cys Phe Tyr Val Asn Ser Arg Leu Glu Arg Leu Met Leu
            35                  40                  45

Glu Glu Leu Lys Asn Ser Cys Arg Pro Gly Ala Val Gly Gly Phe Leu
50                  55                  60

Pro Gly Val Lys Gln Ile Ala Asn Val Ala Ala Leu Pro Gly Ile Val
65                  70                  75                  80

Gly Arg Ser Ile Gly Leu Pro Asp Ile His Ser Gly Tyr Gly Phe Ala
                85                  90                  95

Ile Gly Asn Met Ala Ala Phe Asp Met Asn Asp Pro Leu Ser Val Val
            100                 105                 110

Ser Pro Gly Gly Val Gly Phe Asp Ile Asn Cys Gly Val Arg Leu Leu
        115                 120                 125

Arg Thr Asn Leu Tyr Glu Lys Asp Val Gln Pro Val Lys Glu Gln Leu
130                 135                 140

Ala Gln Ser Leu Phe Asp His Ile Pro Val Gly Val Gly Ser Lys Gly
145                 150                 155                 160

Ile Ile Pro Met Asn Ala Arg Asp Leu Glu Glu Ala Leu Glu Met Gly
                165                 170                 175

Met Asp Trp Ser Leu Arg Glu Gly Tyr Val Trp Ala Glu Asp Lys Glu
            180                 185                 190

His Cys Glu Glu Tyr Gly Arg Met Leu Asn Ala Asp Pro Ala Lys Val
        195                 200                 205

Ser Met Arg Ala Lys Lys Arg Gly Leu Pro Gln Leu Gly Thr Leu Gly
210                 215                 220

Ala Gly Asn His Tyr Ala Glu Ile Gln Val Val Asp Glu Ile Tyr Asp
225                 230                 235                 240

Lys Trp Ser Ala Ser Lys Met Gly Ile Glu Glu Lys Gly Gln Val Val
                245                 250                 255

Val Met Ile His Ser Gly Ser Arg Gly Phe Gly His Gln Val Ala Thr
```

```
            260                 265                 270
Asp Ala Leu Val Gln Met Glu Lys Ala Met Lys Arg Asp Lys Ile Glu
            275                 280                 285

Thr Asn Asp Arg Gln Leu Ala Cys Ala Arg Ile Asn Ser Val Glu Gly
            290                 295                 300

Gln Asp Tyr Leu Lys Ala Met Ala Ala Ala Asn Phe Ala Trp Val
305                 310                 315                 320

Asn Arg Ser Ser Met Thr Phe Leu Thr Arg Gln Ala Phe Ala Lys Met
                325                 330                 335

Phe Asn Thr Thr Pro Asp Asp Leu Asp Met His Val Ile Tyr Asp Val
                340                 345                 350

Ser His Asn Ile Ala Lys Val Glu Asn His Met Val Asp Gly Lys Glu
            355                 360                 365

Arg Lys Leu Leu Val His Arg Lys Gly Ser Thr Arg Ala Phe Pro Pro
            370                 375                 380

His His Pro Leu Ile Pro Val Asp Tyr Gln Leu Thr Gly Gln Pro Val
385                 390                 395                 400

Leu Val Gly Gly Thr Met Gly Thr Cys Ser Tyr Val Leu Thr Gly Thr
                405                 410                 415

Glu Gln Gly Met Gln Glu Thr Phe Gly Ser Thr Cys His Gly Ala Gly
                420                 425                 430

Arg Ala Leu Ser Arg Ala Lys Ser Arg Arg Asn Leu Asp Tyr Lys Asp
            435                 440                 445

Val Leu Asp Lys Leu Asp Gln Leu Gly Ile Ala Ile Arg Val Ala Ser
            450                 455                 460

Pro Lys Leu Val Met Glu Glu Ala Pro Glu Ser Tyr Lys Asp Val Thr
465                 470                 475                 480

Asp Val Val Asp Thr Cys His Ala Gly Ile Ser Lys Lys Cys Ile
                485                 490                 495

Lys Met Arg Pro Ile Ala Val Ile Lys Gly
                500                 505

<210> SEQ ID NO 6
<211> LENGTH: 505
<212> TYPE: PRT
<213> ORGANISM: Caenorhabditis elegans

<400> SEQUENCE: 6

Met Pro Arg Thr Phe Glu Glu Cys Asp Phe Ile Asp Arg Leu Thr
1               5                   10                  15

Asp Thr Lys Phe Arg Ile Lys Lys Gly Phe Val Pro Asn Met Asn Val
                20                  25                  30

Glu Gly Arg Phe Tyr Val Asn Asn Ser Leu Glu Gln Leu Met Phe Asp
            35                  40                  45

Glu Leu Lys Phe Ser Cys Asp Gly Gln Gly Ile Gly Gly Phe Leu Pro
50                  55                  60

Ala Val Arg Gln Ile Ala Asn Val Ala Ser Leu Pro Gly Ile Val Gly
65                  70                  75                  80

His Ser Ile Gly Leu Pro Asp Ile His Ser Gly Tyr Gly Phe Ser Ile
                85                  90                  95

Gly Asn Ile Ala Ala Phe Asp Val Gly Asn Pro Glu Ser Val Ile Ser
            100                 105                 110

Pro Gly Gly Val Gly Phe Asp Ile Asn Cys Gly Val Arg Leu Leu Arg
            115                 120                 125
```

```
Thr Asn Leu Phe Glu Glu Asn Val Lys Pro Leu Lys Glu Gln Leu Thr
        130                 135                 140

Gln Ser Leu Phe Asp His Ile Pro Val Gly Val Gly Ser Arg Gly Ala
145                 150                 155                 160

Ile Pro Met Leu Ala Ser Asp Leu Val Glu Cys Leu Glu Met Gly Met
                165                 170                 175

Asp Trp Thr Leu Arg Glu Gly Tyr Ser Trp Ala Glu Asp Lys Glu His
            180                 185                 190

Cys Glu Glu Tyr Gly Arg Met Leu Gln Ala Asp Ala Ser Lys Val Ser
        195                 200                 205

Leu Arg Ala Lys Lys Arg Gly Leu Pro Gln Leu Gly Thr Leu Gly Ala
210                 215                 220

Gly Asn His Tyr Ala Glu Val Gln Val Val Asp Glu Ile Tyr Asp Lys
225                 230                 235                 240

His Ala Ala Ser Thr Met Gly Ile Asp Glu Gly Gln Val Val Val
                245                 250                 255

Met Leu His Cys Gly Ser Arg Gly Leu Gly His Gln Val Ala Thr Asp
                260                 265                 270

Ser Leu Val Glu Met Glu Lys Ala Met Ala Arg Asp Gly Ile Val Val
        275                 280                 285

Asn Asp Lys Gln Leu Ala Cys Ala Arg Ile Asn Ser Val Glu Gly Lys
290                 295                 300

Asn Tyr Phe Ser Gly Met Ala Ala Ala Asn Phe Ala Trp Val Asn
305                 310                 315                 320

Arg Ser Cys Ile Thr Phe Cys Val Arg Asn Ala Phe Gln Lys Thr Phe
                325                 330                 335

Gly Met Ser Ala Asp Asp Met Asp Met Gln Val Ile Tyr Asp Val Ser
            340                 345                 350

His Asn Val Ala Lys Met Glu Glu His Met Val Asp Gly Arg Pro Arg
        355                 360                 365

Gln Leu Cys Val His Arg Lys Gly Ala Thr Arg Ala Phe Pro Ala His
        370                 375                 380

His Pro Leu Ile Pro Val Asp Tyr Gln Leu Ile Gly Gln Pro Val Leu
385                 390                 395                 400

Ile Gly Gly Ser Met Gly Thr Cys Ser Tyr Val Leu Thr Gly Thr Glu
                405                 410                 415

Gln Gly Leu Val Glu Thr Phe Gly Thr Thr Cys His Gly Ala Gly Arg
            420                 425                 430

Ala Leu Ser Arg Ala Lys Ser Arg Arg Thr Ile Thr Trp Asp Ser Val
        435                 440                 445

Ile Asp Asp Leu Lys Lys Lys Glu Ile Ser Ile Arg Ile Ala Ser Pro
450                 455                 460

Lys Leu Ile Met Glu Glu Ala Pro Glu Ser Tyr Lys Asn Val Thr Asp
465                 470                 475                 480

Val Val Asp Thr Cys Asp Ala Ala Gly Ile Ser Lys Lys Ala Val Lys
                485                 490                 495

Leu Arg Pro Ile Ala Val Ile Lys Gly
                500                 505

<210> SEQ ID NO 7
<211> LENGTH: 476
<212> TYPE: PRT
<213> ORGANISM: Chlamydomonas reinhardtii

<400> SEQUENCE: 7
```

-continued

```
Met His Val Pro Gly Thr Phe Tyr Val Asn Asp Ala Leu Lys Gly Leu
1               5                   10                  15

Leu Phe Glu Glu Leu Gln Gln Ala Val Val Arg Gly Asp His Gly Gly
                20                  25                  30

Phe Leu Pro Ala Val Lys Gln Leu Ala Asn Val Ala Ala Leu Pro Gly
            35                  40                  45

Ile Val Lys Arg Ser Ile Ala Leu Pro Asp Val His Ser Gly Tyr Gly
    50                  55                  60

Phe Ala Ile Gly Asn Val Ala Ala Phe Asp Met Asp Asn Pro Glu Ala
65              70                  75                  80

Val Val Ser Pro Gly Gly Val Gly Phe Asp Ile Asn Cys Gly Val Arg
                85                  90                  95

Leu Leu Arg Thr Asn Leu Thr Glu Ala Glu Val Gly Pro Val Arg Glu
                100                 105                 110

Gln Leu Ala Gln Ala Leu Phe Asp His Ile Pro Val Gly Val Gly Ser
            115                 120                 125

Gln Gly Ile Ile Pro Thr Thr Ala Lys Asp Met Glu Ser Ala Leu Glu
130                 135                 140

Leu Gly Met Asp Trp Ser Leu Arg Glu Gly Tyr Ala Trp Ala Glu Asp
145                 150                 155                 160

Lys Glu His Cys Glu Glu Tyr Gly Arg Met Leu Asn Ala Asp Pro Arg
                165                 170                 175

Tyr Val Ser Ser Arg Ala Lys Lys Arg Gly Leu Pro Gln Met Gly Thr
            180                 185                 190

Leu Gly Ala Gly Asn His Tyr Ala Glu Val Gln Val Val Asp Glu Val
            195                 200                 205

Tyr Asp Ala Val Ala Ala Arg Arg Met Gly Ile Asp Thr Pro Gly Gln
210                 215                 220

Val Val Val Met Ile His Ser Gly Ser Arg Gly Leu Gly His Gln Val
225                 230                 235                 240

Ala Thr Asp Ala Leu Val Ala Met Glu Arg Ala Met Ala Arg Asp Gly
            245                 250                 255

Ile Ile Thr Asn Asp Arg Gln Leu Ala Cys Ala Arg Ile Asn Ser Glu
            260                 265                 270

Glu Gly Gln Ala Tyr Leu Lys Ala Met Ser Cys Ala Ala Asn Tyr Ala
            275                 280                 285

Trp Val Asn Arg Ser Ser Met Thr Phe Leu Ala Arg Gln Ala Phe Ala
            290                 295                 300

Lys Ile Phe Lys Ser Thr Pro Asp Asp Leu Asp Met His Val Val Tyr
305                 310                 315                 320

Asp Val Ser His Asn Ile Ala Lys Val Glu Gln His Cys Val Asp Gly
            325                 330                 335

Gln His Arg Arg Leu Leu Val His Arg Lys Gly Ser Thr Arg Ala Phe
            340                 345                 350

Pro Pro His His Pro Leu Ile Pro Ala Asp Tyr Gln Leu Ile Gly Gln
            355                 360                 365

Pro Val Leu Val Gly Gly Thr Met Gly Thr Ser Ser Tyr Val Leu Thr
370                 375                 380

Gly Thr Glu Gln Gly Phe Thr Glu Thr Phe Gly Ser Thr Cys His Gly
385                 390                 395                 400

Ala Gly Arg Ala Arg Ser Arg Asn Asn Ser Arg Asn Lys Leu Asp Tyr
                405                 410                 415
```

```
Gln Asp Val Leu Asp Asn Leu Lys Ala Lys Gly Ile Ala Ile Arg Val
            420                 425                 430

Ala Ser Pro Lys Leu Val Met Glu Glu Ala Pro Glu Ser Tyr Lys Asp
        435                 440                 445

Val Ser Glu Val Val Asp Thr Cys His Gln Ala Gly Ile Ser Lys Lys
450                 455                 460

Ala Val Lys Leu Arg Pro Ile Ala Val Ile Lys Gly
465                 470                 475

<210> SEQ ID NO 8
<211> LENGTH: 480
<212> TYPE: PRT
<213> ORGANISM: Methanococcus jannaschii

<400> SEQUENCE: 8

Met Lys Asp Val Leu Lys Arg Val Ser Asp Val Val Trp Glu Leu Pro
1               5                   10                  15

Lys Asp Tyr Lys Asp Cys Met Arg Val Pro Gly Arg Ile Tyr Leu Asn
            20                  25                  30

Glu Ile Leu Leu Asp Glu Leu Glu Pro Glu Val Leu Glu Gln Ile Ala
        35                  40                  45

Asn Val Ala Cys Leu Pro Gly Ile Tyr Lys Tyr Ser Ile Ala Met Pro
50                  55                  60

Asp Val His Tyr Gly Tyr Gly Phe Ala Ile Gly Gly Val Ala Ala Phe
65                  70                  75                  80

Asp Gln Arg Glu Gly Val Ile Ser Pro Gly Gly Val Gly Phe Asp Ile
            85                  90                  95

Asn Cys Gly Val Arg Leu Ile Arg Thr Asn Leu Thr Lys Glu Glu Val
            100                 105                 110

Gln Ser Lys Ile Lys Glu Leu Ile Lys Thr Leu Phe Lys Asn Val Pro
        115                 120                 125

Ser Gly Leu Gly Ser Lys Gly Ile Leu Lys Phe Ser Lys Ser Val Met
130                 135                 140

Asp Asp Val Leu Glu Glu Gly Val Arg Trp Ala Val Lys Glu Gly Tyr
145                 150                 155                 160

Gly Trp Lys Glu Asp Leu Glu Phe Ile Glu Glu His Gly Cys Leu Lys
            165                 170                 175

Asp Ala Asp Ala Ser Tyr Val Ser Asp Lys Ala Lys Glu Arg Gly Arg
        180                 185                 190

Val Gln Leu Gly Ser Leu Gly Ser Gly Asn His Phe Leu Glu Val Gln
    195                 200                 205

Tyr Val Glu Lys Val Phe Asp Glu Glu Ala Ala Glu Ile Tyr Gly Ile
    210                 215                 220

Glu Glu Asn Gln Val Val Leu Val His Thr Gly Ser Arg Gly Leu
225                 230                 235                 240

Gly His Gln Ile Cys Thr Asp Tyr Leu Arg Ile Met Glu Lys Ala Ala
            245                 250                 255

Lys Asn Tyr Gly Ile Lys Leu Pro Asp Arg Gln Leu Ala Cys Ala Pro
        260                 265                 270

Phe Glu Ser Glu Glu Gly Gln Ser Tyr Phe Lys Ala Met Cys Cys Gly
    275                 280                 285

Ala Asn Tyr Ala Trp Ala Asn Arg Gln Met Ile Thr His Trp Val Arg
    290                 295                 300

Glu Ser Phe Glu Glu Val Phe Lys Ile His Ala Glu Asp Leu Glu Met
305                 310                 315                 320
```

```
Asn Ile Val Tyr Asp Val Ala His Asn Ile Ala Lys Lys Glu Glu His
                325                 330                 335

Ile Ile Asp Gly Arg Lys Val Lys Val Ile Val His Arg Lys Gly Ala
            340                 345                 350

Thr Arg Ala Phe Pro Pro Lys His Glu Ala Ile Pro Lys Glu Tyr Trp
        355                 360                 365

Ser Val Gly Gln Pro Val Ile Ile Pro Gly Asp Met Gly Thr Ala Ser
370                 375                 380

Tyr Leu Met Arg Gly Thr Glu Ile Ala Met Lys Glu Thr Phe Gly Ser
385                 390                 395                 400

Thr Ala His Gly Ala Gly Arg Lys Leu Ser Arg Ala Lys Ala Leu Lys
                405                 410                 415

Leu Trp Lys Gly Lys Glu Ile Gln Arg Arg Leu Ala Glu Met Gly Ile
            420                 425                 430

Val Ala Met Ser Asp Ser Lys Ala Val Met Glu Glu Ala Pro Glu
        435                 440                 445

Ala Tyr Lys Ser Val Asp Leu Val Ala Asp Thr Cys His Lys Ala Gly
        450                 455                 460

Ile Ser Leu Lys Val Ala Arg Met Arg Pro Leu Gly Val Ile Lys Gly
465                 470                 475                 480

<210> SEQ ID NO 9
<211> LENGTH: 481
<212> TYPE: PRT
<213> ORGANISM: Pyrococcus horikoshii

<400> SEQUENCE: 9

Met Val Val Pro Leu Lys Arg Ile Asp Lys Ile Arg Trp Glu Ile Pro
1               5                   10                  15

Lys Phe Asp Lys Arg Met Arg Val Pro Gly Arg Val Tyr Ala Asp Glu
            20                  25                  30

Val Leu Leu Glu Lys Met Lys Asn Asp Arg Thr Leu Glu Gln Ala Thr
        35                  40                  45

Asn Val Ala Met Leu Pro Gly Ile Tyr Lys Tyr Ser Ile Val Met Pro
50                  55                  60

Asp Gly His Gln Gly Tyr Gly Phe Pro Ile Gly Gly Val Ala Ala Phe
65                  70                  75                  80

Asp Val Lys Glu Gly Val Ile Ser Pro Gly Gly Ile Gly Tyr Asp Ile
            85                  90                  95

Asn Cys Gly Val Arg Leu Ile Arg Thr Asn Leu Thr Glu Lys Glu Val
            100                 105                 110

Arg Pro Arg Ile Lys Gln Leu Val Asp Thr Leu Phe Lys Asn Val Pro
        115                 120                 125

Ser Gly Val Gly Ser Gln Gly Arg Ile Lys Leu His Trp Thr Gln Ile
130                 135                 140

Asp Asp Val Leu Val Asp Gly Ala Lys Trp Ala Val Asp Asn Gly Tyr
145                 150                 155                 160

Gly Trp Glu Arg Asp Leu Glu Arg Leu Glu Glu Gly Gly Arg Met Glu
                165                 170                 175

Gly Ala Asp Pro Glu Ala Val Ser Gln Arg Ala Lys Gln Arg Gly Ala
            180                 185                 190

Pro Gln Leu Gly Ser Leu Gly Ser Gly Asn His Phe Leu Glu Val Gln
        195                 200                 205

Val Val Asp Lys Ile Phe Asp Pro Glu Val Ala Lys Ala Tyr Gly Leu
```

```
            210                 215                 220
Phe Glu Gly Gln Val Val Met Val His Thr Gly Ser Arg Gly Leu
225                 230                 235                 240

Gly His Gln Val Ala Ser Asp Tyr Leu Arg Ile Met Glu Arg Ala Ile
                    245                 250                 255

Arg Lys Tyr Arg Ile Pro Trp Pro Asp Arg Glu Leu Val Ser Val Pro
                260                 265                 270

Phe Gln Ser Glu Glu Gly Gln Arg Tyr Phe Ser Ala Met Lys Ala Ala
                275                 280                 285

Ala Asn Phe Ala Trp Ala Asn Arg Gln Met Ile Thr His Trp Val Arg
290                 295                 300

Glu Ser Phe Gln Glu Val Phe Lys Gln Asp Pro Glu Gly Asp Leu Gly
305                 310                 315                 320

Met Asp Ile Val Tyr Asp Val Ala His Asn Ile Gly Lys Val Glu Glu
                    325                 330                 335

His Glu Val Asp Gly Lys Arg Val Lys Val Ile Val His Arg Lys Gly
                340                 345                 350

Ala Thr Arg Ala Phe Pro Pro Gly His Glu Ala Val Pro Arg Leu Tyr
                355                 360                 365

Arg Asp Val Gly Gln Pro Val Leu Ile Pro Gly Ser Met Gly Thr Ala
370                 375                 380

Ser Tyr Ile Leu Ala Gly Thr Glu Gly Ala Met Lys Glu Thr Phe Gly
385                 390                 395                 400

Ser Thr Cys His Gly Ala Gly Arg Val Leu Ser Arg Lys Ala Ala Thr
                405                 410                 415

Arg Gln Tyr Arg Gly Asp Arg Ile Arg Gln Glu Leu Leu Asn Arg Gly
                420                 425                 430

Ile Tyr Val Arg Ala Ala Ser Met Arg Val Val Ala Glu Ala Pro
                435                 440                 445

Gly Ala Tyr Lys Asn Val Asp Asn Val Val Lys Val Val Ser Glu Ala
                450                 455                 460

Gly Ile Ala Lys Leu Val Ala Arg Met Arg Pro Ile Gly Val Ala Lys
465                 470                 475                 480

Gly
```

<210> SEQ ID NO 10
<211> LENGTH: 476
<212> TYPE: PRT
<213> ORGANISM: Thermus thermophilus

<400> SEQUENCE: 10

```
Met Phe Phe Glu Lys Ile Ala Pro Tyr Thr Tyr Arg Ile Pro Arg Gln
1               5                   10                  15

Gly Lys Met Arg Val Asp Ala Val Phe Phe Ala Ser Lys Glu Ile Leu
                20                  25                  30

Lys Asp Leu Glu Ala Glu Asn Tyr Ala Ser Leu Gln Gln Leu Met Asn
                35                  40                  45

Val Ala Thr Leu Pro Gly Ile Val Glu Pro Ala Leu Ala Met Pro Asp
                50                  55                  60

Ile His Trp Gly Tyr Gly Phe Pro Ile Gly Gly Val Ala Ala Phe Asp
65                  70                  75                  80

Pro Glu Glu Gly Val Val Ser Pro Gly Gly Val Gly Phe Asp Ile
                85                  90                  95

Asn Cys Gly Val Arg Leu Leu Ala Ser His Leu Thr Leu Glu Asp Leu
```

```
            100                 105                 110
Leu Pro Arg Gln Lys Glu Leu Ala Asp Ala Leu Tyr Arg Leu Val Pro
            115                 120                 125

Ser Gly Val Gly Ser Glu Arg Arg Asp Val Arg Phe Ser Lys Arg Glu
            130                 135             140

Leu Lys Glu Ile Leu Lys Glu Gly Ala Gly Trp Leu Val Lys Arg Gly
145                 150                 155                 160

Tyr Gly Tyr Pro Glu Asp Val Arg Phe Ile Glu Ser Gln Gly Arg Leu
                    165                 170                 175

Pro Trp Ala Asn Pro Asp Lys Val Ser Glu Arg Ala Phe Glu Arg Gly
                180                 185                 190

Ala Pro Gln Ile Gly Thr Leu Gly Ser Gly Asn His Phe Leu Glu Val
            195                 200                 205

Gln Tyr Val Asp Glu Val Tyr Asp Glu Glu Ala Leu Ala Phe Gly
            210                 215                 220

Leu Phe Lys Gly Gln Val Thr Val Leu Ile His Thr Gly Ser Arg Gly
225                 230                 235                 240

Leu Gly His Gln Val Cys Gln Asp Tyr Val Glu Arg Phe Leu Lys Val
                    245                 250                 255

Ala Pro Arg Tyr Gly Ile Glu Leu Val Asp Lys Gln Leu Ala Ala Ala
                260                 265                 270

Pro Ile Lys Ser Pro Glu Gly Gln Asp Tyr Leu Gln Ala Met Ala Ala
                275                 280                 285

Ala Ala Asn Phe Ala Phe Ala Asn Arg Gln Leu Ile Ala His Phe Val
            290                 295                 300

Arg Glu Ala Phe Glu Lys Val Gly Phe Thr Pro Arg Asp His Gly Leu
305                 310                 315                 320

Arg Val Leu Tyr Asp Leu Ala His Asn Asn Ala Lys Phe Glu Glu His
                    325                 330                 335

Arg Gly Arg Arg Val Leu Val His Arg Lys Gly Ala Thr Arg Ala Phe
                340                 345                 350

Gly Pro Gly His Pro Glu Val Pro Glu Glu Tyr Arg Arg Val Gly Gln
            355                 360                 365

Pro Val Leu Val Pro Gly Asp Met Gly Arg Tyr Ser Tyr Val Leu Ala
370                 375                 380

Gly Thr Glu Lys Ala Met Glu Val Ser Phe Gly Ser Ser Cys His Gly
385                 390                 395                 400

Ala Gly Arg Lys Met Ser Arg His Gln Ala Lys Lys Val Ala Arg Glu
                    405                 410                 415

Arg Asn Leu Val Lys Glu Leu Ala Glu Arg Gly Ile Leu Val Arg Ala
                420                 425                 430

Ala Thr Arg Ala Thr Val Asp Glu Met Pro Glu Ala Tyr Lys Asp
                435                 440                 445

Val Ser Leu Val Val Glu Ala Val Glu Gly Ala Gly Ile Gly Lys Lys
            450                 455                 460

Val Ala Arg Leu Arg Pro Leu Ile Val Val Lys Gly
465                 470                 475

<210> SEQ ID NO 11
<211> LENGTH: 408
<212> TYPE: PRT
<213> ORGANISM: Escherichia coli

<400> SEQUENCE: 11
```

```
Met Asn Tyr Glu Leu Leu Thr Thr Glu Asn Ala Pro Val Lys Met Trp
1               5                   10                  15
Thr Lys Gly Val Pro Val Glu Ala Asp Ala Arg Gln Gln Leu Ile Asn
            20                  25                  30
Thr Ala Lys Met Pro Phe Ile Phe Lys His Ile Ala Val Met Pro Asp
        35                  40                  45
Val His Leu Gly Lys Gly Ser Thr Ile Gly Ser Val Ile Pro Thr Lys
    50                  55                  60
Gly Ala Ile Ile Pro Ala Val Gly Val Asp Ile Gly Cys Gly Met
65                  70                  75                  80
Asn Ala Leu Arg Thr Ala Leu Thr Ala Glu Asp Leu Pro Glu Asn Leu
                85                  90                  95
Ala Glu Leu Arg Gln Ala Ile Glu Thr Ala Val Pro His Gly Arg Thr
            100                 105                 110
Thr Gly Arg Cys Lys Arg Asp Lys Gly Ala Trp Glu Asn Pro Pro Val
        115                 120                 125
Asn Val Asp Ala Lys Trp Ala Glu Leu Glu Ala Gly Tyr Gln Trp Leu
    130                 135                 140
Thr Gln Lys Tyr Pro Arg Phe Leu Asn Thr Asn Asn Tyr Lys His Leu
145                 150                 155                 160
Gly Thr Leu Gly Thr Gly Asn His Phe Ile Glu Ile Cys Leu Asp Glu
                165                 170                 175
Ser Asp Gln Val Trp Ile Met Leu His Ser Gly Ser Arg Gly Ile Gly
            180                 185                 190
Asn Ala Ile Gly Thr Tyr Phe Ile Asp Leu Ala Gln Lys Glu Met Gln
        195                 200                 205
Glu Thr Leu Glu Thr Leu Pro Ser Arg Asp Leu Ala Tyr Phe Met Glu
    210                 215                 220
Gly Thr Glu Tyr Phe Asp Asp Tyr Leu Lys Ala Val Ala Trp Ala Gln
225                 230                 235                 240
Leu Phe Ala Ser Leu Asn Arg Asp Ala Met Met Glu Asn Val Val Thr
                245                 250                 255
Ala Leu Gln Ser Ile Thr Gln Lys Thr Val Arg Gln Pro Gln Thr Leu
            260                 265                 270
Ala Met Glu Glu Ile Asn Cys His His Asn Tyr Val Gln Lys Glu Gln
        275                 280                 285
His Phe Gly Glu Glu Ile Tyr Val Thr Arg Lys Gly Ala Val Ser Ala
    290                 295                 300
Arg Ala Gly Gln Tyr Gly Ile Ile Pro Gly Ser Met Gly Ala Lys Ser
305                 310                 315                 320
Phe Ile Val Arg Gly Leu Gly Asn Glu Glu Ser Phe Cys Ser Cys Ser
                325                 330                 335
His Gly Ala Gly Arg Val Met Ser Arg Thr Lys Ala Lys Lys Leu Phe
            340                 345                 350
Ser Val Glu Asp Gln Ile Arg Ala Thr Ala His Val Glu Cys Arg Lys
        355                 360                 365
Asp Ala Glu Val Ile Asp Glu Ile Pro Met Ala Tyr Lys Asp Ile Asp
    370                 375                 380
Ala Val Met Ala Ala Gln Ser Asp Leu Val Glu Val Ile Tyr Thr Leu
385                 390                 395                 400
Arg Gln Val Val Cys Val Lys Gly
                405
```

```
<210> SEQ ID NO 12
<211> LENGTH: 1518
<212> TYPE: DNA
<213> ORGANISM: homo sapiens

<400> SEQUENCE: 12
atgagtcgca gctataatga tgagctgcag ttcttggaga agatcaataa aaactgctgg       60
aggatcaaga agggcttcgt gcccaacatg caggttgaag gtgttttcta tgtgaatgat      120
gctctggaga aattgatgtt tgaggaatta aggaatgcct gtcgaggtgg tggtgttggt      180
ggcttcctgc cagccatgaa acagattggc aatgtggcag ccctgcctgg aattgttcat      240
cgatctattg gcttcctgta gtccattca ggatatgggt tgctattgg aacatggca         300 gcctttgata tgaatgaccc tgaagcagta gtatcccag gtggtgtcgg gtttgacatc       360
aactgtggtg tccgcttgct aagaaccaat ttagatgaaa gtgatgtcca gcctgtgaag      420
gagcaacttg cccaagctat gtttgaccac attcctgttg gggtggggtc aaaaggtgtc      480
atcccaatga atgccaaaga cttggaggag gccttggaga tggggtgga ctggtcctta       540 agagaagggt atgcctgggc tgaagacaag gagcactgcg aggagtacgg aaggatgctg      600
caggctgacc ccaataaagt ttctgcaagg gcgaagaaaa gaggccttcc tcagttgggg      660
accctgggag caggcaacca ttatgcagaa atccaggttg tggatgagat tttcaatgag      720
tatgctgcta aaaaaatggg catcgaccat aagggacagg tgtgtgtgat gatccacagt      780
ggaagcagag gcttgggcca ccaagtagcc acagatgcgc tggtagctat ggagaaggcc      840
atgaagagag acaagattat agtcaatgat cggcagttgg cttgtgctcg aatcgcttcc      900
ccagagggtc aagactatct gaagggaatg gcagctgctg gaactatgc ctgggtcaac       960 cgctcttcca tgaccttctt aacccgtcag gctttcgcca aggtcttcaa cacaacccct     1020
gatgacttgg acctacatgt gatttatgat gttttctcaca acattgccaa agtggagcag    1080
catgtggtgg acggaaagga acggacactg ttagtacaca ggaagggatc cacccgcgct    1140
ttccctcctc accatcccct cattgctgtt gattaccaac tcactggaca gccagtgctc    1200
attggtggca ccatgggaac ctgtagttat gttcttactg gcactgaaca gggcatgact    1260
gagacctttg gaacaacctg tcatggagcg ggccgtgcat tgtcccgagc aaaatctcga    1320
cgtaatttag atttccagga tgtcttagac aaattggcag atatgggaat tgcgatccgt    1380
gttgcctcac ccaaactggt tatggaagag ctcctgagt cctataagaa tgtgacagat     1440
gtggtaaata cctgccatga tgctggaatc agcaagaaag ccattaaact gagaccaatt    1500
gctgtgatca aaggatag                                                  1518

<210> SEQ ID NO 13
<211> LENGTH: 505
<212> TYPE: PRT
<213> ORGANISM: homo sapiens

<400> SEQUENCE: 13

Met Ser Arg Ser Tyr Asn Asp Glu Leu Gln Phe Leu Glu Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Gly Val Gly Gly Phe Leu Pro
    50                  55                  60
```

```
Ala Met Lys Gln Ile Gly Asn Val Ala Ala Leu Pro Gly Ile Val His
 65                  70                  75                  80

Arg Ser Ile Gly Leu Pro Asp Val His Ser Gly Tyr Gly Phe Ala Ile
                 85                  90                  95

Gly Asn Met Ala Ala Phe Asp Met Asn Asp Pro Glu Ala Val Val Ser
             100                 105                 110

Pro Gly Gly Val Gly Phe Asp Ile Asn Cys Gly Val Arg Leu Leu Arg
         115                 120                 125

Thr Asn Leu Asp Glu Ser Asp Val Gln Pro Val Lys Glu Gln Leu Ala
     130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                 165                 170                 175

Asp Trp Ser Leu Arg Glu Gly Tyr Ala Trp Ala Glu Asp Lys Glu His
             180                 185                 190

Cys Glu Glu Tyr Gly Arg Met Leu Gln Ala Asp Pro Asn Lys Val Ser
         195                 200                 205

Ala Arg Ala Lys Lys Arg Gly Leu Pro Gln Leu Gly Thr Leu Gly Ala
     210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                 245                 250                 255

Met Ile His Ser Gly Ser Arg Gly Leu Gly His Gln Val Ala Thr Asp
             260                 265                 270

Ala Leu Val Ala Met Glu Lys Ala Met Lys Arg Asp Lys Ile Ile Val
         275                 280                 285

Asn Asp Arg Gln Leu Ala Cys Ala Arg Ile Ala Ser Pro Glu Gly Gln
     290                 295                 300

Asp Tyr Leu Lys Gly Met Ala Ala Ala Gly Asn Tyr Ala Trp Val Asn
305                 310                 315                 320

Arg Ser Ser Met Thr Phe Leu Thr Arg Gln Ala Phe Ala Lys Val Phe
                 325                 330                 335

Asn Thr Thr Pro Asp Asp Leu Asp Leu His Val Ile Tyr Asp Val Ser
             340                 345                 350

His Asn Ile Ala Lys Val Glu Gln His Val Val Asp Gly Lys Glu Arg
         355                 360                 365

Thr Leu Leu Val His Arg Lys Gly Ser Thr Arg Ala Phe Pro Pro His
     370                 375                 380

His Pro Leu Ile Ala Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                 405                 410                 415

Gln Gly Met Thr Glu Thr Phe Gly Thr Thr Cys His Gly Ala Gly Arg
             420                 425                 430

Ala Leu Ser Arg Ala Lys Ser Arg Arg Asn Leu Asp Phe Gln Asp Val
         435                 440                 445

Leu Asp Lys Leu Ala Asp Met Gly Ile Ala Ile Arg Val Ala Ser Pro
     450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
```

```
                    485              490              495
Leu Arg Pro Ile Ala Val Ile Lys Gly
           500                505

<210> SEQ ID NO 14
<211> LENGTH: 1521
<212> TYPE: DNA
<213> ORGANISM: Drosophila melanogaster

<400> SEQUENCE: 14
atggtggtgc gtccgtacaa cgatgagctc cggtacctgg agaaagtgag cgaccactgc      60
tggcgcatca agaagggctt ccagccaaat atgaatgtgg aggggtgttt ctatgtgaac     120
agccggctgg agcgcctgat gctggaggag ctgaagaact cctgtcgccc gggcgcagtg     180
ggtggcttcc tgcctggcgt caagcagata gccaatgtgg ccgcgttgcc gggcatcgtg     240
ggcaggtcca ttggactgcc cgacattcat tccggctacg gatttgccat cgggaacatg     300
gctgctttcg acatgaacga tccgctgtcc gttgtaagtc ccggcggcgt gggtttcgac     360
atcaactgtg gcgtgcgtct gctgcgcacg aatctgtacg agaaggatgt gcagccggtg     420
aaggagcaac tggcgcagtc cctgttcgat cacataccccg tgggtgtggg ctccaagggc     480
atcataccca tgaatgcccg cgatctggag gaggccctcg aaatgggcat ggactggtcg     540
ctgcgcgagg gatacgtgtg gcggaggac aaggagcatt gcgaggagta cggccgcatg     600
ctgaacgccg atcccgccaa ggtgagcatg cgggccaaga agcgagggct gccccagctg     660
ggcactctgg gtgcgggcaa tcactacgcc gagatccagg tggtgacga aatctacgac     720
aagtggagcg cctccaagat gggcatcgag agaagggcc aggtggtggt gatgattcac     780
tcgggcagtc gtggcttcgg ccaccaggtc gctaccgacg ccctggtcca gatggagaag     840
gccatgaagc gggacaagat cgagaccaat gaccggcagc tggcctgcgc caggatcaat     900
tcggtggagg acaggactca cttgaaggcc atggcggcgg ctgcgaactt tgcctgggtg     960
aatcgcagct ccatgacatt cctcacccgt caagcgtttg ccaagatgtt taacaccaca    1020
cccgatgatc tcgacatgca cgttatctat gacgtttcgc acaatattgc caaggtggag    1080
aaccacatgg tggacggcaa ggagcggaag ctgttggttc accggaaggg ctccacgcgc    1140
gccttcccgc acaccatccc ctgatcccca gtggactatc agcttaccgg cagccagtc    1200
ctcgtcggtg gaaccatggg cacttgcagt tacgtgctaa ctggaacgga cagggcatg    1260
caggagacgt tcggtagcac ttgccacgga gcgggtcgtg cactatctcg agccaaatcc    1320
cggcgcaatc tggactacaa ggatgtgctg acaagctgg accagttggg catcgccata    1380
cgcgtggcct cgcccaaact ggtcatggag gaggcacccg aatcttacaa ggacgtgacc    1440
gatgtggtcg acacctgtca cgcagctggc atcagcaaaa agtgcatcaa gatgcgccca    1500
attgcagtta tcaagggcta a                                              1521

<210> SEQ ID NO 15
<211> LENGTH: 506
<212> TYPE: PRT
<213> ORGANISM: Drosophila melanogaster

<400> SEQUENCE: 15

Met Val Val Arg Pro Tyr Asn Asp Glu Leu Arg Tyr Leu Glu Lys Val
1               5                   10                  15

Ser Asp His Cys Trp Arg Ile Lys Lys Gly Phe Gln Pro Asn Met Asn
            20                  25                  30
```

-continued

Val Glu Gly Cys Phe Tyr Val Asn Ser Arg Leu Glu Arg Leu Met Leu
         35                  40                  45

Glu Glu Leu Lys Asn Ser Cys Arg Pro Gly Ala Val Gly Gly Phe Leu
 50                  55                  60

Pro Gly Val Lys Gln Ile Ala Asn Val Ala Ala Leu Pro Gly Ile Val
 65                  70                  75                  80

Gly Arg Ser Ile Gly Leu Pro Asp Ile His Ser Gly Tyr Gly Phe Ala
                 85                  90                  95

Ile Gly Asn Met Ala Ala Phe Asp Met Asn Asp Pro Leu Ser Val Val
             100                 105                 110

Ser Pro Gly Gly Val Gly Phe Asp Ile Asn Cys Gly Val Arg Leu Leu
         115                 120                 125

Arg Thr Asn Leu Tyr Glu Lys Asp Val Gln Pro Val Lys Glu Gln Leu
 130                 135                 140

Ala Gln Ser Leu Phe Asp His Ile Pro Val Gly Val Gly Ser Lys Gly
145                 150                 155                 160

Ile Ile Pro Met Asn Ala Arg Asp Leu Glu Glu Ala Leu Glu Met Gly
                165                 170                 175

Met Asp Trp Ser Leu Arg Glu Gly Tyr Val Trp Ala Glu Asp Lys Glu
             180                 185                 190

His Cys Glu Glu Tyr Gly Arg Met Leu Asn Ala Asp Pro Ala Lys Val
         195                 200                 205

Ser Met Arg Ala Lys Lys Arg Gly Leu Pro Gln Leu Gly Thr Leu Gly
 210                 215                 220

Ala Gly Asn His Tyr Ala Glu Ile Gln Val Val Asp Glu Ile Tyr Asp
225                 230                 235                 240

Lys Trp Ser Ala Ser Lys Met Gly Ile Glu Glu Lys Gly Gln Val Val
                245                 250                 255

Val Met Ile His Ser Gly Ser Arg Gly Phe Gly His Gln Val Ala Thr
             260                 265                 270

Asp Ala Leu Val Gln Met Glu Lys Ala Met Lys Arg Asp Lys Ile Glu
         275                 280                 285

Thr Asn Asp Arg Gln Leu Ala Cys Ala Arg Ile Asn Ser Val Glu Gly
 290                 295                 300

Gln Asp Tyr Leu Lys Ala Met Ala Ala Ala Asn Phe Ala Trp Val
305                 310                 315                 320

Asn Arg Ser Ser Met Thr Phe Leu Thr Arg Gln Ala Phe Ala Lys Met
                325                 330                 335

Phe Asn Thr Thr Pro Asp Asp Leu Asp Met His Val Ile Tyr Asp Val
             340                 345                 350

Ser His Asn Ile Ala Lys Val Glu Asn His Met Val Asp Gly Lys Glu
         355                 360                 365

Arg Lys Leu Leu Val His Arg Lys Gly Ser Thr Arg Ala Phe Pro Pro
 370                 375                 380

His His Pro Leu Ile Pro Val Asp Tyr Gln Leu Thr Gly Gln Pro Val
385                 390                 395                 400

Leu Val Gly Gly Thr Met Gly Thr Cys Ser Tyr Val Leu Thr Gly Thr
                405                 410                 415

Glu Gln Gly Met Gln Glu Thr Phe Gly Ser Thr Cys His Gly Ala Gly
             420                 425                 430

Arg Ala Leu Ser Arg Ala Lys Ser Arg Arg Asn Leu Asp Tyr Lys Asp
         435                 440                 445

Val Leu Asp Lys Leu Asp Gln Leu Gly Ile Ala Ile Arg Val Ala Ser

```
            450                 455                 460
Pro Lys Leu Val Met Glu Glu Ala Pro Glu Ser Tyr Lys Asp Val Thr
465                 470                 475                 480

Asp Val Val Asp Thr Cys His Ala Ala Gly Ile Ser Lys Lys Cys Ile
                485                 490                 495

Lys Met Arg Pro Ile Ala Val Ile Lys Gly
            500                 505
```

<210> SEQ ID NO 16
<211> LENGTH: 1518
<212> TYPE: DNA
<213> ORGANISM: Danio rerio

<400> SEQUENCE: 16

| | | | | | |
|---|---|---|---|---|---|
| atgagtcgct | cttacaacga | tgagctccag | tatctggata | aaatacacaa | aaactgctgg | 60 |
| cggatcaaga | agggtttcgt | gccgaatatg | ctggtggaag | gagtgttta | tgtcaatgac | 120 |
| ccgctggaaa | agctgatgtt | cgaggagctg | agaaacgcct | gtcgcggagg | agggtttgga | 180 |
| ggtttcttac | ctgcgatgaa | gcagattggg | aatgtggccg | ctctgccagg | aatcgtgcac | 240 |
| cggtcgatcg | gttaccgga | cgttcactca | ggatacggat | cgctatcgg | gaacatggca | 300 |
| gcgttcgaca | tggagaatcc | ggacgcagtc | gtctctccag | gcggtgtggg | tttcgatatt | 360 |
| aactgtggtg | ttcgtctgct | gcgcacaaac | ctggatgagg | gcgacgttca | gccggtgaag | 420 |
| gagcagctgg | cacagtctct | cttcgaccac | atccctgtcg | gagtcggctc | caagggcgtc | 480 |
| attcctatgg | gtgcaaagga | cctggaggag | gcgttggaga | tgggtgtgga | ctggtctctg | 540 |
| agggagggat | atgcctgggc | ggaggataaa | gagcactgtg | aggagtacgg | acgcatgctg | 600 |
| caggccgacc | caaacaaagt | ctcctccaaa | gccaagaaga | gggactgcc | acagttggga | 660 |
| actctgggtg | caggaaacca | ctacgcagag | attcaggtgg | tggacgagat | ctacaatgat | 720 |
| tacgccgcca | gaagatggg | catcgatcat | aaagggcagg | tgtgtgtgat | gatccacagc | 780 |
| ggcagccgag | gactcggaca | tcaggtggcc | accgacgctc | tggtggcgat | ggagaaggcc | 840 |
| atgaagcgcg | accgcatcac | agtaaacgac | cggcagctag | cgtgcgcgcg | catcacgtca | 900 |
| gaagagggac | aggattatct | gaagggaatg | gcggcagcag | gaaactacgc | ctgggtcaac | 960 |
| cgatcctcca | tgaccttcct | cacacgacag | gcgttctcca | agtgttcag | caccacacca | 1020 |
| gatgatctgg | acatgcacgt | gatctacgac | gtctcgcaca | catcgccaa | agtggaggag | 1080 |
| cacatggtgg | acggccggca | gaaaacactg | ctggtgcata | ggaagggctc | caccagagcg | 1140 |
| tttcctccac | accatccact | catacctgta | gactatcagc | tgaccggtca | gccagtcctg | 1200 |
| attggaggaa | ccatgggcac | ctgcagttac | gtgctcacag | gcacagagca | gggcatgaca | 1260 |
| gagacgttcg | gcaccacatg | tcacggcgct | ggccgagctt | atccagagc | caaatccaga | 1320 |
| cgcaacctgg | acttccagga | tgttctggat | aaactggcag | acatgggcat | cgctattaga | 1380 |
| gtggcgtcac | cgaagctggt | gatggaggag | gctcccgagt | cctacaagaa | cgtgacagac | 1440 |
| gtggtgaaca | catgccatga | tgccggcatc | agcaaaaaag | ccatcaaact | cagacccatc | 1500 |
| gctgtgatta | aggttaa | | | | | 1518 |

<210> SEQ ID NO 17
<211> LENGTH: 505
<212> TYPE: PRT
<213> ORGANISM: Danio rerio

<400> SEQUENCE: 17

```
Met Ser Arg Ser Tyr Asn Asp Glu Leu Gln Tyr Leu Asp Lys Ile His
1               5                   10                  15

Lys Asn Cys Trp Arg Ile Lys Lys Gly Phe Val Pro Asn Met Leu Val
            20                  25                  30

Glu Gly Val Phe Tyr Val Asn Asp Pro Leu Glu Lys Leu Met Phe Glu
        35                  40                  45

Glu Leu Arg Asn Ala Cys Arg Gly Gly Phe Gly Gly Phe Leu Pro
50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Glu Asn Pro Asp Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Gly Asp Val Gln Pro Val Lys Glu Gln Leu Ala
130                 135                 140

Gln Ser Leu Phe Asp His Ile Pro Val Gly Val Gly Ser Lys Gly Val
145                 150                 155                 160

Ile Pro Met Gly Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Ser Lys Ala Lys Lys Arg Gly Leu Pro Gln Leu Gly Thr Leu Gly Ala
210                 215                 220

Gly Asn His Tyr Ala Glu Ile Gln Val Val Asp Glu Ile Tyr Asn Asp
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Arg Ile Thr Val
        275                 280                 285

Asn Asp Arg Gln Leu Ala Cys Ala Arg Ile Thr Ser Glu Glu Gly Gln
290                 295                 300

Asp Tyr Leu Lys Gly Met Ala Ala Ala Gly Asn Tyr Ala Trp Val Asn
305                 310                 315                 320

Arg Ser Ser Met Thr Phe Leu Thr Arg Gln Ala Phe Ser Lys Val Phe
                325                 330                 335

Ser Thr Thr Pro Asp Asp Leu Asp Met His Val Ile Tyr Asp Val Ser
            340                 345                 350

His Asn Ile Ala Lys Val Glu Glu His Met Val Asp Gly Arg Gln Lys
        355                 360                 365

Thr Leu Leu Val His Arg Lys Gly Ser Thr Arg Ala Phe Pro Pro His
370                 375                 380

His Pro Leu Ile Pro Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
```

```
                420             425              430
Ala Leu Ser Arg Ala Lys Ser Arg Arg Asn Leu Asp Phe Gln Asp Val
            435                 440                 445

Leu Asp Lys Leu Ala Asp Met Gly Ile Ala Ile Arg Val Ala Ser Pro
    450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
                500             505

<210> SEQ ID NO 18
<211> LENGTH: 1518
<212> TYPE: DNA
<213> ORGANISM: Bos sp.

<400> SEQUENCE: 18
atgagtcgca gttataatga tgagctgcag ttcttggaaa agatcagtaa gaactgctgg      60
agaatcaaga agggcttcgt gcccaacatg caggttgaag agttttccta tgtgaatgat     120
tctctggaaa aattaatgtt tgaagaatta aggaatgcct gtcgaggtgg tggtgttggt     180
ggcttcctgc cagccatgaa acaaattggc aatgtggccg ccctgcctgg gattgttcat     240
cgatccatcg gtcttcctga tgtccattca ggttatgggt ttgctattgg aaatatggca     300
gcctttgata tgaacgaccc tgaagcagtg gtatccccag gtggtgttgg gtttgacatt     360
aactgtggtg tccgcttgct gagaaccaat ttagatgaaa gtgatgttca gcctgtgaaa     420
gagcaacttg cccaagctat gtttgaccac attcctgtgg gagtggggtc aaaaggtgtc     480
atcccaatga atgccaaaga cttggaggag gccttggaga tgggtgtgga ctggtccctg     540
agagaaggct atgcctgggc agaggacaag gagcactgtg aggagtatgg aaggatgctg     600
caagctgatc ccaataaagt ctcagccagg gctaaaaaaa gaggccttcc ccagttgggg     660
actctgggag caggcaacca ctatgcagaa atccaggttg tggatgagat tttcaacgag     720
tatgctgcta gaaaatgggg cattgaccat aagggacagg tgtgtgtgat gatccacagt     780
ggaagcagag gcttgggcca ccaagttgcc acagatgcac ttgtagctat ggaaaaagcc     840
atgaagagag acaagattat agtcaatgac cgtcagttgg cttgtgctcg aattgcttcc     900
ccagagggtc aggactacct gaagggaatg gcagcggctg gaactatgc ctgggtcaac      960 cgctcttcca tgaccttctt aacccgtcag gcttttgcca aggtcttcaa cacaaccct     1020 gatgacttgg acctgcatgt gatctatgat gtttctcaca atattgccaa agtagaacag    1080
catgtggtgg acgggaagga gcggactctg ttagtacaca ggaaggggtc cacccgagcc    1140
ttccctcctc accatcccct cattgcggtt gattaccaac ttaccggaca accagtgctc    1200
attggtggca ccatgggaac ctgtagctat gttcttactg gtactgagca gggcatgact    1260
gaaacctttg gaacaacttg tcatggagcg gccgtgcac tgtcccgagc aaagtcaaga     1320
cgtaatttag atttccagga tgtcctcgac aaattggcag acatgggaat tgcaatccgt    1380
gtcgcctcac ccaagctggt aatggaagag cccctgagt cctataagaa cgtgacggat     1440
gtggtgaaca cctgccatga tgccggaatc agcaagaagg ccattaaact gaggccaatt    1500
gctgttatca aaggatag                                                   1518

<210> SEQ ID NO 19
```

```
<211> LENGTH: 505
<212> TYPE: PRT
<213> ORGANISM: Bos sp.

<400> SEQUENCE: 19

Met Ser Arg Ser Tyr Asn Asp Glu Leu Gln Phe Leu Glu Lys Ile Ser
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ser Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Ala Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
    290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Leu Asp Leu His Val Ile Tyr Asp Val Ser
            340                 345                 350

His Asn Ile Ala Lys Val Glu Gln His Val Val Asp Gly Lys Glu Arg
        355                 360                 365

Thr Leu Leu Val His Arg Lys Gly Ser Thr Arg Ala Phe Pro Pro His
    370                 375                 380

His Pro Leu Ile Ala Val Asp Tyr Gln Leu Thr Gly Gln Pro Val Leu
```

```
            Ile Gly Gly Thr Met Gly Thr Cys Ser Tyr Val Leu Thr Gly Thr Glu
    385                 390                 395                 400
                        405                 410                 415
Gln Gly Met Thr Glu Thr Phe Gly Thr Thr Cys His Gly Ala Gly Arg
            420                 425                 430
Ala Leu Ser Arg Ala Lys Ser Arg Asn Leu Asp Phe Gln Asp Val
                435                 440                 445
Leu Asp Lys Leu Ala Asp Met Gly Ile Ala Ile Arg Val Ala Ser Pro
    450                 455                 460
Lys Leu Val Met Glu Glu Ala Pro Glu Ser Tyr Lys Asn Val Thr Asp
465                 470                 475                 480
Val Val Asn Thr Cys His Asp Ala Gly Ile Ser Lys Lys Ala Ile Lys
                    485                 490                 495
Leu Arg Pro Ile Ala Val Ile Lys Gly
                500                 505

<210> SEQ ID NO 20
<211> LENGTH: 1518
<212> TYPE: DNA
<213> ORGANISM: Mus sp.

<400> SEQUENCE: 20
atgagtcgta actacaacga tgagctacag ttcttggaca agatcaataa aaactgctgg      60
aggatcaaga agggctttgt gcccaacatg caggttgaag gagtgttta tgtgaatgat      120 gctctggaaa aactaatgtt tgaggaatta aggaacgcct gtcgaggtgg tggtgttggt      180
ggctttctgc cagccatgaa gcagattggc aatgtggcag ccctgcctgg aatagttcat      240
cggtctatcg gcttcctga tgtccattca ggctatgggt ttgccatagg aacatggct       300 gcctttgata tgaatgaccc tgaggccgtt gtatccccag gtggtgtcgg atttgatatt      360
aactgtggtg tccgcttgct aagaaccaat ttagatgaga gcgatgtaca gcctgtgaag      420
gaacaacttg cccaagctat gtttgaccac atccctgttg gggtgggatc aaaaggtgtc      480
attccaatga atgccaaaga cttggaggag cattggaaga tggggtgga ctggtccctg       540 agggaaggct atgcctgggc tgaagacaag gagcactgtg aggagtatgg aaggatgctg      600
caagccgacc ccataaggt ctcacccagg gcaaagaaaa ggggccttcc tcagttgggg       660
accctgggag caggcaacca ttatgcagaa atccaggttg tagatgagat ttcaatgag       720 tatgccgcca agaagatggg catcgaccat aagggacagg tgtgtgtgat gatccacagt      780
ggaagcagag gcttgggcca ccaagtagct acagatgcac tggtagctat ggaaaaggcc      840
atgaagagag acaagattat agtcaatgac cggcagttgg cttgtgctcg gattgcatcc      900
ccagagggac aagactatct aaagggaatg gctgcagctg aaactacgc tgggttaac        960 cgctcctcta tgaccttctt aacccgtcag gcttttgcca aagtcttcaa cacaaccct       1020 gatgacctgg acctgcatgt gatctatgat gtgtcgcaca atatcgccaa agtggagcag      1080
cacgtggtgg atgggaagga acggacgctg ctggtgcaca ggaagggatc cacccgtgct      1140
ttcccgcctc accaccccct cattgctgtg gattatcaac tcacaggaca accagtgctt      1200
attggtggca ccatggggac ctgtagttac gttctgactg gcactgaaca aggcatgact      1260
gagacctttg gaacaacctg tcatggagcg ggccgtgctt tgtccagagc aaaatcacgt      1320
cgtaacttag atttccaaga tgtcttagac aaactggcag acatgggaat tgcaatccgg      1380
gttgcttccc ccaagctggt tatggaagag gcaccagagt cctataagaa tgtgacagac      1440
```

-continued

```
gtcgtgaaca cctgccatga tgctgggatc agcaagaagg ccattaaact gagaccaatt    1500
gctgttatta aagggtag                                                  1518
```

<210> SEQ ID NO 21
<211> LENGTH: 505
<212> TYPE: PRT
<213> ORGANISM: Mus sp.

<400> SEQUENCE: 21

```
Met Ser Arg Asn Tyr Asn Asp Glu Leu Gln Phe Leu Asp Lys Ile Asn
1               5                  10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Pro Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
    290                 295                 300

Asp Tyr Leu Lys Gly Met Ala Ala Gly Asn Tyr Ala Trp Val Asn
305                 310                 315                 320

Arg Ser Ser Met Thr Phe Leu Thr Arg Gln Ala Phe Ala Lys Val Phe
                325                 330                 335

Asn Thr Thr Pro Asp Asp Leu Asp Leu His Val Ile Tyr Asp Val Ser
            340                 345                 350

His Asn Ile Ala Lys Val Glu Gln His Val Val Asp Gly Lys Glu Arg
```

```
               355                 360                 365
Thr Leu Leu Val His Arg Lys Gly Ser Thr Arg Ala Phe Pro Pro His
            370                 375                 380

His Pro Leu Ile Ala Val Asp Tyr Gln Leu Thr Gly Gln Pro Val Leu
385                 390                 395                 400

Ile Gly Gly Thr Met Gly Thr Cys Ser Tyr Val Leu Thr Gly Thr Glu
                405                 410                 415

Gln Gly Met Thr Glu Thr Phe Gly Thr Thr Cys His Gly Ala Gly Arg
            420                 425                 430

Ala Leu Ser Arg Ala Lys Ser Arg Arg Asn Leu Asp Phe Gln Asp Val
            435                 440                 445

Leu Asp Lys Leu Ala Asp Met Gly Ile Ala Ile Arg Val Ala Ser Pro
        450                 455                 460

Lys Leu Val Met Glu Glu Ala Pro Glu Ser Tyr Lys Asn Val Thr Asp
465                 470                 475                 480

Val Val Asn Thr Cys His Asp Ala Gly Ile Ser Lys Lys Ala Ile Lys
                485                 490                 495

Leu Arg Pro Ile Ala Val Ile Lys Gly
            500                 505

<210> SEQ ID NO 22
<211> LENGTH: 1518
<212> TYPE: DNA
<213> ORGANISM: Rattus sp.

<400> SEQUENCE: 22
atgagtcgta actacaacga tgagctacag ttcttggaca agatcaataa gaactgctgg      60
aggatcaaga agggctttgt gcccaacatg caggttgaag gggtgtttta tgtgaatgac     120
gctctggaaa agctcatgtt tgaggagtta cggaatgcct gtcgaggtgg tggtgttggt     180
ggcttcctgc cagccatgaa gcagattggc aatgtggcag ccctgcctgg aatagttcat     240
cggtctattg gcttcctga tgtccactca ggctacgggt ttgccatagg gaacatggct     300
gcctttgata tgaatgaccc tgaggcagtt gtatccccag gtggtgtcgg atttgatatt     360
aactgtggtg tccgcttgct aaggaccaat ttagatgaga gcgatgtaca gcctgtgaag     420
gaacaacttg cccaagctat gttttgaccac atccctgtcg gggtgggatc gaaaggtgtc     480
attccaatga atgccaaaga cttggaggag cattggagga tgggtgtgga ctggtcccta     540
agagaaggct atgcctgggc tgaggacaag gagcactgtg aggagtatgg aaggatgctc     600
caagccgacc ccaataaggt ctcacccaga gcaaagaaaa ggggccttcc tcagttgggg     660
accctgggag caggcaacca ttatgcagag atccaggttg tagatgagat ttcaacgag      720 tatgctgcca gaagatggg catcgaccat aagggacagg tgtgcgtgat gatccacagc     780
gggagcagag gcttgggcca tcaagtagct acagacgcac tggtagctat ggagaaagcc     840
atgaagagag acaagattat agtcaatgac cggcagctgg cgtgtgctcg gattgcatcc     900
ccagagggac aagactatct aaagggaatg gctgccgctg gaaactgtgc ctgggttaac     960
cgctcgtcta tgaccttctt aacccgtcag gcttttgcca aagtcttcaa cacaacccct    1020
gacgacctgg acctgcatgt gatttatgat gtttctcaca catcgccaa agtggagcag     1080 cacgtggtag acggaaagga gcggacgctg ttggtgcaca ggaaagggtc cacccgcgct    1140
ttccctcctc accatcccct cattgctgtt gattaccagc tcactggaca accagtgctt    1200
atcggtggca ccatggggac ctgtagttat gttctgactg gcactgaaca aggcatgact    1260
```

```
gagacctttg aacaacctg tcatggagcg gccgtgctt tgtccagagc aaaatcacgt    1320
cgtaatttag atttccaaga tgtcttagac aagctggcag acatgggaat cgccatccgg    1380
gttgcgtccc ccaagctggt tatggaagag gctccagaat catataagaa tgtgacagac    1440
gtcgtgaaca cttgccatga tgctgggatc agcaagaagg ccattaaact gagaccaatt    1500
gctgttatta aaggatag                                                  1518
```

<210> SEQ ID NO 23
<211> LENGTH: 505
<212> TYPE: PRT
<213> ORGANISM: Rattus sp.

<400> SEQUENCE: 23

```
Met Ser Arg Asn Tyr Asn Asp Glu Leu Gln Phe Leu Asp Lys Ile Asn
1               5                   10                  15

Lys Asn Cys Trp Arg Ile Lys Lys Gly Phe Val Pro Asn Met Gln Val
            20                  25                  30

Glu Gly Val Phe Tyr Val Asn Asp Ala Leu Glu Lys Leu Met Phe Glu
        35                  40                  45

Glu Leu Arg Asn Ala Cys Arg Gly Gly Val Gly Gly Phe Leu Pro
    50                  55                  60

Ala Met Lys Gln Ile Gly Asn Val Ala Ala Leu Pro Gly Ile Val His
65                  70                  75                  80

Arg Ser Ile Gly Leu Pro Asp Val His Ser Gly Tyr Gly Phe Ala Ile
                85                  90                  95

Gly Asn Met Ala Ala Phe Asp Met Asn Asp Pro Glu Ala Val Val Ser
            100                 105                 110

Pro Gly Gly Val Gly Phe Asp Ile Asn Cys Gly Val Arg Leu Leu Arg
        115                 120                 125

Thr Asn Leu Asp Glu Ser Asp Val Gln Pro Val Lys Glu Gln Leu Ala
    130                 135                 140

Gln Ala Met Phe Asp His Ile Pro Val Gly Val Gly Ser Lys Gly Val
145                 150                 155                 160

Ile Pro Met Asn Ala Lys Asp Leu Glu Glu Ala Leu Glu Met Gly Val
                165                 170                 175

Asp Trp Ser Leu Arg Glu Gly Tyr Ala Trp Ala Glu Asp Lys Glu His
            180                 185                 190

Cys Glu Glu Tyr Gly Arg Met Leu Gln Ala Asp Pro Asn Lys Val Ser
        195                 200                 205

Pro Arg Ala Lys Lys Arg Gly Leu Pro Gln Leu Gly Thr Leu Gly Ala
    210                 215                 220

Gly Asn His Tyr Ala Glu Ile Gln Val Val Asp Glu Ile Phe Asn Glu
225                 230                 235                 240

Tyr Ala Ala Lys Lys Met Gly Ile Asp His Lys Gly Gln Val Cys Val
                245                 250                 255

Met Ile His Ser Gly Ser Arg Gly Leu Gly His Gln Val Ala Thr Asp
            260                 265                 270

Ala Leu Val Ala Met Glu Lys Ala Met Lys Arg Asp Lys Ile Ile Val
        275                 280                 285

Asn Asp Arg Gln Leu Ala Cys Ala Arg Ile Ala Ser Pro Glu Gly Gln
    290                 295                 300

Asp Tyr Leu Lys Gly Met Ala Ala Gly Asn Cys Ala Trp Val Asn
305                 310                 315                 320
```

-continued

```
Arg Ser Ser Met Thr Phe Leu Thr Arg Gln Ala Phe Ala Lys Val Phe
            325             330             335
Asn Thr Thr Pro Asp Asp Leu Asp Leu His Val Ile Tyr Asp Val Ser
            340             345             350
His Asn Ile Ala Lys Val Glu Gln His Val Val Asp Gly Lys Glu Arg
            355             360             365
Thr Leu Leu Val His Arg Lys Gly Ser Thr Arg Ala Phe Pro Pro His
        370             375             380
His Pro Leu Ile Ala Val Asp Tyr Gln Leu Thr Gly Gln Pro Val Leu
385             390             395             400
Ile Gly Gly Thr Met Gly Thr Cys Ser Tyr Val Leu Thr Gly Thr Glu
            405             410             415
Gln Gly Met Thr Glu Thr Phe Gly Thr Thr Cys His Gly Ala Gly Arg
            420             425             430
Ala Leu Ser Arg Ala Lys Ser Arg Arg Asn Leu Asp Phe Gln Asp Val
            435             440             445
Leu Asp Lys Leu Ala Asp Met Gly Ile Ala Ile Arg Val Ala Ser Pro
        450             455             460
Lys Leu Val Met Glu Glu Ala Pro Glu Ser Tyr Lys Asn Val Thr Asp
465             470             475             480
Val Val Asn Thr Cys His Asp Ala Gly Ile Ser Lys Lys Ala Ile Lys
            485             490             495
Leu Arg Pro Ile Ala Val Ile Lys Gly
            500             505
```

USE OF A HSPC117 MOLECULE AS RNA LIGASE

CROSS REFERENCE TO RELATED APPLICATIONS

This application is a National Stage of International Application No. PCT/EP2011/064884 filed Aug. 30, 2011, claiming priority based on European Patent Application No. 10174549.5 filed Aug. 30, 2010, the contents of all of which are incorporated herein by reference in their entirety.

The present invention relates to the field of cell and molecular biology tools, in particular to RNA ligases, and methods for using and suppressing an RNA ligase for analysis and therapeutics.

Natural enzymes that ligate RNA or DNA generally join a nucleic acid molecule having a phosphoryl group at the 5' position to a second nucleic acid molecule having a hydroxyl group at the 3' position. The phosphate on the 5' end is usually provided by ATP in an energy transferring step.

Figure 1A:
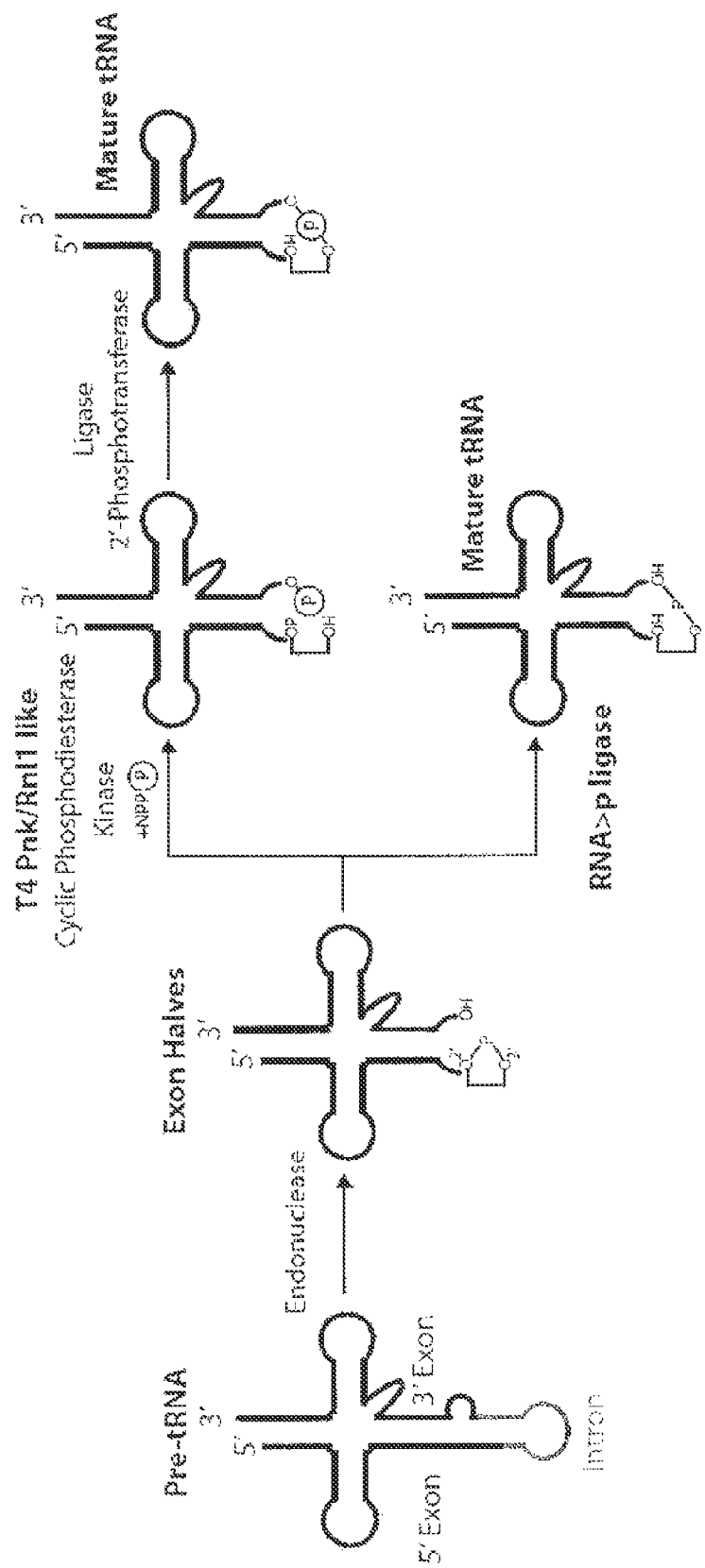

Transfer RNAs (tRNAs) are essential adaptor molecules for the translation of messenger RNA (mRNA) into proteins. Similar to other RNA molecules, precursor tRNA transcripts (pre-tRNAs) are subjected to extensive posttranscriptional processing before they are to fulfil their biological functions. In addition to the removal of 5'-leader and 3'-trailer sequences, extensive base and sugar modifications and template-independent addition of nucleotides, some tRNAs have to undergo excision of an intervening sequence. Removal of tRNA introns is accomplished by a splicing process that differs from canonical spliceosome-dependent processing of mRNA. tRNA splicing rather requires a specialized endonuclease excising the intron and a ligase to join the exon halves (FIG. 1A).

The WO 2004/087884 A2 describes methods to screen for small organic molecules involved in tRNA processing.

Pascal et al., Current Opinion in Structural Biology 18 (1) (2008): 96-105, relates to differences in PNA and RNA ligases. Kato et al., Journal of Molecular Biology 239 (5) (2003): 903-911, describe a crystal structure of a RNA ligase of *Thermus thermophilus*. Wang et al., RNA 11 (6) (2005): 966-975 performed a structure-function analysis of yeast tRNA ligase. Okada et al., PROTEINS 63 (4) (2006): 1119-1122, provide a crystal structure of a RtcB homologuous protein from *Pyrococcus horikoshii*, a RNA cyclase.

Although the presence of introns in tRNA genes seems to be common to all domains of life, evolution of the splicing machinery has apparently diverged at the ligation step. Two major ligation pathways have been described which can be attributed to distinct kingdoms of life (Abelson et al., 1998). The fungal and plant clades use a common ligation mechanism catalyzed by single multifunctional polypeptides that are homologous to bacteriophage T4 RNA ligase 1. This pathway requires the action of cyclic phosphodiesterase and polynucleotide kinase activities to prepare the exon termini for subsequent ligation. As a consequence, an exogenous phosphate originating from a nucleoside triphosphate (NTP) donor is incorporated into the mature tRNA (FIG. 1A, upper branch). In contrast, the animal and archaebacteria clades may ligate tRNA exons by directly joining the 2',3'-cyclic phosphate and 5'-hydroxyl (5'-OH) termini left after the endonuclease reaction (Laski et al., 1983). This ligase reaction (FIG. 1A, lower branch) is dependent on 2',3'-cyclic-phosphate terminated RNA (RNA>p) and results in incorporation of the precursor-derived 2',3'-cyclic phosphate into the splice junction of mature tRNA as a 3',5'-phosphodiester (Filipowicz and Shatkin, 1983). Key biochemical aspects of this RNA>p ligase reaction have been elucidated. However, despite many biochemical, bioinformatics and genetic efforts, no suitable RNA ligase has been identified since the tRNA splicing pathway was initially postulated.

It is therefore a goal of the present invention to provide an RNA ligase that is at least also capable of using 2',3'-cyclic phosphate terminated RNA as substrate ("RNA>p ligase"). This goal is achieved by the subject matter of the claims.

In particular, the present invention relates to the use of a HSPC117 molecule as RNA ligase as a molecular biology tool and in therapeutics. HSPC117 has been sequenced (e.g. Genbank ACC NO: NP_055121 or CAG33456), and located at chromosome 22 orf 28 ("C22ORF28"). HSPC117 is the human homolog of the bacterial/archaeal RtcB gene family characterised by a highly conserved domain of unknown function (UPF0027) and a unique protein fold. UPF0027 proteins form a cluster of orthologous genes (KOG3833) with no detectable representatives in the plant or fungal model organisms. This phyletic distribution is highly reminiscent of the exclusive occurrence of RNA>p ligase activity in animals and archaea. HSPC117 is also referred herein as HSPC117/C22ORF28 or RtcB/HSPC117. As used herein the expression "HSPC117 molecule" refers to any homologous or orthologous molecule in this cluster which has now been identified to catalyze an RNA ligase reaction. Example sequences of such "HSPC117 molecules" are given in FIG. 6 as SEQ ID NO: 1 to SEQ ID NO: 11. All HSPC117 molecules have been found to contain the catalytic cysteine residue corresponding to C122 of SEQ ID NO: 1.

HSPC117 molecules and sequences have been further described, e.g. in the US 2007/0204352 A1 (especially SEQ ID NOs: 15, 16, 69, 70, 71, 72, 73, 74, 75, 76, 77, 78), however without prior recognition of the inventive uses. The US 2007/0204352 A1 relates to a screening of genes potentially involved in the aggregation of alpha-synclein. At paragraph [50], the US 2007/0204352 A1 provides background on the remarkable degree of evolutionary conservation of HSPC117 genes, which proteins can be used in a method of the present invention, in the knowledge of a new function of these HSPC117 molecules.

The inventive RNA ligase can be used to catalyze the transfer of a first RNA to a second RNA. The ends of both RNA can be connected by the ligase. This connection is usually a covalent connection of a phosphor diester bond between both RNA. In particular, one RNA may comprise a 3' phosphate, in particular in form of a 2',3'-cyclic phosphate, and the other may comprise a 5'-OH terminus. The ability to form a connection between such ends in particular by using a 5'-OH terminus is a unique feature of the inventive HSPC117 molecule.

In general, the RNA ligation can be an inter- or intra-strand ligation. Two separate RNA strands may be connected on the 3' and 5' end, respectively. Furthermore, in an intra-strand ligation, the 5' and 3' end of one RNA molecule is connected.

In a further embodiment of the present invention the RNA is double-stranded. In particular, the first and/or second RNA molecule connected by the inventive RNA ligase may comprise a double-stranded section or is fully double-stranded or alternatively single-stranded. In particular preferred, the 3' end mentioned above as well as the 5' terminus of the other RNA end, which are connected by the RNA ligase reaction, may be double-stranded. Further portions of the RNA can also be single-stranded, in particular of RNA splicing there is usually a single-stranded 3' overhang of a pre-tRNA. Also, the 5' and/or 3' ends, which are connected by the RNA ligase reaction may be single-stranded—as is usually the case in pre-tRNA processing. Double-strandedness may be a base pairing between the first and the second RNA molecules, or alternatively may be base pairing to further RNA strands.

In particular preferred embodiments the present inventive HSPC117 molecule is used for RNA splicing. In an RNA splicing reaction an intron section is removed between two exons, which are connected by the inventive RNA ligase. A typical splicing reaction is the reaction of an exon1-intron-exon2 sequence to exon1-exon2. Other splicing reactions may remove several introns and, optionally also exons between these intron sections.

The RNA that is connected by the inventive use of the HSPC117 molecule as RNA ligase may be of any length. Example RNA lengths are 2 to 3000 nucleotides or base pairs in length. In special embodiments, the first RNA or the second RNA may be more than 1, 2, 3, 4, 5, 6, 7, 8, 9, 10, 15, 20, 25, 30, 40, 45, 50, 60, 70, 80, 90 or more than 100 nucleotides or base pairs in length. Alternatively or in addition thereto, the RNA, either the first RNA or second RNA or both, may be up to 3000, 2000, 1500, 1200, 1000, 900, 800, 700, 600, 500, 400, 300, 200, 100, 80, 70, 60 or up to 50 nucleotides or base pairs in length.

The inventive HSPC117 molecule may be of anyone of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11. The sequences provide example HSPC117 molecules of *H. sapiens, M. musculus, X. leavis, S. purpuratus, D. melanogaster, C. elegans, C. reinhardtii, M. jannaschii, P. horikoshii, T. thermophilus,* or *E. coli*, respectively. Further HSPC117 sequences or sequence variants are disclosed in SEQ ID NOs: 12 to 23, providing further nucleic acid and amino acid sequences from *homo sapiens, C. elegans, Drosophila, Danio rerio*, bovine, mouse and rat. The inventive HSPC117 molecule may be obtained from any of these organisms. In preferred embodiments the inventive HSPC117 molecule is of an animal or archaea, in particular of a mammal, such as a primate, including human, or rodent, in particular mouse or rat.

The inventive HSPC117 molecule may be further modified by one or more amino acid substitution or deletion. Furthermore, the inventive HSPC117 molecule may be expressed as part of a fusion protein and may comprise further additional amino acids or polypeptide sequences. In particular preferred, the inventive HSPC117 molecule has a sequence identity of at least 45%, 50%, 55%, 60%, 65%, 70%, 75%, 80%, 85%, 90% or at least 95% to any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 17, SEQ ID NO: 19, SEQ ID NO: 21, SEQ ID NO: 23. In preferred embodiments the sequence identity is related to SEQ ID NO: 1. Sequence identities are usually calculated over the whole length sequences of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 17, SEQ ID NO: 19, SEQ ID NO: 21, SEQ ID NO: 23. Of course such a HSPC117 molecule variant maintains the RNA ligase activity as mentioned above as can be easily determined by standard assays as shown in the example section herein. In particular of importance is that the HSPC117 molecule maintains catalytically important residues, such as cysteine 122 of SEQ ID NO: 1. Variants of the inventive HSPC117 molecules are e.g. described in US 2007/0204352 A1 (especially SEQ ID NOs: 15, 16, 69, 70, 71, 72, 73, 74, 75, 76, 77, 78 thereof), incorporated herein by reference as SEQ ID NOs: 12 to 23, and can be used for the inventive purposes.

In the case of amino acid substitution, in preferred embodiments at least 50%, at least 60%, at least 70%, at least 80%, at least 90% or at least 95% of the substitutions are conserved amino acid substitutions. Conserved substitutions are mutations within an amino acid group. Amino acids are usually grouped according to their polarity, charge and/or size. The following groups are noteworthy: basic amino acids: arginine, histidine, lysine; acidic amino acids: aspartic acid, glutamic acid; polar amino acids: asparagine, glutamine; small amino acids: alanine, serine, threonine, methionine, glycine; aromatic amino acids: phenylalanine, tryptophan, tyrosine, histidine; hydrophobic amino acids: leucine, isoleucine, valine. Cysteine is a special case, as it may usually be conservatively substituted with serine and any other polar uncharged sidechain and vice versa. Glycine may be used as substituent for any amino acid. Glycin can be substituted usually by a small sidechain such as by alanine, serine, threonine. Proline may be usually substituted, or used as substituent for glycin.

In a further aspect, the present invention relates to the method of ligating at least two RNA molecules—as e.g. described above—comprising using a HSPC117 molecule as described above. Herein, the expressions "use . . . as RNA ligase" and "method of ligating RNA molecules" are used interchangeably.

In preferred embodiments the inventive use or method may comprise contacting at least two RNA molecules with the HSPC117 molecule in a cell. The invention also relates to the use of recombinant HSPC117. Recombinant HSPC117 (including any homologs or orthologs as mentioned above) can be readily obtained by expression of genetic constructs comprising one or more HSPC117 DNA sequences operable linked to regulatory DNA sequences (which may be heterologuous regulatory sequences), such as promoters or enhancers, in host cells. Example host cells are bacterial, archaea, fungal (including yeast), plant or animal (including insect or mammalian) cells. In such constructs, the design of which is described in common laboratory manuals and is routine to a skilled artician, the regulatory sequences may be operably linked to a polynucleotide encoding the HSPC117 molecule or an active variant thereof having RNA ligase activity.

The inventive HSPC117 molecule may be used in vivo such as in a cell, e.g. artificially provided therein or recombinantly expressed in the cell. Two RNA molecules may be ligated in said cell according to an embodiment of the present invention. The cell may be any cell as described above, preferably a non-human cell or an isolated human cell.

In a further embodiment the RNA molecules may be contacted with a HSPC117 molecule in vitro or in situ such as e.g. including outside a cell or in a cell free solution. With the inventive HSPC117 molecule it is possible to ligate RNA molecules in an isolated fashion, ex vivo.

According to the present invention it was found that HSPC117 is the catalytically active protein that may naturally also be contained in a complex in vivo. Therefore, according to a further embodiment of the present invention the inventive HSPC117 molecule is also provided in such a complex. The complex may be e.g. of spliceosomal particles such as SF3B particles that can be isolated from nuclear HeLa cell extracts. Other complex members, in particular with regard to other HSPC117 molecules of other organisms or variants thereof may be isolated from cellular extracts of the respective organisms.

In particular preferred embodiments the inventive complex may comprise DEAD box helicase DDX1, a FAM98B molecule, a CGI-99 molecule, ASW or any combination thereof, in particular preferred a combination of the DDX1 and FAM98B molecule. Further complex members that can be comprised in the complex of HSPC117 molecules may be any one of tables 1 and 2 shown in example 5.

According to the present invention the HSPC117 molecule may be provided per se. Alternatively, HSPC117 molecules may be used or provided as a component of a kit.

Thus, in a further aspect the invention relates to a kit that contains HSPC117 molecule. The kit may further comprise a reaction buffer for the RNA ligase comprising buffer components or one or more metal ions selected from $Mg^{2+}$, $Mn^{2+}$, $Ni^{2+}$ or mixtures thereof. In preferred embodiments the metal ions are included in an amount for use in a final concentration range of ca 0.1-20 mM, preferably 1-10 mM, in particular preferred 2-5 mM.

Besides the above-mentioned metal ions, the buffer of the kit may contain the usual buffer components that are well known in the art. Such buffers may e.g. include phosphate, Hepes, Tris-HCl components. Preferably the buffer is in the range of physiological pH values of e.g. pH 6 to pH 9, preferably pH 7-8, especially preferred about pH 7.4. The buffer may comprise tonic substances or salts ranging from about 10-200 mM KCl or NaCl. Furthermore, the buffer may contain non-ionic tonicity substances such as glycerol.

In the form of a test kit, the kit may further comprise an RNA molecule that is a substrate of the inventive HSPC117 molecule, especially a RNA molecule with a 2',3' cyclic phosphate. This RNA molecule may e.g. further comprise a label such as a radioactive label to detect the RNA molecule before or after the RNA ligase reaction. Such a kit is useful for all types of reactions and to monitor RNA processing or hybridisation. The inventive HSPC117 molecule or kit may be especially used for RNA ligation or splicing studies.

The present invention in a further aspect relates to a transgenic cell comprising an exogenously expressed HSPC117 molecule. The cell may be a cell line or comprised in an animal model, in particular a non-human animal model. A cell line may be also a human cell line that stably expresses HSPC117 molecules.

Stable expression of the exogenously expressed HSPC117 molecule is achieved by inserting a HSPC117 DNA, under the control of a promoter, preferably an inducible promoter, into the cell. In certain embodiments this DNA can be inserted in the genome of the cell, which can be achieved by conventional methods such as commercially available systems like the tetracycline-inducible system such as the t-REx system (invitrogen). Such cells are useful in combination with RNA that can be ligated, especially RNA with 2',3' cyclic phosphate or 5'-OH to ligate the RNA molecules.

The present invention further relates to method of reducing RNA ligase activity, in particular RNA>p ligase activity, in a cell comprising inhibiting a HSPC117 molecule in a cell, preferably by knock-out or RNAi. RNA>p ligase activity, as mentioned above, relates to RNA ligase reactions using 2',3'-cyclic phosphate terminated RNA as substrate. Such a method can be used to reduce tRNA production or processing in said cell. A reduction of HSPC117 can be achieved by administering a ligand to HSPC117 that binds, segregates or generally inactivates HSPC117 in said cell or by inhibiting HSPC117 expression. Such a binding inhibitor is e.g. a HSPC117 antibody, which is e.g. commercially available. A "HSPC117-antibody" includes any functional equivalents and derivatives thereof, including antibody fragments such as Fab, $F(ab)_2$, Fv, or single chain antibodies (scAb) that binds HSPC117. In preferred embodiments the inhibition is achieved by reducing expression of an HSPC117 molecule, preferably an endogenous HSPC117 molecule, in said cell. A suitable inhibitor to reduce HSPC117 expression is a HSPC siRNA molecule to induce RNAi.

Preferred methods of inhibiting HSPC117 expression are knock-out or RNAi. For a knock-out, a genomic HSPC117 is modified to present expression, transcription or translation of a functional HSPC117 molecule. Such modifications may include large stretch deletion of e.g. up to 200 or more nucleotides or selective modifications (deletions or substitutions) in the catalytic centre. E.g. a modification in the catalytic C122 according to the human HSPC117 sequence of SEQ ID NO:1 is sufficient to prevent expression of a functional molecule. Of course the skilled man in the art can readily select alternative modifications, which are within the routine ability of a molecular cell biologist.

A further preferred method is RNAi (RNA interference). For antagonizing cellular HSPC117 expression preferably siRNA molecules are administered to reduce the expression and function. RNA interference is a mechanism to suppress gene expression in a sequence specific manner. RNA interference is highly effective methodology for suppression of specific gene function in eukaryotic cells. When applied to cells and organisms, RNAi entails the degradation of target mRNA upon transfection of short interfering RNA (siRNA) oligos or short-hairpin RNA (siRNA) encoding vectors. Various methods of RNAi have been described and are generally known for altering gene expression in plant cells, *drosophila* and human melanoma cells as is described for example in US 2002/0162126 and US 2002/0173478. The siRNA for use in the methods and compositions of the invention are selected to target a HSPC117 molecule. In this manner they are targeted to various RNAs or portions thereof corresponding to the HSPC117 gene. It is understood by one of skill in the art that the siRNA as herein described may also include altered siRNA that is a hybrid DNA/RNA construct or any equivalent thereof, double-stranded RNA, microRNA (miRNA), as well as siRNA forms such as siRNA duplications, small hairpin RNA (shRNA) in viral and non-viral vectors and siRNA or shRNA in carriers.

In a further embodiment the invention relates to a HSPC117 knock-out cell or cell with reduced or inhibited endogenous HSPC117 expression.

Such cell lines can be further used in RNA ligation or splicing studies, i.e. to study the function of RNA ligation. Reduction of an endogenous HSPC117 expression has also the benefit that there is no background activity of the inventive HSPC117 ligase that mediates the conversion of 2',3' cyclic phosphate onto 5'-OH RNA molecules. In combination with a transgenic cell wherein HSPC117 is under control of an inducible promoter this allows specific on/off studies of the RNA ligase and is a useful tool to control the ligase activity, be it only for splicing studies or as a cellular biochemical engineering tool. Therefore, in a preferred embodiment, the invention relates to a HSPC117 knock-out cell that does not express endogenous HSPC117 but is in addition exogenously transfected with an HSPC117 molecule under control of an inducible promoter. In preferred embodiments the cell is a mammal cell, especially preferred a cell of a primate, in particular of a human or of a rodent such as a mouse cell. These cells, including cells with increased or decreased HSPC117 expression as described above, can be used for RNA ligation or splicing studies.

In a further aspect the present invention relates to the treatment of diseases with abnormal tRNA processing or diseases dependent on (increased) tRNA processing. In particular embodiments the invention provides the use of a HSPC117 molecule as an RNA ligase or a method of inhibiting a HSPC117 molecule, with the proviso that methods for treatment of the human or animal body by therapy are excluded, or the use of a HSPC117 molecule or HSPC117 inhibitor for use as medicament. A HSPC117 inhibitor is any molecule that reduces HSPC117 activity or expression as described above, preferably a HSPC117 antibody or HSPC117 siRNA.

HSPC117 molecule inhibition may have therapeutic effect in several diseases. Such diseases include proliferative diseases, in particular cancer. By reducing tRNA processing the proliferative activity can be greatly decreased resulting in reduced cell growth. Therefore the present invention provides a method of reducing tumor cell growth comprising administering an HSPC117 molecule inhibitor to said cell. It is known that tumor cells have abnormally high rates of Polymerase (Pol) III transcription (Marshall & White, 2008). Since Pol III synthesizes tRNAs, targeting the tRNA ligase will turn (high) tRNA production rate-limiting in cancer cells. The importance of tRNA splicing components for proliferation is e.g. disclosed in the WO2004/087884 A2 (incorporated herein by reference).

In a further aspect the present invention provides the treatment of or a disease or infection dependent on host polymerases, such as hepatitis delta virus infection comprising administering an HSPC117 molecule inhibitor to said cell. The human hepatitis delta virus is the only animal virus known to replicate its RNA genome using a host polymerase. Host factors involved in the replication of the virus are elusive. A ligase-host factor in circularizing the viral genome during replication is implicated (Reid & Lazinski, 2000). In a combined proteomic-RNAi screen identified more than 100 proteins associated to the hepatitis delta antigens. A portion of the identified proteins has roles in RNA metabolism, and one of those is HSPC117. Combined this shows that HSPC117 is a decisive target for treating a hepatitis delta virus infection.

Furthermore the present invention relates to a method of treating a disease in a subject associated with dysfunctional tRNA splicing, in particular being deficient in a tRNA ligation by RNA>p, preferably pontocerebellar hypoplasia, comprising administering a HSPC117 molecule to said subject. A link has been established between the tRNA splicing pathway and Pontocerebellar hypoplasia. This disease belongs to a group of degenerative autosomal recessive disorders with prenatal onset, atrophy or hypoplasia of the cerebellum and other motor impairments. Mechanistically these diseases are associated with aberrant removal of introns and ligation of exons during tRNA splicing. Therefore administration of a functional HSPC117 molecule can restore normal splicing and intron removal and treat the disease, while it is also well known, but not understood at a molecular level, that tRNA metabolism has a special impact on brain function.

Cells respond to oxidative stress by secreting Angiogenin, a factor that displays ribonuclease activity besides its known role in angiogenesis. Angiogenin cleaves mature tRNAs at the anticodon loop, thereby generating tRNA pieces known as tiRNAs, for tRNA-derived stress-induced RNAs. tiRNA accumulation impairs protein synthesis and is therefore detrimental to cell health and function. Inactivating the human tRNA ligase HSPC117 leads to an increase in tiRNAs in culture cells. Increased HSPC117 reverts Angiogenin cleavage and reduces tiRNA levels. HSPC117 therefore may have a distinct role in re-ligating Angiogen-incleaved tRNA. This angiogenin reaction cannot be reverted upon inhibition of HSPC117 molecule. Thus, the present invention also relates to a method of modulating tiRNA amounts in a cell, such as by increasing or decreasing HSPC117 activity in a cell.

In a further aspect, the present invention provides a pharmaceutical composition comprising a HSPC117 molecule expressing nucleic acid, preferably in form of a expression vector, or a HSPC117 molecule inhibitor, preferably an antibody or siRNA or variant thereof as described above. Such a composition can be a ready to use composition, e.g. for the treatment of any disease described above. Pharmaceutical compositions or formulations for therapeutic or prophylactic use may comprise a pharmaceutically acceptable diluent, carrier, solubilizer, emulsifier and/or preservative. The invention also provides for pharmaceutical compositions comprising a therapeutically effective amount of an HSPC117 inhibitor or expression nucleic acid. The term "therapeutically effective amount" means an amount which provides a therapeutic effect for a specified condition and route of administration. The composition may be in a liquid or lyophilized form and comprises a diluent (Tris, acetate or phosphate buffers) having various pH values and ionic strengths, solubilizer such as Tween or Polysorbate, carriers such as human serum albumin or gelatin, preservatives such as thimerosal or benzyl alcohol, and antioxidants such as ascrobic acid or sodium metabisulfite. Selection of a particular composition will depend upon a number of factors, including the condition being treated, the route of administration and the pharmacokinetic parameters desired. Nucleic acids and siRNA formulations are preferably administered in liposome formulations. Compositions of the invention may be administered by injection, either subcutaneous, intravenous or intramuscular, or by oral, nasal, pulmonary or rectal administration. The route of administration eventually chosen will depend upon a number of factors and may be ascertained by one skilled in the art.

The present invention will be now explained more in detail with reference to the figures and examples, without being limited thereto.

FIGURES

FIG. 1. RNA ligation mechanisms and identification of the RNA>p ligase HSPC117. (A) Scheme illustrating mechanistic differences in described RNA ligation pathways (B) [5'-$^{32}$P]-pCp-radiolabeled 5'-OH, 3'-P RNA oligonucleotides (depicted in grey, asterisk marks position of radiolabel) were incubated with or without AP and annealed to RNA strands (depicted in black) incubated with or without T4 Pnk in presence of ATP. The obtained RNA duplexes were used as substrates for inter-strand ligation in HeLa cell extracts. Aliquots of ligation reactions were withdrawn at indicated time points and analyzed by denaturing gel electrophoresis. (C) Fractionation scheme established for partial purification of RNA>p ligase from HeLa extracts. Throughout the purification inter-strand ligation of [5'-$^{32}$P]-pCp radiolabeled 5'-OH, 3'-P dsRNA was used to monitor RNA>p ligase activity. (D) Dilution series of protein extracts prepared from HSPC117-siRNA-transfected cells and control-siRNA-transfected cells were assayed for inter-strand ligation. Numbers above lanes indicate extract dilution. (E) The same extracts were assayed for processing of [α-$^{32}$P]-GTP-radiolabeled pre-tRNA in time course experiments. (F) Reduction of HSPC117 levels in extracts was confirmed by Western Blot.

FIG. 2. Affinity purification of c-myc-HSPC117 from stably transfected HeLa cell lines yields an RNA>p ligase complex. (A) IPs of WT or C122A c-myc-HSPC117 were incubated with [α-$^{32}$P]-GTP-radiolabeled tRNA exon halves. An IP prepared from a non-expressing clone were used as negative control. (B) Specificity of the affinity purification and presence of equal amounts of WT and mutant c-myc-HSPC117 in compared IPs was confirmed by Western blot.

(C) tRNA exon halves were incubated with Clp1 or T4 Pnk in presence or absence of ATP. RNA was recovered and used as a substrate in incubations with immunopurified c-myc-HSPC117. (D) Scheme illustrating the course of procedures used for nearest neighbor analysis of splice junctions in mature tRNA and circular intron (Np, nucleoside 3'-monophosphate; pN, nucleoside 5'-monophosphate). (E) RNAse T1 fragments derived from [α-$^{32}$P]-UTP-radiolabeled mature tRNA generated either by T4 Pnk/Rnl1 or affinity purified c-myc-HSPC117 were resolved by denaturing gel electrophoresis. 6-mers, 7-mers and 8-mers were isolated from the gel, digested by RNAse T2 and analyzed by TLC in solvent D. (F) Circular, [α-$^{32}$P]-ATP-radiolabeled intron generated either by T4 Pnk/Rnl1 or affinity purified c-myc-HSPC117 was isolated from gels, digested with RNAse P1 and analyzed by TLC in solvent C.

FIG. 3. Active RNA>p ligase complex co-purifies with SF3B complexes. (A) Affinity protocol established for purification of SF3B-complexes from HeLa nuclear extracts. After depletion of U2 by immobilized monoclonal antibody H20 recognizing the trimethylguanosine ($m_3^{2,2,7}$G) mRNA cap structure, HSPC117- and SF3B-complexes were bound by immobilized monoclonal SF3B155-directed antibody 13E12. (B) Upon elution from the anti-SF3B155 13E12 column, SF3B and RNA>p ligase complexes were separated by size exclusion on Superose 6. Fractions were analyzed by SDS-PAGE and proteins stained with Coomassie blue. (C) Fractions eluted from the Superose 6 column were assayed for RNA>p ligase activity using tRNA exon halves as substrate. RNA recovered from reactions was analyzed by denaturing gel electrophoresis. (D) The RNA>p ligase peak fraction was analyzed by SDS-PAGE, protein bands were visualized by staining with Coomassie blue. Marked bands were identified by mass spectrometry. (E) Loss of inter-strand ligation and tRNA maturation activities upon silencing of HSPC117 but not the other components of RNA>p ligase complex. Cells were treated with siRNAs targeting C22ORF28/HSPC117, DDX1, C14ORF166/CGI-99, FAM98B, C20ORF49/ASW and EGFP as a control. Extracts were prepared from these cells and assayed for inter-strand ligation of [5'-$^{32}$P]-pCp-radiolabeled dsRNA or (F) processing of [α-$^{32}$P]-GTP-radiolabeled pre-tRNA. (G) Efficient depletion of C22ORF28/HSPC117, DDX1, C14ORF166/CGI-99, FAM98B and C20ORF49/ASW mRNAs was confirmed by quantitative PCR. Results represent mean and standard deviation of triplicate PCR reactions. (H) Western blot for HSPC117, DDX1, FAM98B and 13-Actin as a loading control confirms efficient depletion of individual RNA>p complex members.

FIG. 4. Silencing of HSPC117 abolishes inter-strand ligation in living HeLa cells and partially impairs tRNA processing in vivo. (A) [5'-$^{32}$P]-pCp-radiolabeled dsRNA were transfected into HeLa cells pre-transfected with siRNAs targeting EGFP as a control gene, HSPC117 or RTCD1. Transfections were stopped at indicated time points. RNA was isolated and analyzed by denaturing gel electrophoresis. (B) Treatment scheme used for transfection of siRNAs and reporter constructs and induction of tagged tRNA transcription. (C) Schematic representation of elements present in tagged tRNA reporter constructs. (D) Tet-repressor expressing HeLa cells were cotransfected with siRNAs targeting the control gene EGFP, HSPC117 or TSEN2 and with the reporter construct pSTet-Ile expressing tagged pre-tRNA Ile. After induction, RNA was isolated at indicated time points and analyzed by Northern blot. (E) Quantification of multiple Northern blot experiments. Transfection of siRNAs and reporter construct were done in triplicates. RNA was recovered from cells, mature tRNA detected by Northern blot and quantitated by Phosphorimaging using ImageQuant. Error bars represent standard deviations.

Figure 5A:
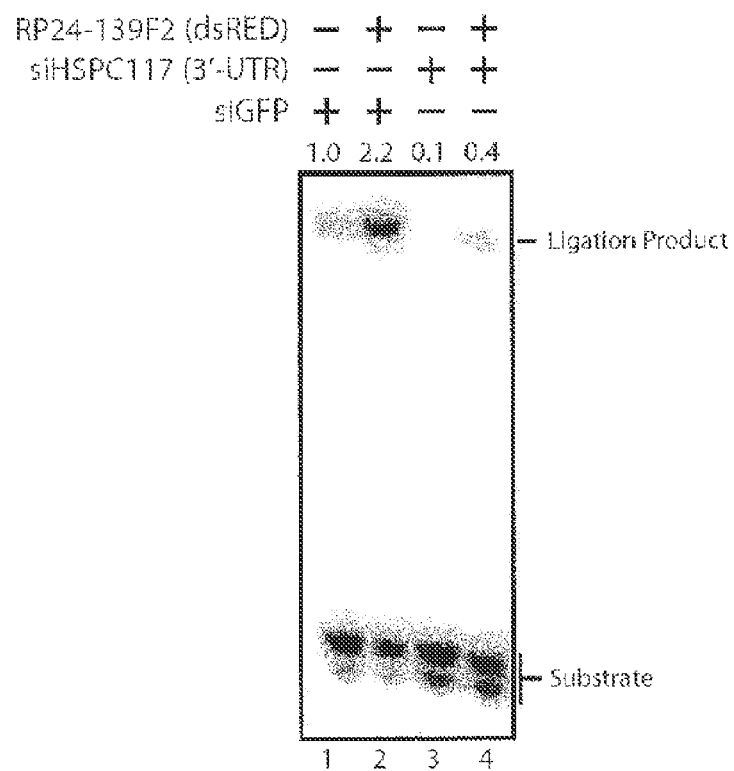
Figure 5B:
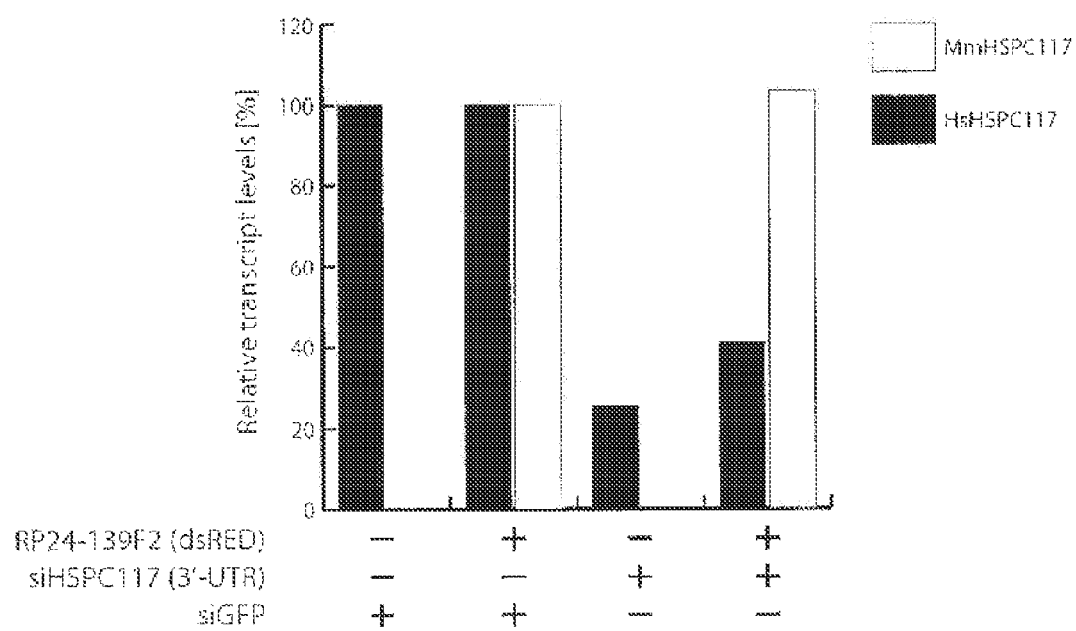

FIG. 5. Genetic rescue of the in vitro RNA ligation defect in extracts depleted of HSPC117 by RNAi. (A) Stable mouse-BAC transgenic HeLa cell pools or wild type HeLa cells were transfected with siRNA targeting the non-conserved 3'-UTR of human HSPC117 or control siRNAs. Extracts prepared from these cells were assayed for inter-strand ligation with [5'-$^{32}$P]-pCp-radiolabeled dsRNA. Numbers above lanes indicate relative amounts of ligation product. The signal in lane 1 was arbitrarily set to 1.0. (B) RNA was isolated from the same experiments in parallel and analyzed for levels of mouse and human HSPC117 by quantitative PCR. Expression levels of human HSPC117 in HeLa cells and human and murine HSPC117 in mouse-BAC transgenic HeLa cell pools were arbitrarily set to 100%.

Figure 6:
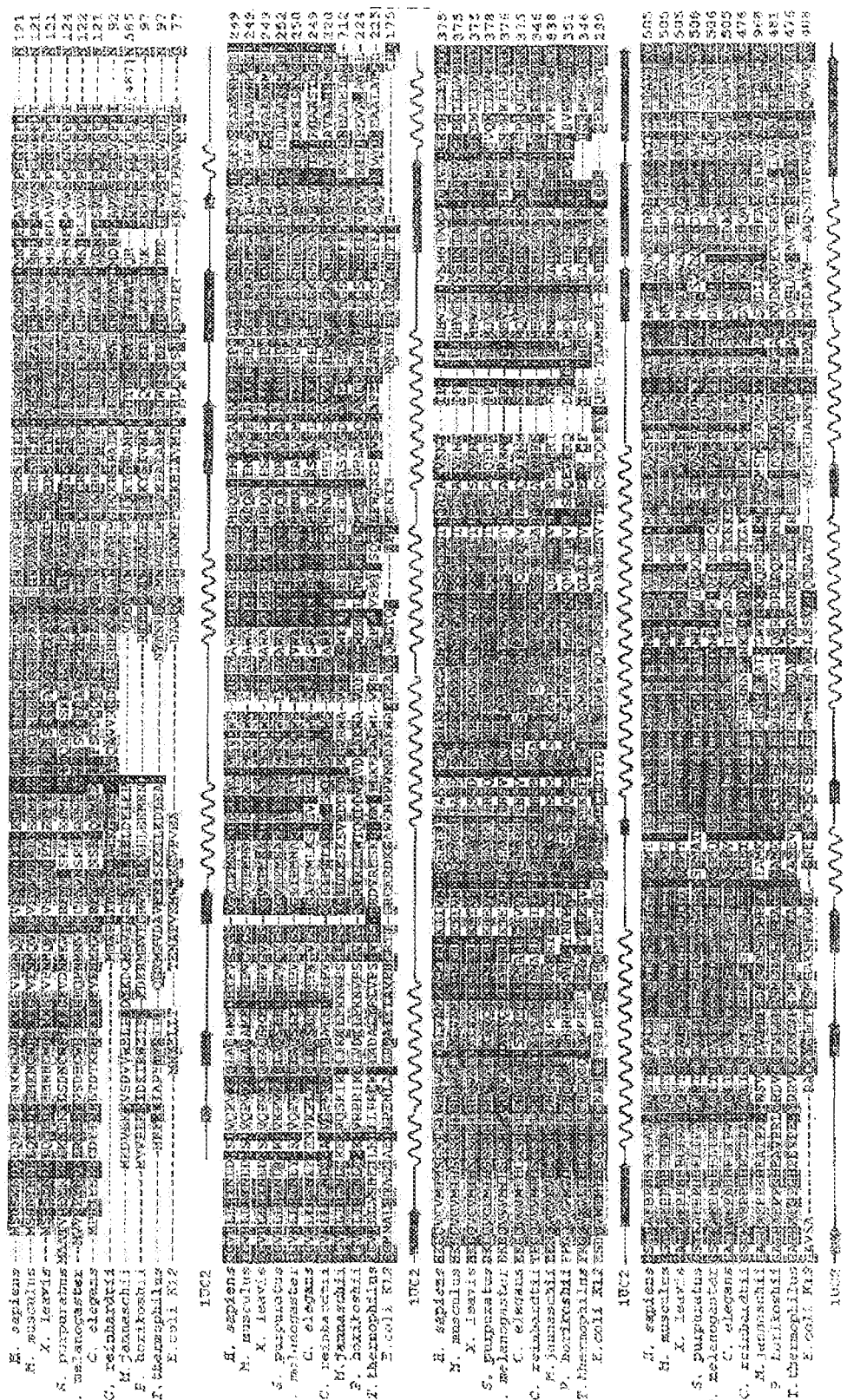

FIG. 6. Sequence alignment of HSPC117/RtcB proteins. HSPC117/RtcB proteins are widely spread in archaea, bacteria and animals, but not in plants and fungi. The asterisk indicates the position of the characterized C122A mutation in the presumed active site of human/murine HSPC117. The following sequence identifiers are used: *H. sapiens*: SEQ ID NO: 1, *M. musculus*: SEQ ID NO: 2, *X. leavis*: SEQ ID NO: 3, *S. purpuratus*: SEQ ID NO: 4, *D. melanogaster*: SEQ ID NO: 5, *C. elegans*: SEQ ID NO: 6, *C. reinhardtii*: SEQ ID NO: 7, *M. jannaschii*: SEQ ID NO: 8, *P. horikoshii*: SEQ ID NO: 9, *T. thermophilus*: SEQ ID NO: 10, *E. coli*: SEQ ID NO: 11.

Figure 7A:
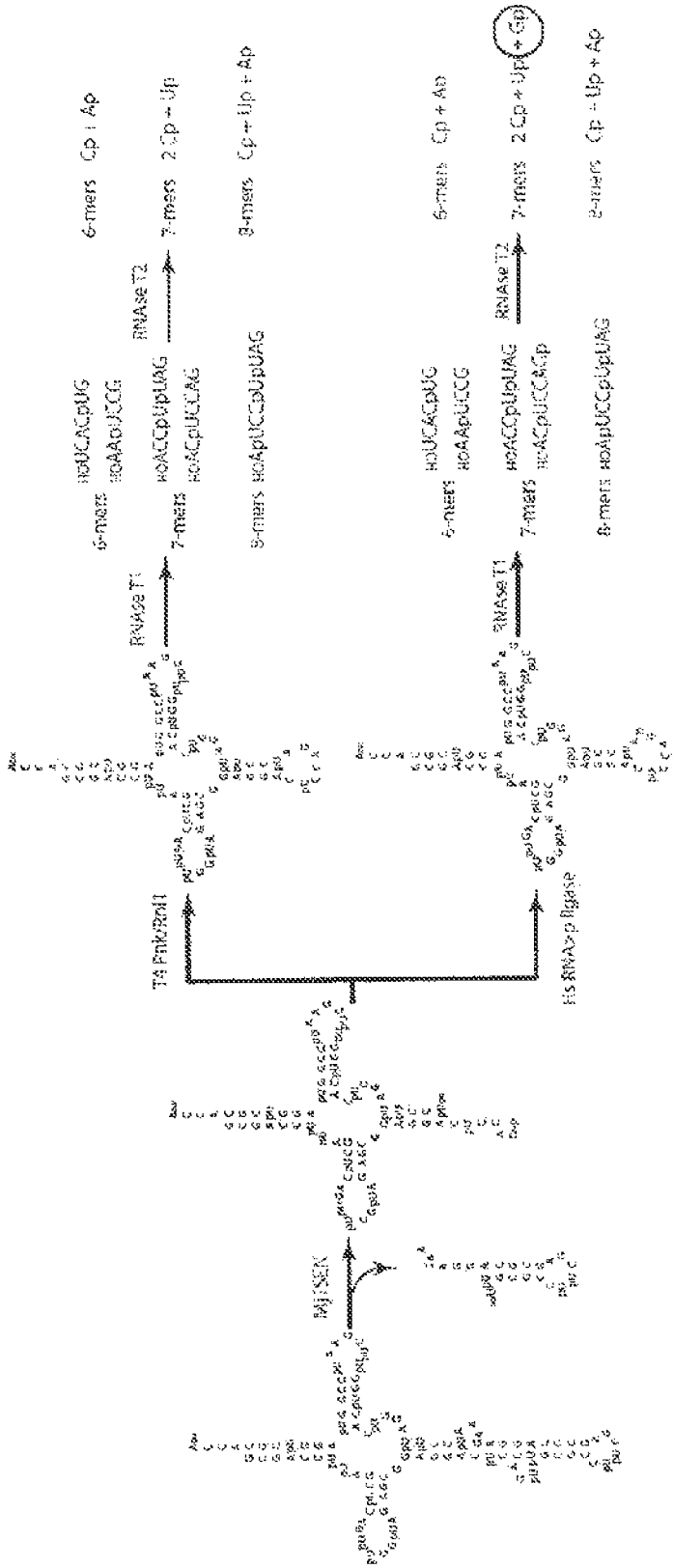

FIG. 7. Detailed explanation of the protocol used for nearest neighbor analysis of the splice junction phosphate. (A) The depicted pre-tRNA is body-labeled with [α-$^{32}$P]-UTP. For simplicity only radiolabeled phosphates are shown. Cleavage of this pre-tRNA with recombinant splicing endonuclease of *Methanocaldococcus jannaschii* (MjTSEN) yields 5'-exon halves with a radiolabeled terminal 2',3'-cyclic phosphate. Ligation of the exon halves with c-myc-HSPC117 leads to formation of mature tRNA molecules containing the precursor-derived splice junction phosphate. During ligation of the same exon halves with a mixture of T4 Pnk and T4 Rnl1 the splice junction phosphate is replaced by exogenous phosphate provided by nucleoside triphosphate. As a consequence, the radioactive splice junction label is lost. Mature tRNA is isolated from both ligation reactions and digested with RNAse T1. The splice junction is now contained in a RNAse T1 7-mer which can be isolated by preparative denaturing gel electrophoresis. Complete digestion of the RNAse T1 7-mers with RNAse T2 releases the splice junction phosphate as a Guanosine 3'-monophosphate (Gp). Therefore, detection of radiolabeled Gp indicates incorporation of the precursor-derived, radiolabeled terminal 2',3'-cyclic phosphate into the splice junction as a 3',5'-phosphodiester. (B) The depicted pre-tRNA is body-labeled with [α-$^{32}$P]-ATP. Cleavage of this precursor produces linear intron with a radiolabeled terminal 2',3'-cyclic phosphate. Ligation of this linear intron with c-myc-HSPC117 yields circularized intron containing the radiolabeled terminal phosphate. During ligation of linear intron with T4 Pnk and Rnl1 this phosphate is removed and an exogenous phosphate provided by nucleoside triphosphate is deposited at the 5'-OH of the first Uridine nucleotide of the linear intron. Circularized intron is isolated by preparative denaturing gel electrophoresis. During ligation with c-myc-HSPC117 the radiolabeled 2',3'-cyclic phosphate becomes the 5'-phosphate of the first Uridine nucleotide of the linear intron. Digestion of circularized intron with RNAse P1 therefore releases the junction phosphate as Uridine 5'-monophosphate (pU). Therefore, detection of radiolabeled pU indicates incorporation of the radiolabeled terminal 2',3'-cyclic phosphate of the linear intron into circular intron as a 3',5'-phosphodiester.

Figure 8:
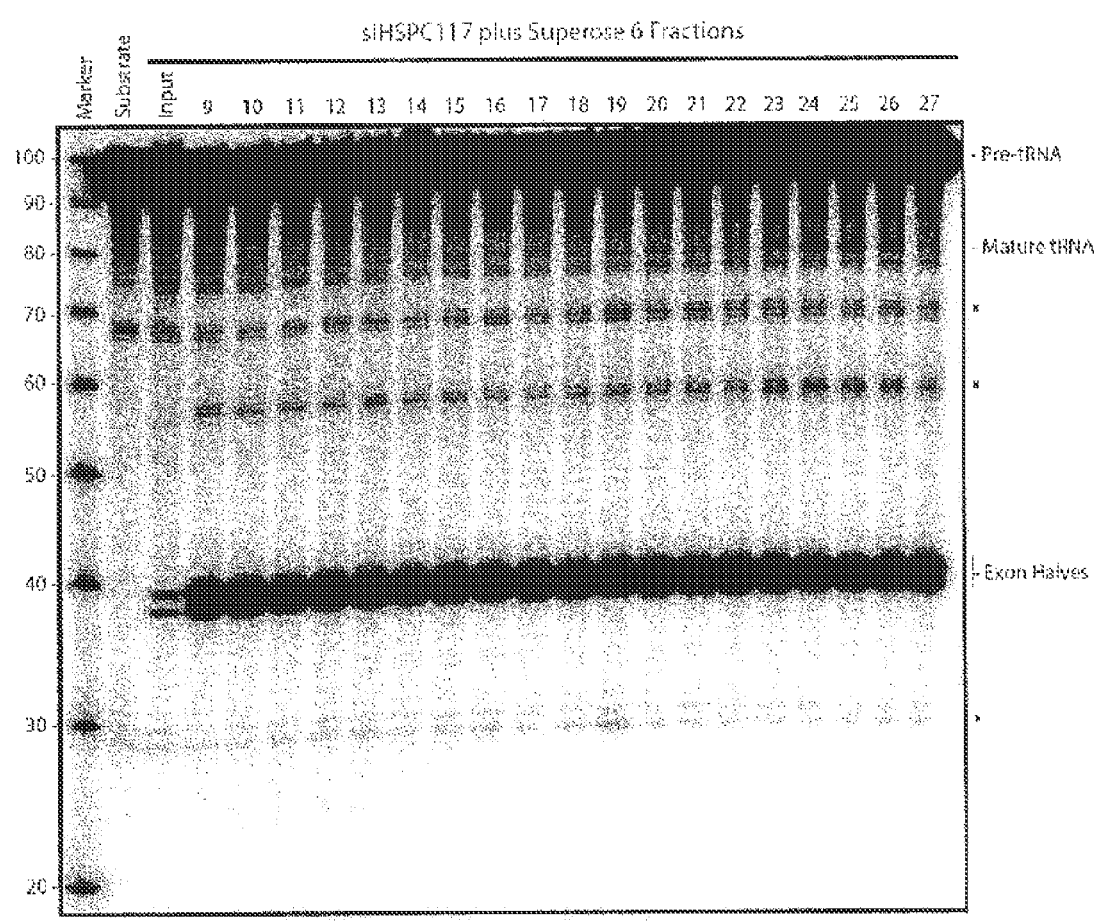

FIG. 8. Biochemical rescue of the in vitro RNA ligation defect in extracts depleted of HSPC117 by RNAi. Extracts of cells depleted of HSPC117 by RNAi were complemented by Superose 6 fractions of HSPC117-complex copurified with SF3B particles. Fractions were assayed for processing of [$\alpha$-$^{32}$P]-GTP-radiolabeled pre-tRNA.

Figure 9A:
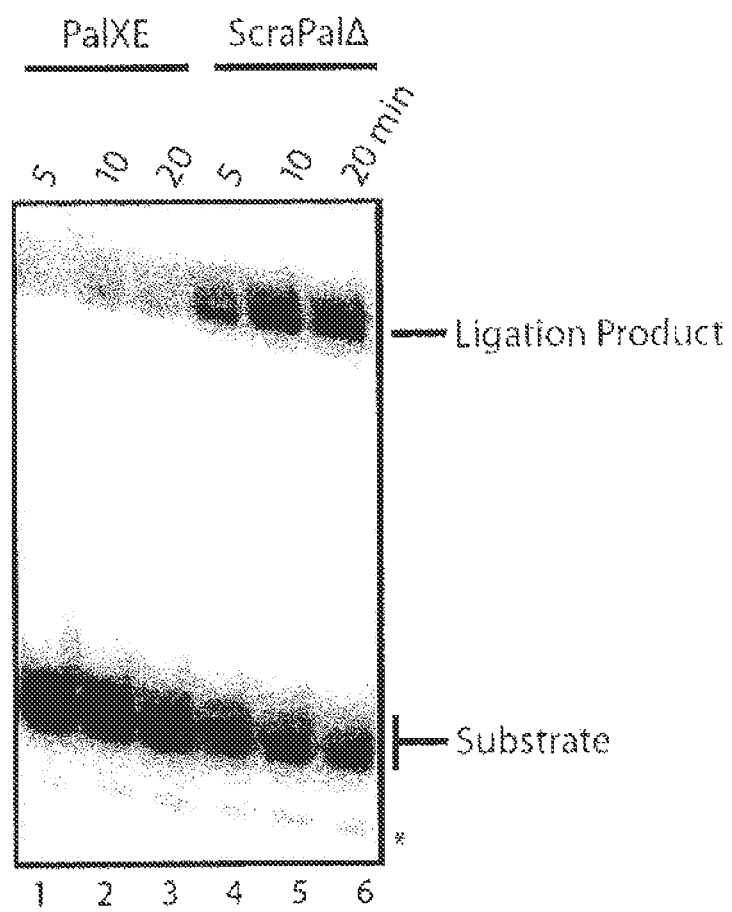
Figure 9B:
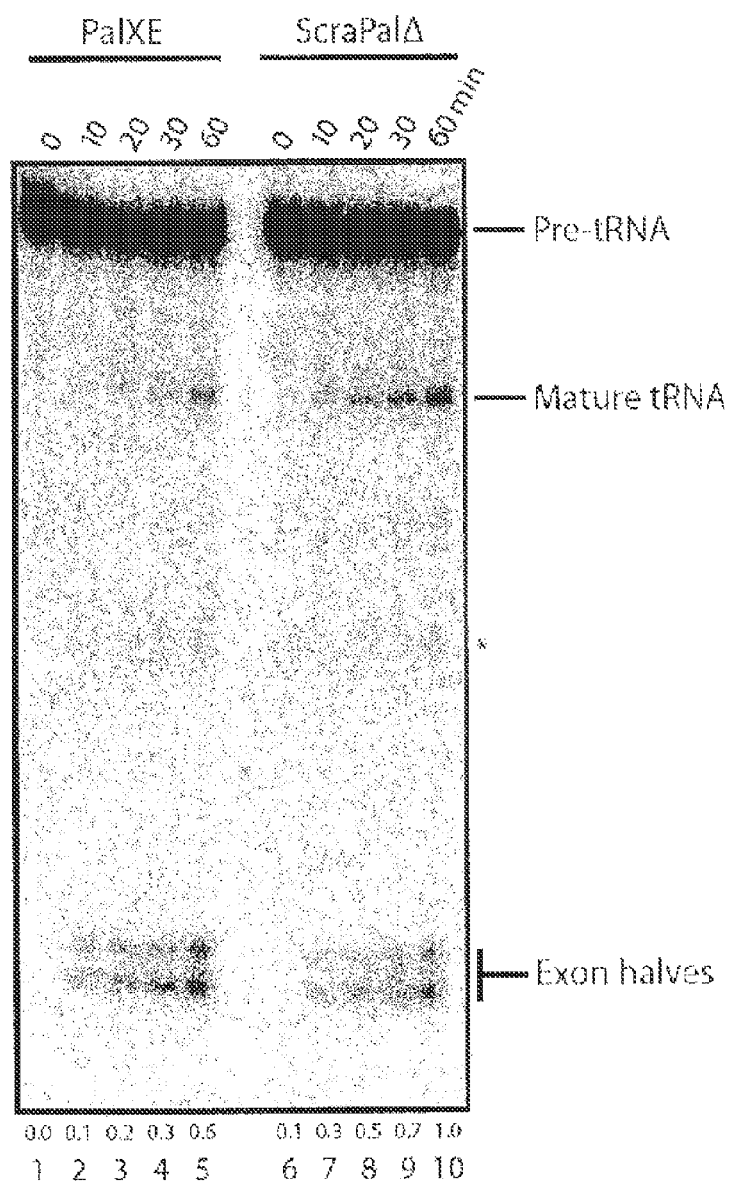

FIG. 9. Interfering with RNA>p ligase by specific inhibition with cruciform DNA. (A) [5'-$^{32}$P]-pCp-radiolabeled dsRNA was incubated with HeLa cell extracts in presence of a 2000-fold molar excess of cruciform (ScraPal) or control DNA (ScraPal$\Delta$) duplexes over dsRNA substrate. Aliquots of reactions were withdrawn at indicated time points and analyzed by denaturing gel electrophoresis. (B) HeLa extracts were assayed for processing of [$\alpha$-$^{32}$P]-GTP-radiolabeled pre-tRNA in presence of a 2000-fold molar excess of cruciform or control DNA duplexes over RNA substrate. Aliquots of reactions were withdrawn at indicated time points and analyzed by denaturing gel electrophoresis.

Figure 10:
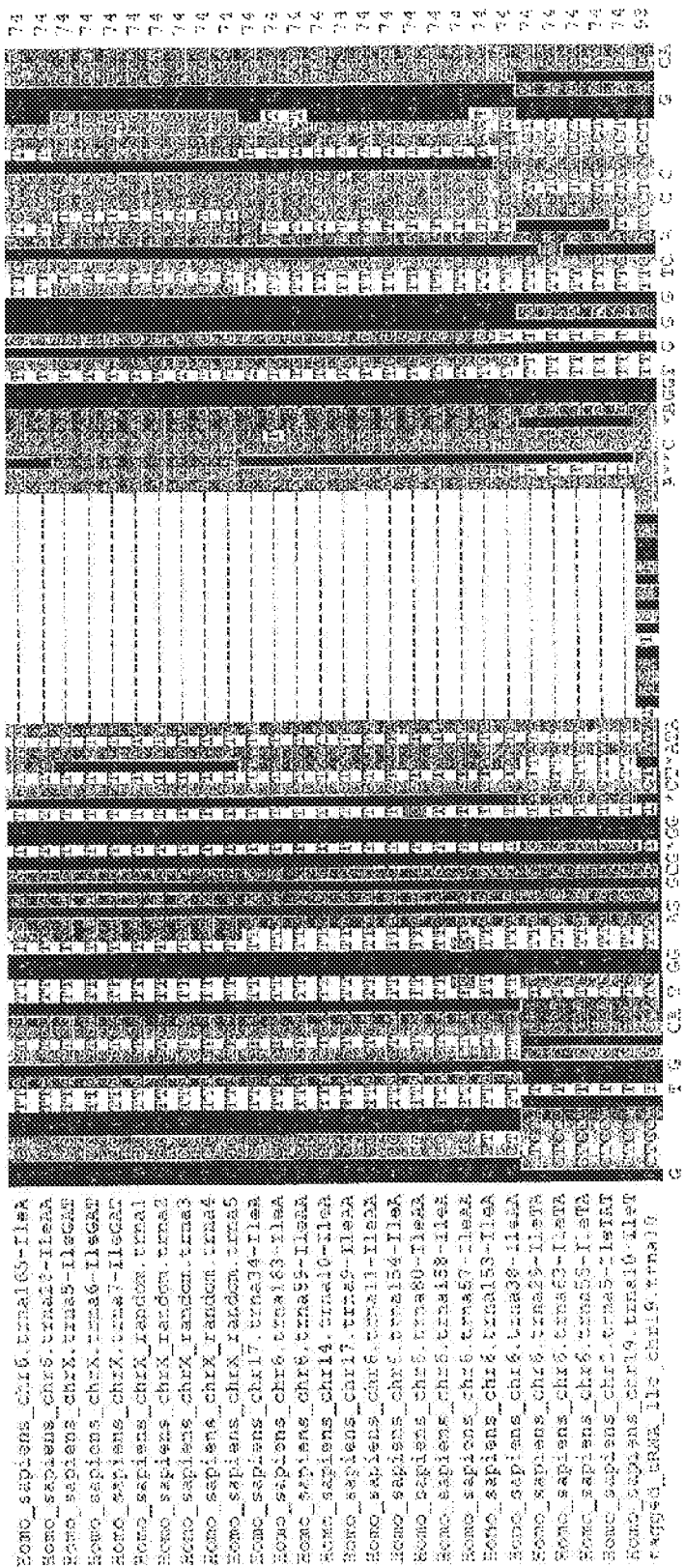

FIG. 10. Design of tagged tRNA Ile and validation of RNAi-mediated depletion of HSPC117 and TSEN2 for in vivo tRNA processing experiments. Alignment of the pSTet insert encoding tagged pre-tRNA Ile$^{TAT}$ with exon sequences derived from annotated human genomic tRNA Ile loci (Chan and Lowe, 2009). Capital letters in the bottom line indicate universally conserved residues, asterisks indicate mutated positions with respect to chr19/trna10-Ile$^{TAT}$.

EXAMPLES

Example 1

Identification of Mammalian RNA>p Ligase by a New Biochemical Strategy

Figure 1B:
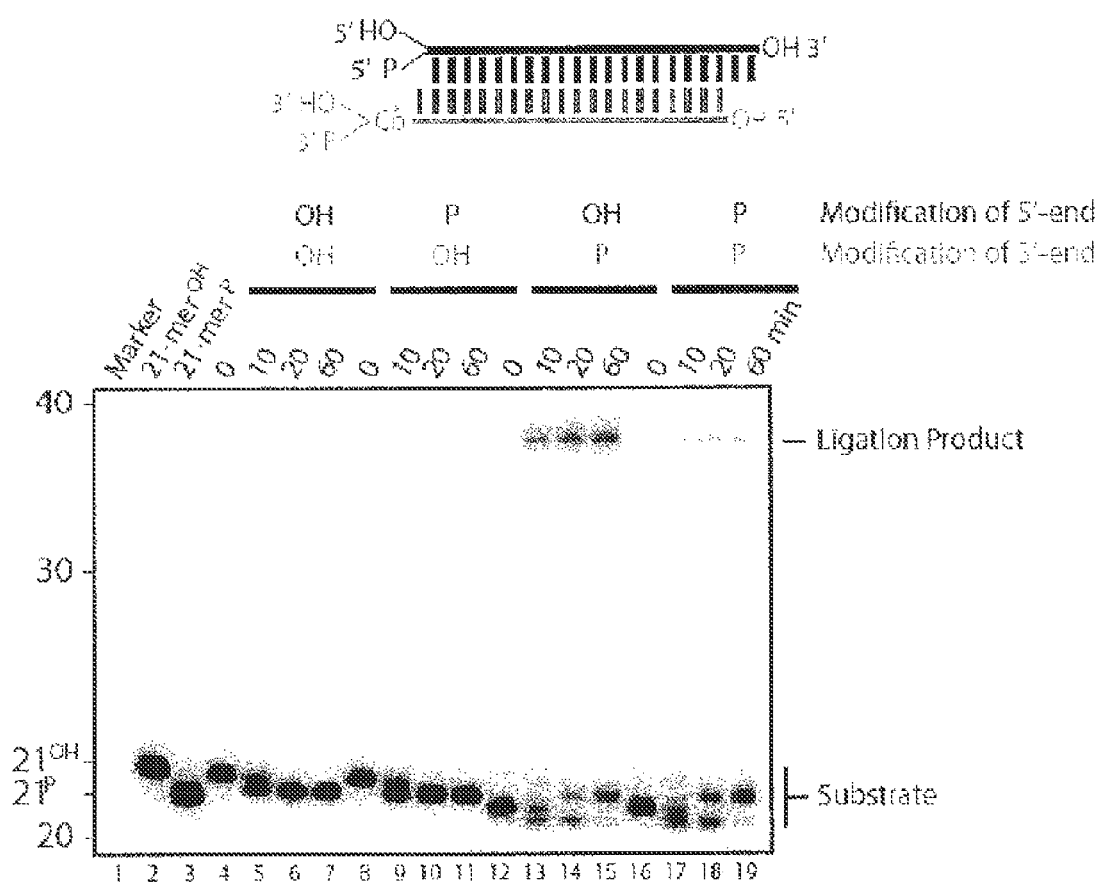
Figure 1C:
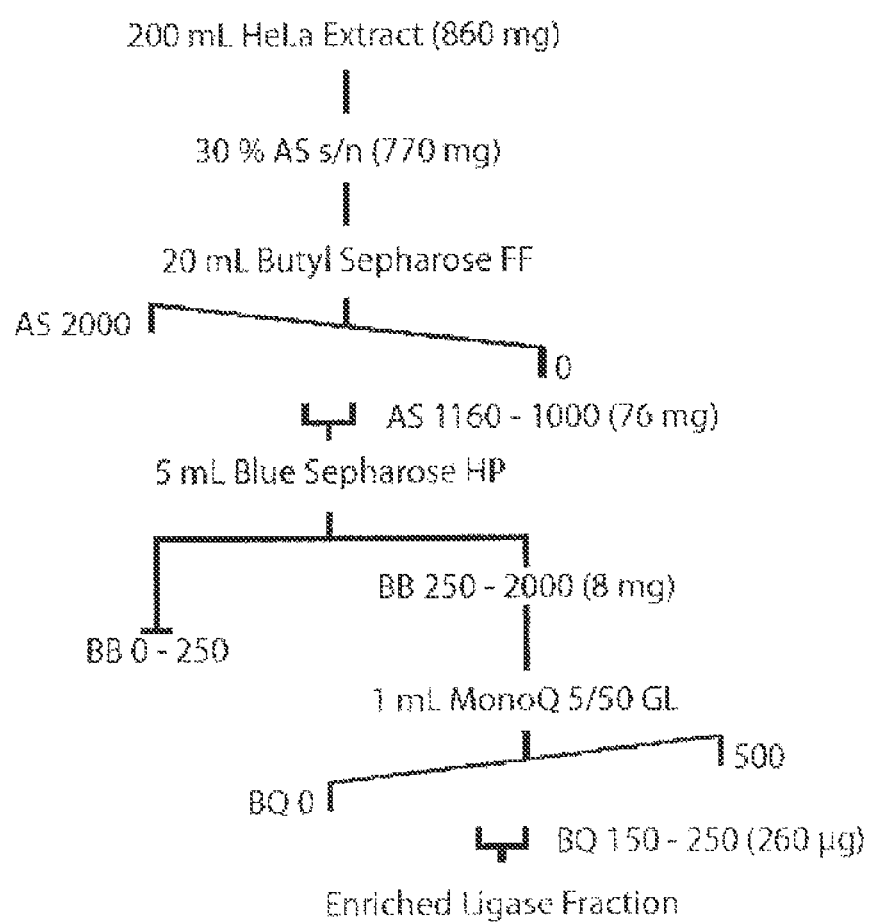

A novel strategy to detect RNA>p ligase as applied potentially leading to the identification of a tRNA ligase. It was serendipitously discovered that 3'-phosphorylated (3'-P), 5'-OH double stranded RNA molecules (dsRNA) are covalently linked upon incubation with human cell extracts. In these extracts, 3'-P dsRNA is converted into 2',3'-cyclic phosphate terminated dsRNA by human RNA terminal cyclase RTCD1. Therefore, we decided to use 3'-P dsRNA as a stable surrogate substrate for the elusive tRNA ligase. Inter-strand ligation requires a 3'-P single stranded RNA annealed to a 5'-OH complementary strand. Removal of the 3'-P by incubation with alkaline phosphatase (AP) or phosphorylation of the 5'-OH by incubation with bacteriophage T4 polynucleotide kinase (T4 Pnk) in presence of ATP or a combination of both inhibited inter-strand ligation (FIG. 1B). This result led to identify RNA>p ligase by classical activity guided protein chromatography. Monitoring inter-strand ligation, we were able to follow RNA>p ligase activity through four purification steps (FIG. 1C). Unable to further fractionate inter-strand ligation activity, we identified proteins contained in the most enriched MonoQ fraction by in solution tryptic digest followed by tandem mass spectrometric analysis (MS). One out of 91 (Tab. S1) identified polypeptides, HSPC117/C220RF28, appeared to be of particular interest for the following reasons. First, HSPC117 is the human homolog of the bacterial/archaeal RtcB gene family characterized by a highly conserved domain of unknown function (UPF0027) and a unique protein fold harboring a putative metal ion binding site. Interestingly, in *E. coli* RtcB together with RtcA, the RNA 3'-P terminal cyclase, resides within a $\sigma$54-regulated operon (Genschik et al., 1998). As a consequence, RtcB/HSPC117 proteins have previously been predicted to have a function in RNA processing or modification (Galperin and Koonin, 2004). Second, UPF0027 proteins form a cluster of orthologous genes (KOG3833) with no detectable representatives in the plant and fungal model organisms *Arabidopsis thaliana*, *Saccharomyces cerevisiae* and *Schizosaccharomyces pombe*. This phyletic distribution is highly reminiscent of the exclusive occurrence of RNA>p ligase activity in animals and archaea (Abelson et al., 1998).

Example 2

HSPC117 is Required for Inter-Strand Ligation and tRNA Maturation

Figure 1D:
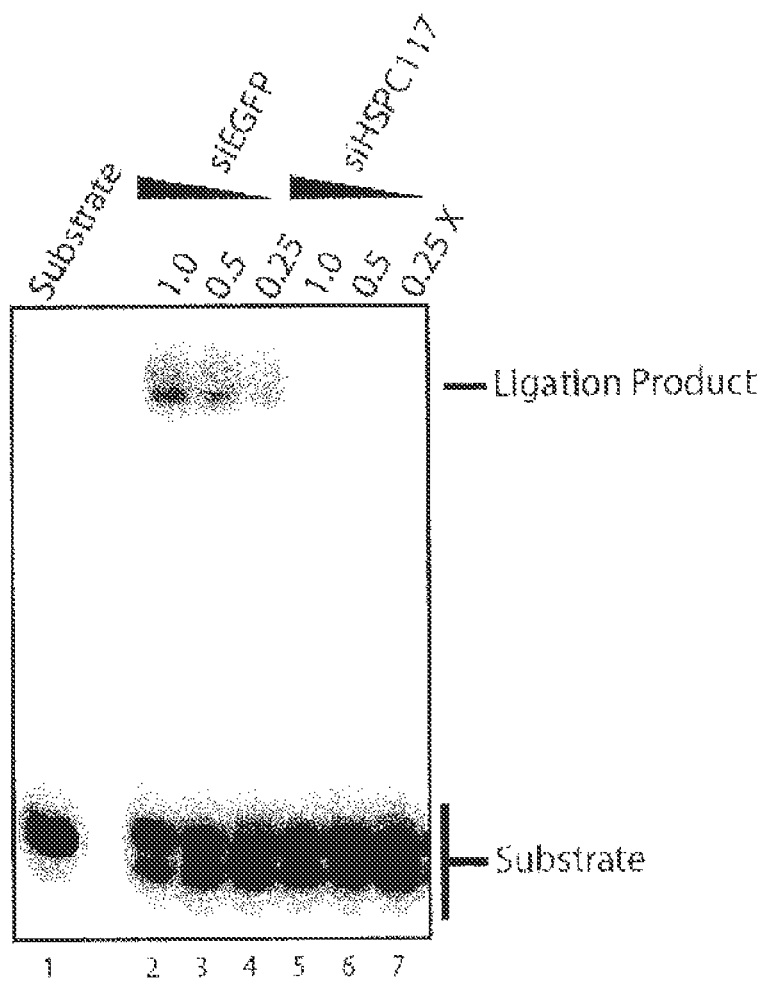
Figure 1E:
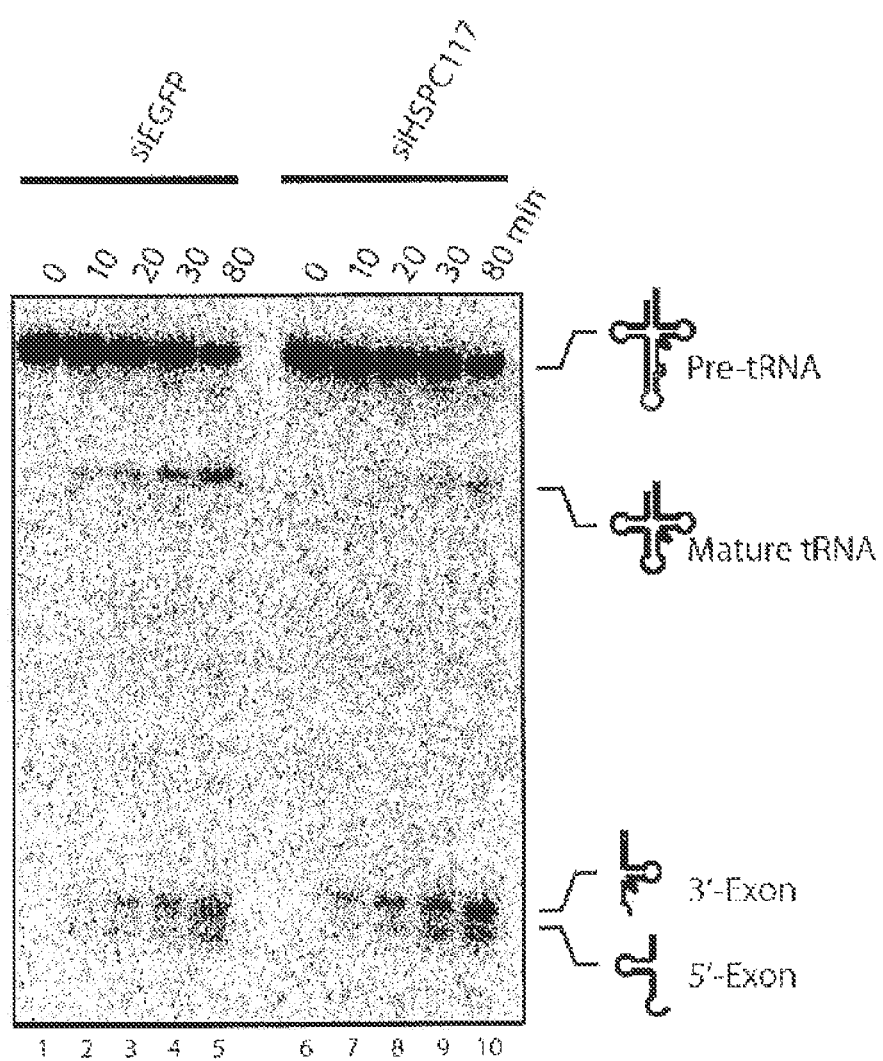
Figure 1F:
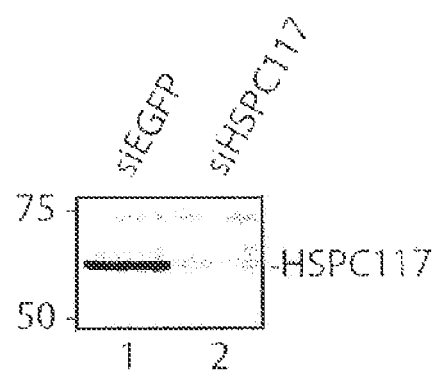

Therefore it was tested whether HSPC117 is indeed involved in inter-strand ligation and tRNA processing. HeLa cells were transfected with small interfering RNAs (siRNAs) targeting HSPC117 or EGFP as a control. Extracts were prepared from these cells and assayed for inter-strand ligation. Remarkably, depletion of HSPC117 by RNA interference (RNAi) affected inter-strand ligation (FIG. 1D, compare lanes 2-4 with lanes 5-7). 3'-P dsRNAs were merely used as surrogate substrates and RNA>p ligation is assumed to be required for splicing of tRNAs. Next, the impact of silencing HSPC117 on tRNA maturation was examined in vitro. Suitable tRNA precursor (pre-tRNA) transcripts are processed to mature tRNA in HeLa cytoplasmic extracts (Laski et al., 1983). Therefore, [$\alpha$-$^{32}$P]-GTP-radiolabeled pre-tRNA transcripts were included with extracts depleted of HSPC117 by RNAi (FIG. 1E). Reduced levels of HSPC117 impaired formation of mature tRNA and led to a concomitant accumulation of exon halves, consistent with a biochemical function in ligation of tRNA exons. Efficient reduction of HSPC117 levels in extracts was verified by Western blot analysis (FIG. 1F). Specificity of siRNA-mediated depletion of HSPC117 was confirmed with a different set of siRNAs and by rescue of the RNAi phenotype (FIG. 5) by expression of an RNAi-resistant form of HSPC117 from a bacterial artificial chromosome (BAC) derived from mouse genomic DNA.

Example 3

HSPC117 is the Catalytic Component of Mammalian RNA>p Ligase

Figure 2A:
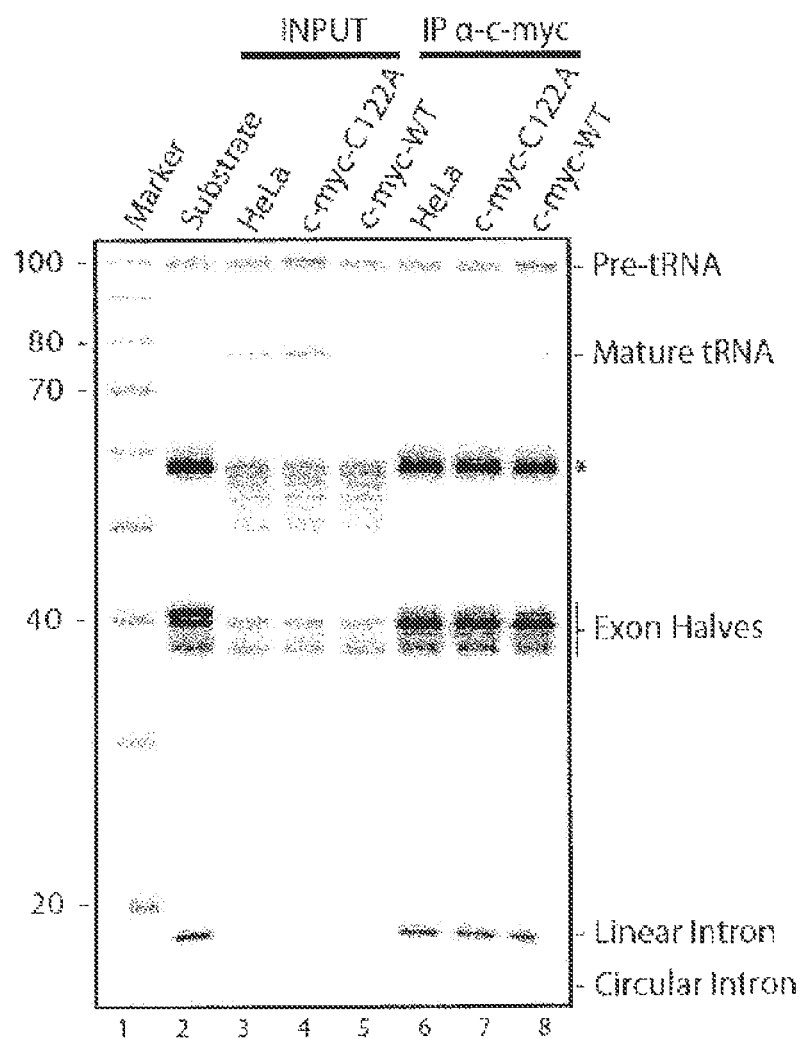
Figure 2B:
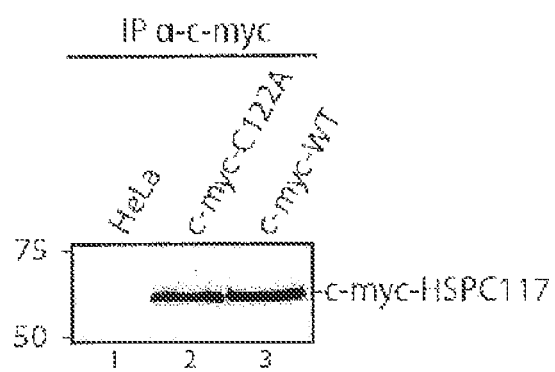

Next it was investigated whether HSPC117 is associated with RNA>p ligase activity. Therefore, stably transfected clonal HeLa cell lines expressing c-myc-tagged murine HSPC117 were established. Based on multiple sequence alignments of UPF0027 proteins (FIG. 6) and guided by the published crystal structure of RtcB from *Pyrococcus horikoshii* (Okada et al., 2006) a stably transfected clonal cell line expressing the point mutant c-myc-HSPC117 C122A was generated. To detect tRNA ligase activity independent of RTCD1 and tRNA endonuclease, tRNA exon halves were prepared by cleaving a suitable [$\alpha$-$^{32}$P]-GTP radiolabeled hybrid pre-tRNA (Englert, 2005) with recombinant splicing endonuclease from *Methanocaldococcus jannaschii* (MjT-SEN). Affinity purification of c-myc-HSPC117 yielded an immunoprecipitate (IP) that was able to ligate tRNA exon halves. In contrast, the point mutant c-myc-HSPC117 C122A was inactive as an RNA ligase (FIG. 2A, compare lanes 6 and 7 with lane 8). Comparison of equal amounts of wild-type (WT) and C122A mutant c-myc-HSPC117 was confirmed by Western blot (FIG. 2B, compare lanes 2 and 3). It was therefore concluded that HSPC117 is the catalytic component of a tRNA ligase.

Example 4

Figure 2C:
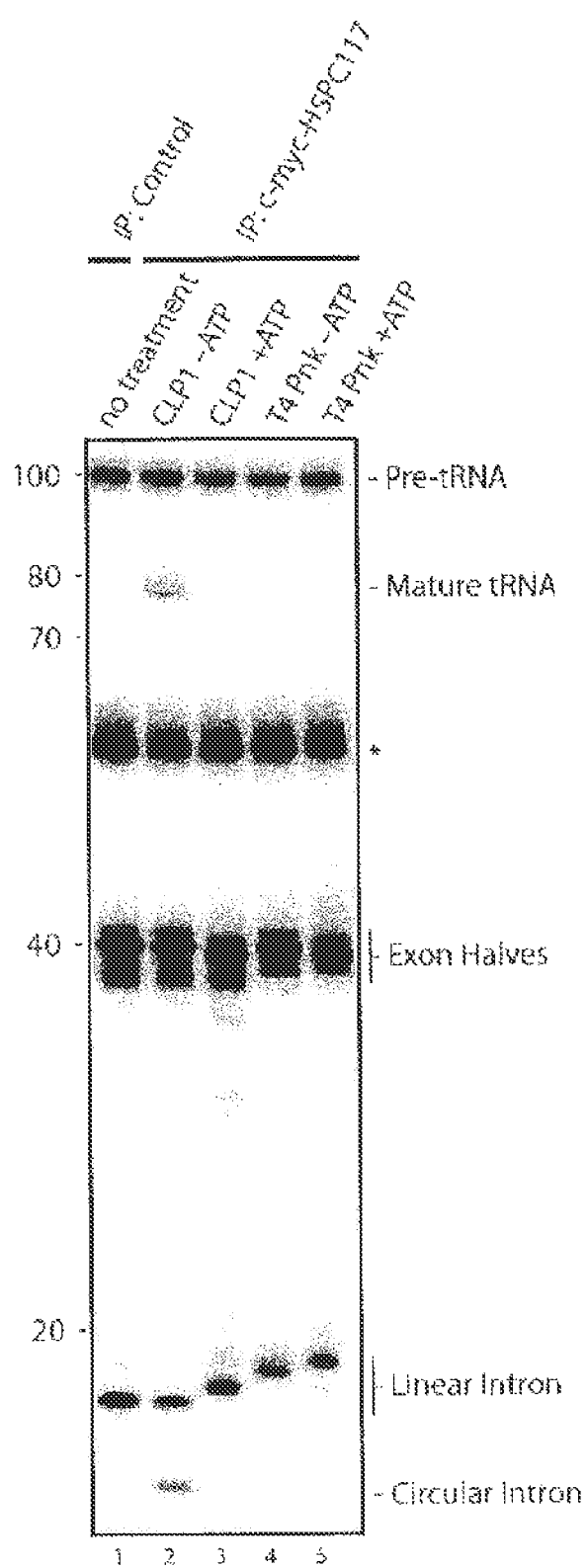
Figure 2D:
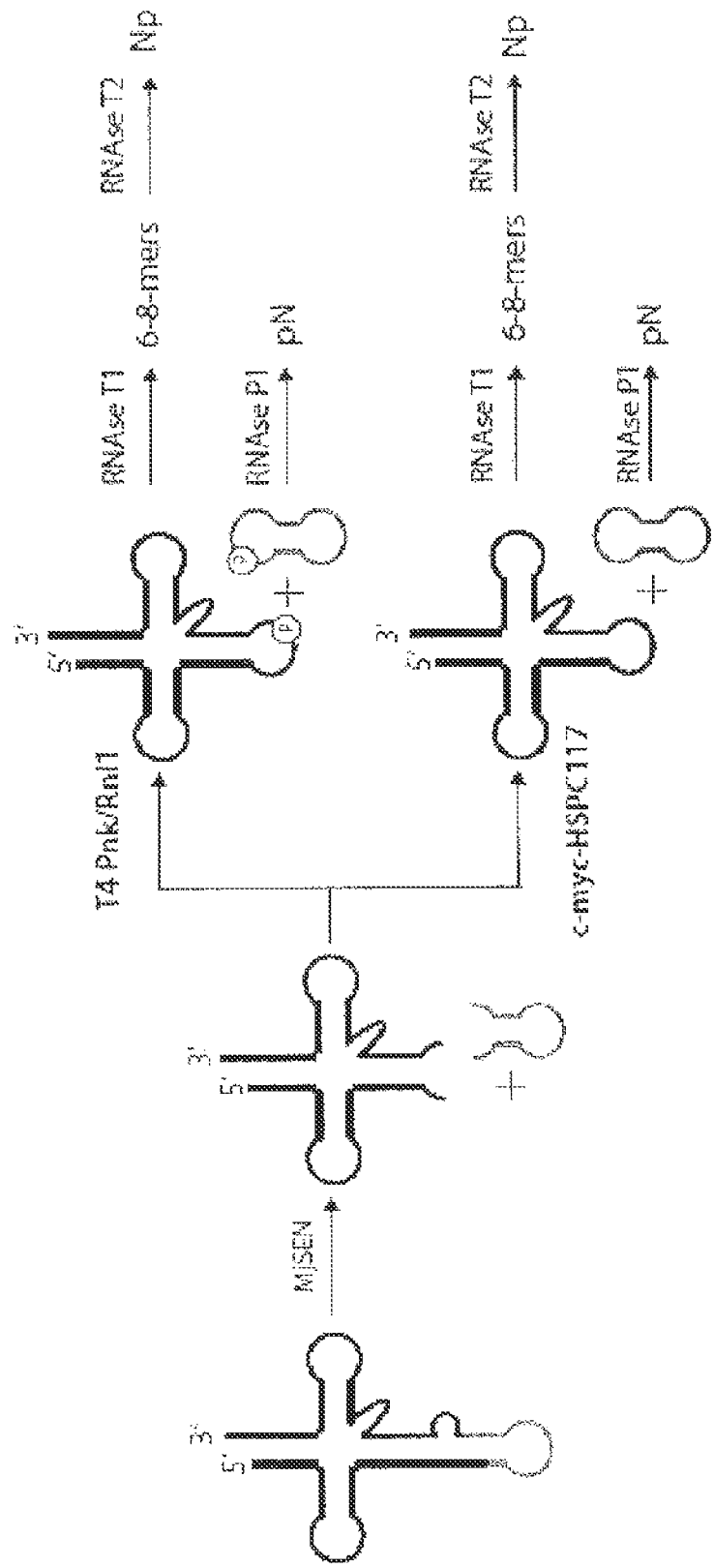
Figures 2E, 2F:
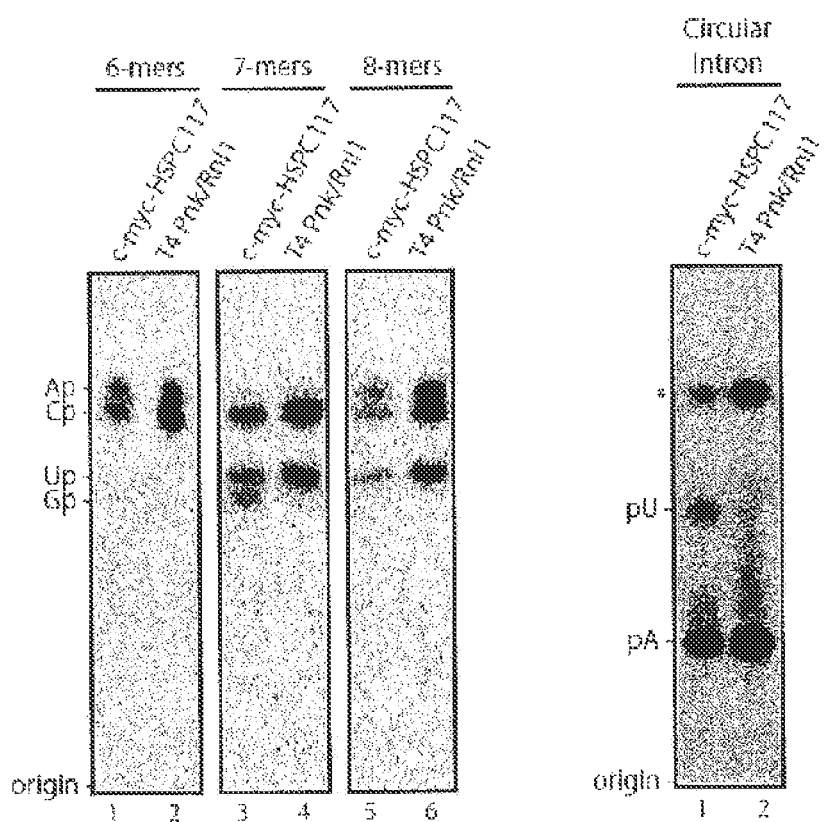

HSPC117 Catalyzes the Direct Ligation of 2',3'-Cyclic Phosphate and 5'-OH RNA Termini RNA>p ligase is predicted to require a 5'-OH at the terminus of its substrates. Consistently, no ligase activity could be detected in c-myc-HSPC117 IPs when tRNA exon halves were preincubated with recombinant 5'-OH RNA kinase CLP1 in presence of ATP to convert the 5'-OH of the 3'-exon into 5'-P (FIG. 2C, compare lanes 2 and 3). In addition to its 5'-OH RNA kinase activity, T4 Pnk is known to harbor a 2',3'-cyclic phosphodiesterase and a 3'-phosphatase activity. As expected for RNA>p ligase, we could not detect any ligase activity when we used tRNA exon halves preincubated with T4 Pnk in absence (to remove the 2',3'-cyclic phosphate) or presence of ATP (to remove the 2',3'-cyclic phosphate and to additionally convert 5'-OH into 5'-P) as substrates for ligation with c-myc-HSPC117 IP (FIG. 2C, lanes 4 and 5). Thus, ligation by the described RNA>p ligase is favourable on 5'-OH (see also FIG. 1B) and 2',3'-cyclic phosphate. The most characteristic feature of ligation of tRNA exon halves by RNA>p ligase is the generation of mature tRNAs that contain the precursor-derived splice junction phosphate in a canonical 5',3'-phosphodiester bond (FIG. 1A, lower branch). To test whether this is true for RNA ligation catalyzed by c-myc-HSPC117 IP a nearest neighbor analysis was performed of the splice junction phosphate (FIG. 2D). tRNA exon halves with radiolabeled 2',3'-cyclic phosphate at the terminus of the 5'-exon half were prepared by cleaving [α-$^{32}$P]-UTP-radiolabeled pre-tRNA with recombinant splicing endonuclease (FIG. 7). These exon halves were ligated either by incubation with c-myc-HSPC117 IP or with a mixture of T4 Pnk and bacteriophage T4 RNA ligase 1 (T4 Rnl1) as a negative control. Mature tRNA was isolated from these reactions and digested by RNAse T1 which cleaves RNA 3' of every guanosine nucleotide and processes its substrates into fragments terminated by guanosine 3'-monophosphate (Gp). Fragments ranging from 6-8 nucleotides in length were isolated, digested by RNAse T2 and resulting nucleotide 3'-monophosphates resolved by thin layer chromatography. Following this procedure, radiolabeled Gp was only detected in RNA 7-mers derived from mature tRNA generated by c-myc-HSPC117, indicating retention of the precursor-derived splice junction phosphate (FIG. 2E, lane 3). As expected, the splice junction phosphate was exchanged in control ligations performed with T4 Pnk and T4 Rnl1 (FIG. 2E, lane 4). Since no radiolabeled NTP was added to any ligation reactions, no radiolabeled Gp could be detected in RNAse T2 digests of RNAse T1-7-mers derived from mature, T4 Rnl1-ligated tRNA (FIG. 2E, lane 4). A similar nearest neighborhood analysis was also carried out with 2',3'-cyclic phosphate terminally radiolabeled linear intron after its conversion to circularized intron by c-myc-HSPC117 IP. Detection of radiolabeled Uridine 5'-monophosphate (pU) in P1 nuclease digests of intron circularized by c-myc-HSPC117 but not by T4 Pnk/Rnl1 supported retention of the splice junction phosphate (FIG. 2F, compare lanes 1 and 2). It was concluded that the identified RNA>p ligase joins tRNA exon halves by incorporating the precursor-derived splice junction phosphate into the mature tRNA in a canonical 3',5'-phosphodiester bond.

Example 5

HSPC117 Resides in a Stable Heteromeric Protein Complex

Figure 3A:
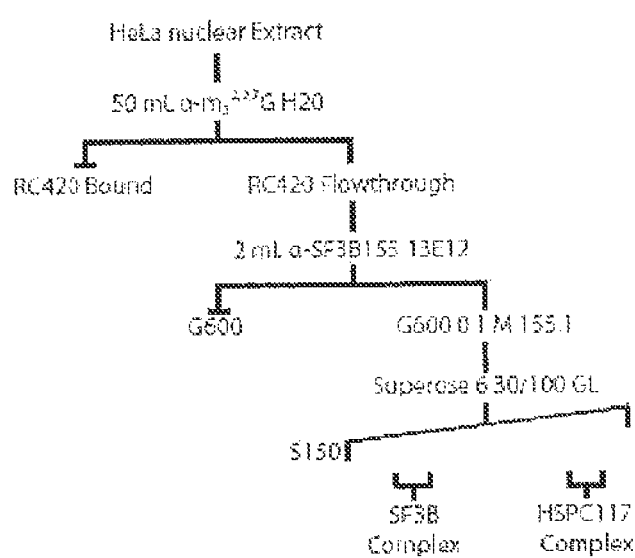
Figure 3B:
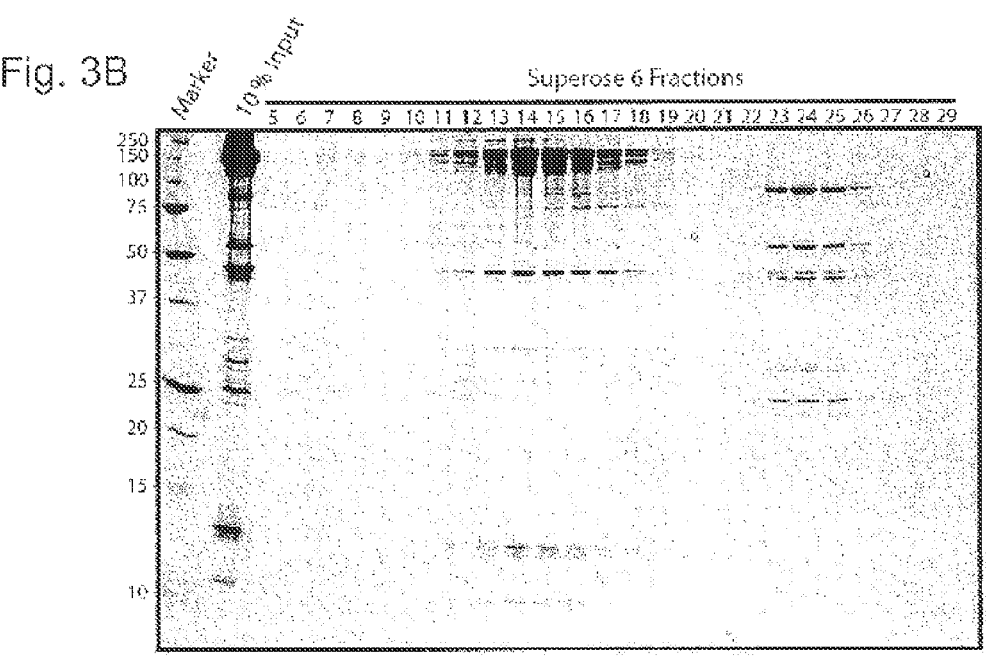
Figure 3C:
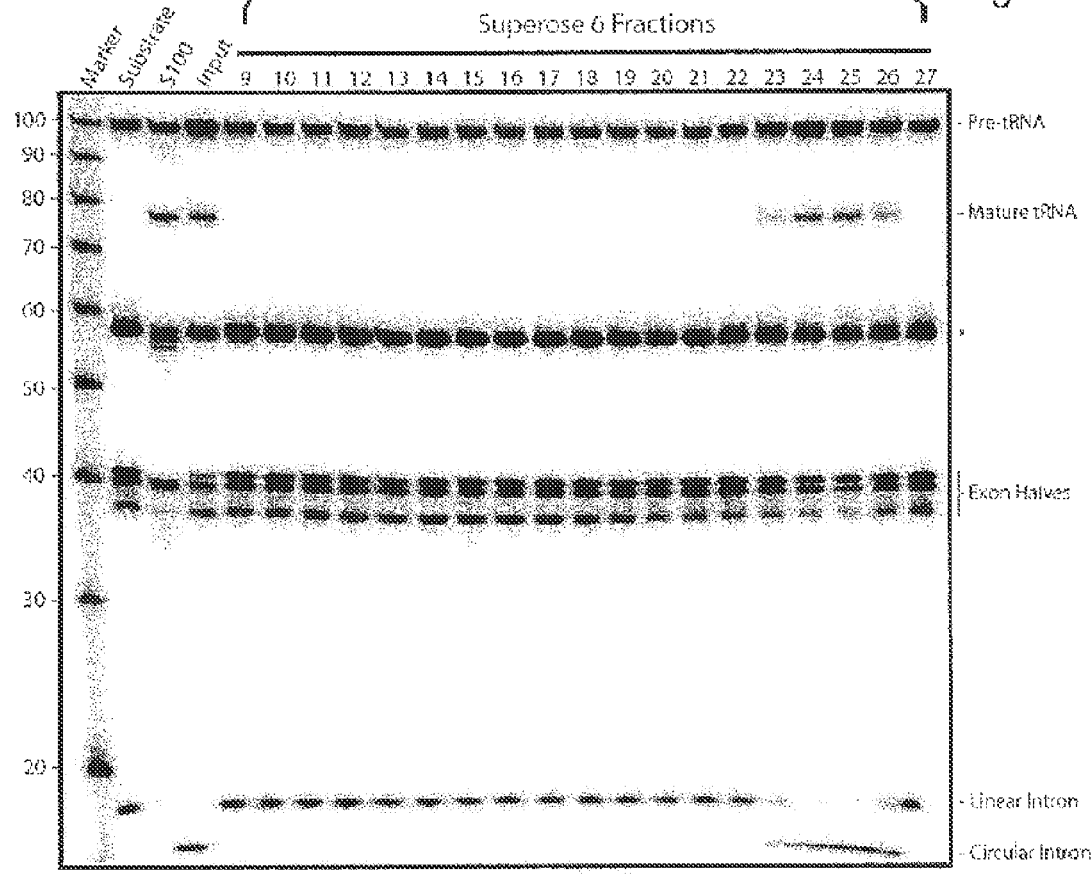
Figure 3D:
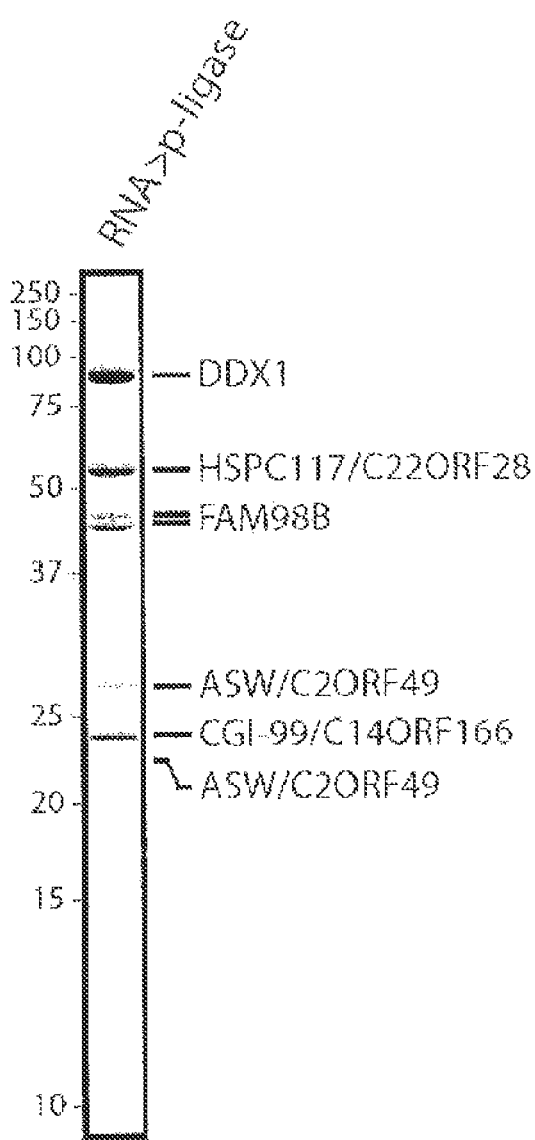
Figure 3E:
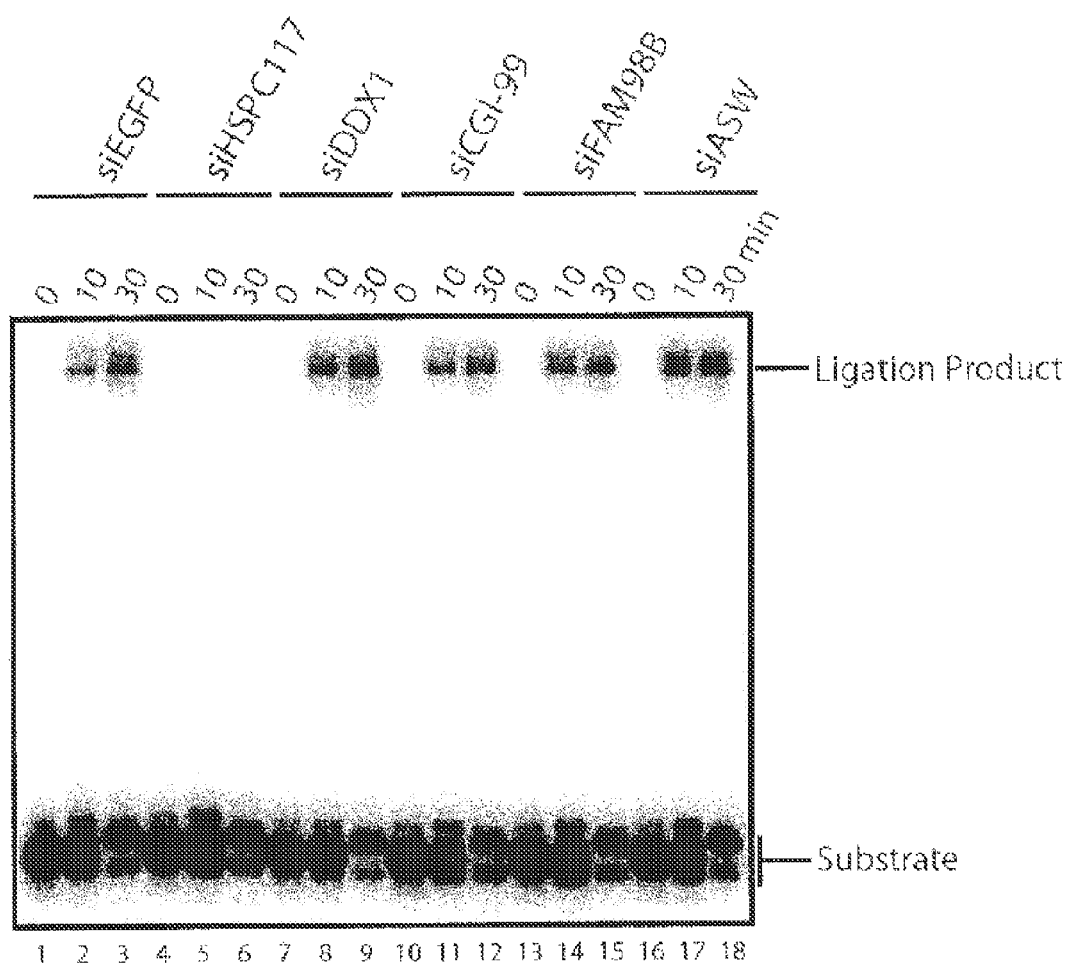
Figure 3F:
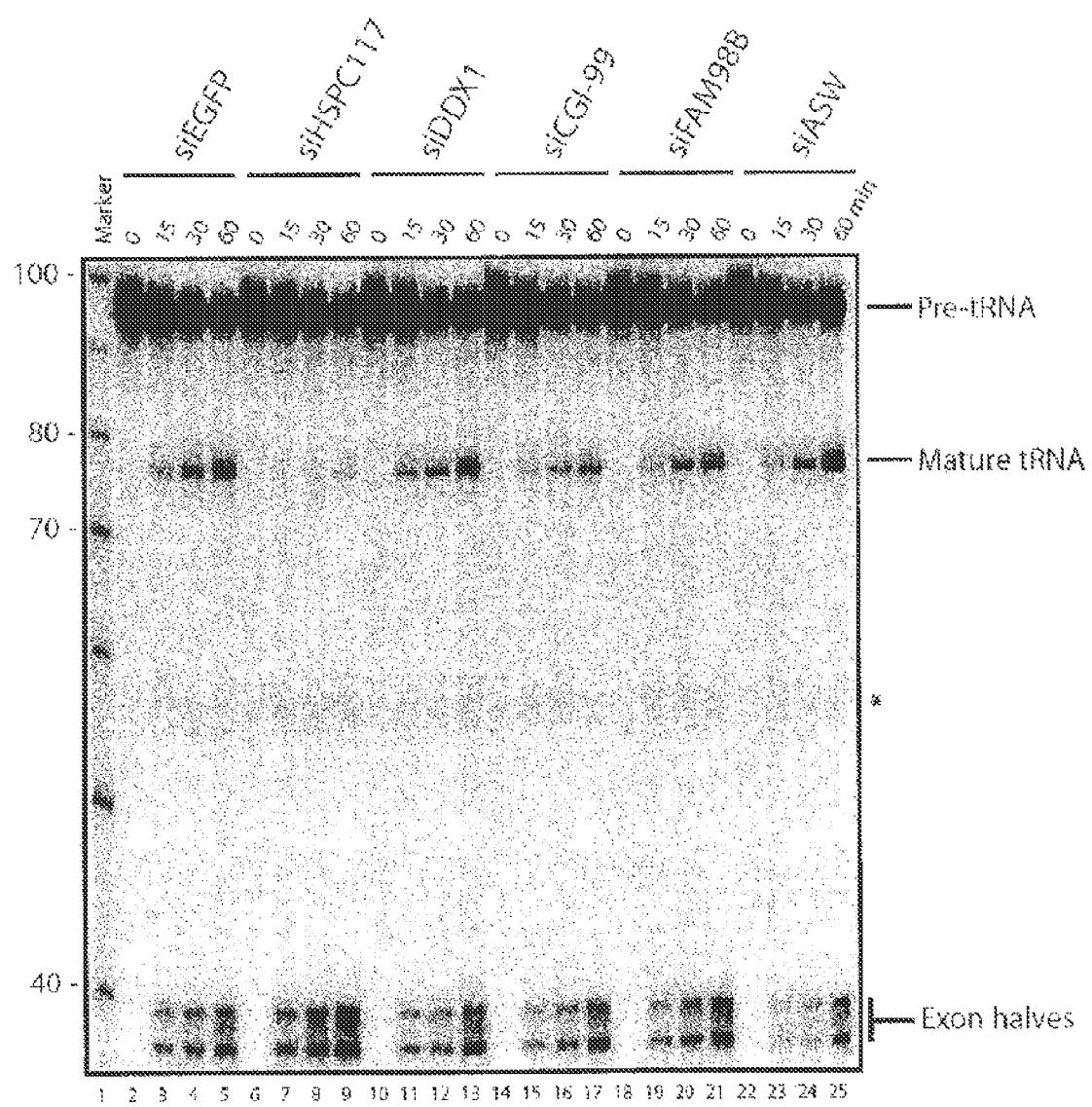

Strikingly, in parallel to our efforts to purify RNA>p ligase, a stable and highly homogenous HSPC117-containing complex of so far unknown function was found to copurify with spliceosomal SF3B particles prepared from nuclear HeLa cell extracts. Therefore, a SF3B-associated and highly purified HSPC117-complex was tested to exhibit RNA>p ligase activity. SF3B-associated HSPC117-complex was obtained by dissociation of SF3B and U2 spliceosomal complexes followed by selective immunodepletion of U2. Unbound SF3B- and HSPC117-complexes were recovered from the flow-through, captured by an anti-SF3B155-coupled resin and specifically eluted with antibody epitope peptide (FIG. 3A). After elution from the affinity column, SF3B- (FIG. 3B, fractions 12-19) and HSPC117-complexes (FIG. 3B, fractions 23-26) were separated by size exclusion chromatography on Superose 6. In agreement with the initial data obtained with c-myc-HSPC117 IPs, fractions containing the HSPC117-complex but not the SF3B spliceosomal complex converted tRNA exon halves and linear intron into mature tRNA and circularized intron, respectively (FIG. 3C). In addition, the same fractions could biochemically rescue the tRNA splicing defect of extracts RNAi-depleted of HSPC117 (FIG. 8). Proteins identified in this HSPC117-containing complex were analyzed by tryptic digest of single bands isolated from Coomassie blue stained gels followed by MS analysis. In addition to C22ORF28/HSPC117 identified proteins comprised the DEAD box helicase DDX1 and the ninein interacting protein C14ORF166/CGI-99 in addition to FAM98B and substoichiometric amounts of ASW/C20RF49 (FIG. 3D). This set of proteins overlaps with the results of the MS analysis of immunoprecipitates of c-myc-HSPC117 from stable cell clones (Tab. 2) and the proteins identified in the MonoQ RNA>p ligase fraction (FIG. 1C and Tab. 1).

TABLE 1

Proteins identified by in solution tryptic digest and MS analysis of MonoQ fraction enriched for RNA > p ligase.
Proteins Identified in Enriched RNA Ligase MonoQ Fraction.

| Gene Symbol | Number of Unique Peptides |
|---|---|
| EEF2 | 34 |
| MSN | 34 |
| ELAC2 | 28 |
| CCT2 | 23 |
| CCT8 | 22 |
| HSPA8 | 22 |
| PKM2 | 20 |
| SYNCRIP | 20 |
| NARS | 19 |
| PUS7L | 17 |
| SND1 | 16 |
| CCT5 | 15 |
| HSPA1B | 15 |
| RDX | 15 |
| CACYBP | 14 |
| CCT6A | 14 |
| DUS3L | 14 |
| G6PD | 14 |
| GLT25D1 | 14 |
| NMT1 | 14 |
| CCT3 | 13 |
| FARSB | 13 |
| MTHFD1 | 13 |
| ACLY | 12 |

TABLE 1-continued

Proteins identified by in solution tryptic digest and MS analysis of MonoQ fraction enriched for RNA > p ligase. Proteins Identified in Enriched RNA Ligase MonoQ Fraction.

| Gene Symbol | Number of Unique Peptides |
|---|---|
| EIF4A3 | 12 |
| GARS | 12 |
| LGTN | 12 |
| SSB | 12 |
| TCP1 | 12 |
| ABCE1 | 11 |
| HSPA9 | 11 |
| IDH1 | 11 |
| BASP1 | 10 |
| FAM129B | 10 |
| FKBP4 | 10 |
| GMPS | 10 |
| BLVRA | 9 |
| C22orf28 | 9 |
| LRRC40 | 9 |
| METTL1 | 9 |
| PAPSS2 | 9 |
| TSFM | 9 |
| CCT7 | 8 |
| SERBP1 | 8 |
| SLC9A3R1 | 8 |
| PRPS1 | 7 |
| SHMT2 | 7 |
| CWF19L1 | 6 |
| DDX1 | 6 |
| NAMPT | 6 |
| PRPSAP2 | 6 |
| TWF1 | 6 |
| ANKZF1 | 5 |
| CALD1 | 5 |
| EIF4B | 5 |
| EIF4H | 5 |
| FARSA | 5 |
| GART | 5 |
| PAPSS1 | 5 |
| RNASEH2B | 5 |
| RPRD1B | 5 |
| RRM1 | 5 |
| WDR4 | 5 |
| ATE1 | 4 |
| CMPK1 | 4 |
| CPS1 | 4 |
| EEF1A1 | 4 |
| ERP29 | 4 |
| MAT2A | 4 |
| NME1-NME2 | 4 |
| PPWD1 | 4 |
| RNASEH2C | 4 |
| UBE2N | 4 |
| CHMP2A | 3 |
| DUS2L | 3 |
| FAM98B | 3 |
| HNRNPK | 3 |
| HSPA14 | 3 |
| LRPAP1 | 3 |
| PFKM | 3 |
| PUS7 | 3 |
| RNASEH2A | 3 |
| TRMT112 | 3 |
| WBSCR22 | 3 |
| AKR7A2 | 2 |
| C14orf166 | 2 |
| PAWR | 2 |
| RAN | 2 |
| RANBP1 | 2 |
| RDBP | 2 |
| UBE2V1 | 2 |

TABLE 2

Proteins Identified in c-myc-HSPC117 Immunopurifications sorted by enrichment.

| Gene Symbol | Number of Unique Peptides | |
|---|---|---|
| | Control | Sample |
| DDX1 | 0 | 35 |
| C22orf28 | 0 | 27 |
| FAM98B | 0 | 14 |
| C14orf166 | 0 | 12 |
| FAM98A | 0 | 10 |
| HSPA5 | 0 | 5 |
| RPS14 | 0 | 3 |
| RPL11 | 0 | 3 |
| KPNA3 | 0 | 3 |
| YWHAE | 0 | 2 |
| RPL7 | 0 | 2 |
| RPL32P18 | 0 | 2 |
| RPL10A | 0 | 2 |
| PRSS3 | 0 | 2 |
| LMNA | 0 | 2 |
| FAM178A | 0 | 2 |
| DNAH14 | 0 | 2 |
| CSTF3 | 0 | 2 |
| CSTF1 | 0 | 2 |
| ATP5B | 0 | 2 |
| AHCY | 0 | 2 |
| DDX23 | 3 | 7 |
| DDX21 | 4 | 9 |
| RPS3 | 2 | 4 |
| RPL21 | 2 | 4 |
| MTDH | 3 | 5 |
| RPL28 | 5 | 8 |
| TUBA1B | 4 | 6 |
| RPS18 | 2 | 3 |
| RPL24 | 2 | 3 |
| EHBP1L1 | 19 | 26 |
| HSPA8 | 11 | 15 |
| KPNA2 | 6 | 8 |
| RPL34 | 3 | 4 |
| RPL3 | 3 | 4 |
| RPL15 | 3 | 4 |
| HIST1H3D | 3 | 4 |
| ILF3 | 20 | 26 |
| TUBB | 7 | 9 |
| TFRC | 4 | 5 |
| ILF2 | 4 | 5 |
| HNRNPA3 | 5 | 6 |
| EIF2C2 | 7 | 8 |
| DDX41 | 9 | 10 |
| HNRN-PA2B1 | 12 | 13 |
| KRT1 | 26 | 28 |
| HNRN-PUL2 | 20 | 21 |
| HNRNPU | 20 | 21 |
| HNRPUL1 | 22 | 23 |
| PRKDC | 14 | 14 |
| RPL4 | 5 | 5 |
| RPL13 | 5 | 5 |
| HNRNPH1 | 5 | 5 |
| HIST1H4H | 5 | 5 |
| RPS11 | 4 | 4 |
| RPL18 | 4 | 4 |
| RPL17 | 4 | 4 |
| HIST1H2BD | 4 | 4 |
| UBC | 3 | 3 |
| RPS26 | 3 | 3 |
| RBBP8 | 3 | 3 |
| EEF1A1 | 3 | 3 |
| ZNF326 | 2 | 2 |
| YBX1 | 2 | 2 |
| RPL37A | 2 | 2 |
| RPL35A | 2 | 2 |
| RPL29 | 2 | 2 |
| MYC | 2 | 2 |
| HIST1H2AB | 2 | 2 |
| TRIM21 | 21 | 20 |
| LGALS3BP | 16 | 14 |
| TFG | 8 | 7 |

TABLE 2-continued

Proteins Identified in c-myc-HSPC117 Immunopurifications sorted by enrichment.

| Gene Symbol | Number of Unique Peptides Control | Number of Unique Peptides Sample |
|---|---|---|
| MATR3 | 8 | 7 |
| ACTB | 8 | 7 |
| RBM14 | 15 | 13 |
| RPL7A | 7 | 6 |
| HNRNPH3 | 7 | 6 |
| FUS | 7 | 6 |
| UTP14A | 13 | 11 |
| VIM | 6 | 5 |
| TNRC6B | 33 | 27 |
| TNRC6A | 27 | 22 |
| ZNF280D | 5 | 4 |
| RPL27 | 5 | 4 |
| RPL14 | 5 | 4 |
| APOBEC3B | 8 | 6 |
| BBX | 4 | 3 |
| HNRNPA1 | 7 | 5 |
| BEND3 | 21 | 14 |
| RPL8 | 3 | 2 |
| RPL27 | 3 | 2 |
| NKAP | 3 | 2 |
| HIST1H1D | 3 | 2 |
| CSTA | 3 | 2 |
| ARL6IP4 | 3 | 2 |
| RPS23 | 5 | 3 |
| RPS6 | 7 | 4 |
| RPL6 | 6 | 3 |
| RPL23 | 4 | 2 |
| RPL10 | 4 | 2 |
| DSP | 11 | 5 |
| HNRNPAB | 6 | 2 |
| JUP | 10 | 3 |
| IGH@ | 7 | 2 |
| ZNF192 | 4 | 0 |
| VCP | 3 | 0 |
| TF | 2 | 0 |
| TAF15 | 3 | 0 |
| SMC3 | 9 | 0 |
| SMC1A | 5 | 0 |
| SBSN | 2 | 0 |
| RPS9 | 2 | 0 |
| RPS4X | 8 | 0 |
| RPS13 | 3 | 0 |
| RPL36 | 2 | 0 |
| RPL19 | 2 | 0 |
| RPL18A | 2 | 0 |
| RP9 | 4 | 0 |
| RIF1 | 7 | 0 |
| RAD21 | 2 | 0 |
| PCMT1 | 2 | 0 |
| PABPC1 | 2 | 0 |
| MUCL1 | 2 | 0 |
| IgM | 2 | 0 |
| IGHA1 | 3 | 0 |
| IgG light chain | 2 | 0 |
| IgA light chain | 3 | 0 |
| Ig kappa chain | 3 | 0 |
| HNRNPM | 3 | 0 |
| GAPDH | 2 | 0 |
| FLG2 | 3 | 0 |
| FLG | 6 | 0 |
| FAM133B | 2 | 0 |
| DSG1 | 5 | 0 |
| CIR1 | 2 | 0 |
| C5 | 2 | 0 |
| C3 | 6 | 0 |
| AZGP1 | 2 | 0 |
| APOD | 2 | 0 |
| A2M | 3 | 0 |

Proteins identified by in solution tryptic digest and MS analysis of affinity purified c-myc-HSPC117.

Figure 3G:
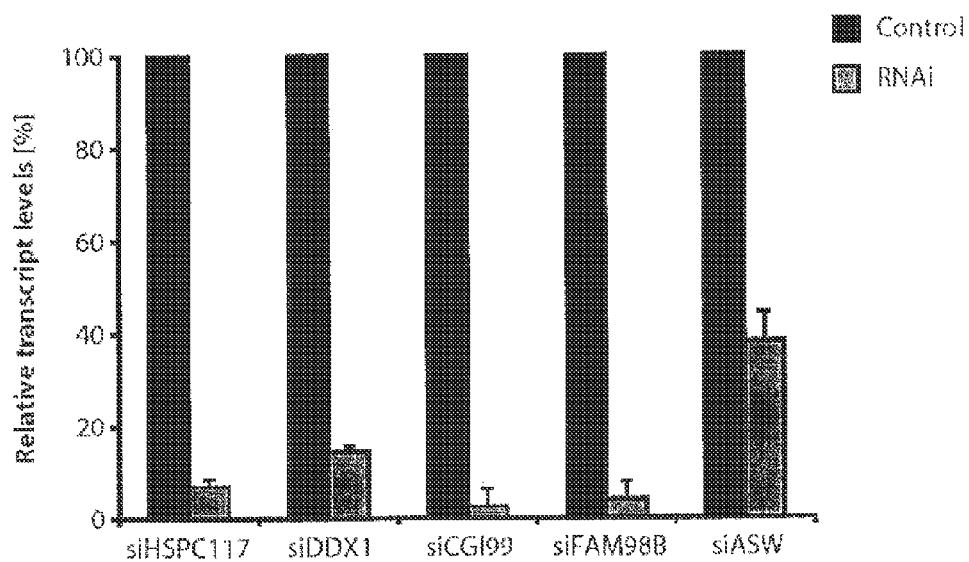
Figure 3H:
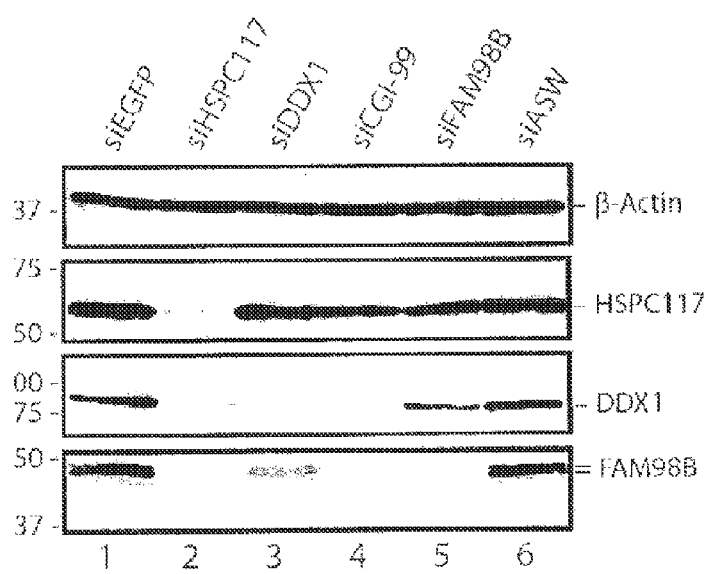

Silencing of the mentioned interactors of HSPC117 did not have an effect on interstrand ligation (FIG. 3E) or tRNA maturation (FIG. 3F), despite the efficient reduction of mRNA levels (FIG. 3G). Western blot analysis of protein extracts depleted either of HSPC117, DDX1, CGI-99, FAM98B and CGI-99 confirmed efficient depletion of HSPC117, DDX1 and FAM98B (FIG. 3H). Remarkably, depletion of HSPC117 also led to decreased protein levels of the other complex members DDX1 and FAM98B. Similarly, depletion of both DDX1 and CGI-99 was accompanied by depletion of DDX1 and FAM98B. Interestingly, HSPC117 containing complexes were reported to exhibit affinity for cruciform DNA structures (Drewett et al., 2001). We were able to inhibit both inter-strand ligation (FIG. 9A) and tRNA maturation (FIG. 9B) with cruciform but not control double stranded DNA. Taken together, these data provide robust evidence for a stable complex composed of HSPC117/C22ORF28, DDX1, CGI-99/C14ORF166 and FAM98B exhibiting RNA>p ligase activity. The copurification of SF3B spliceosomal particles and RNA>p ligase reveals a link between canonical mRNA splicing and RNA>p ligase intriguing.

Example 6

HSPC117 is Involved in tRNA Ligation in Living Cells

Figure 4A:
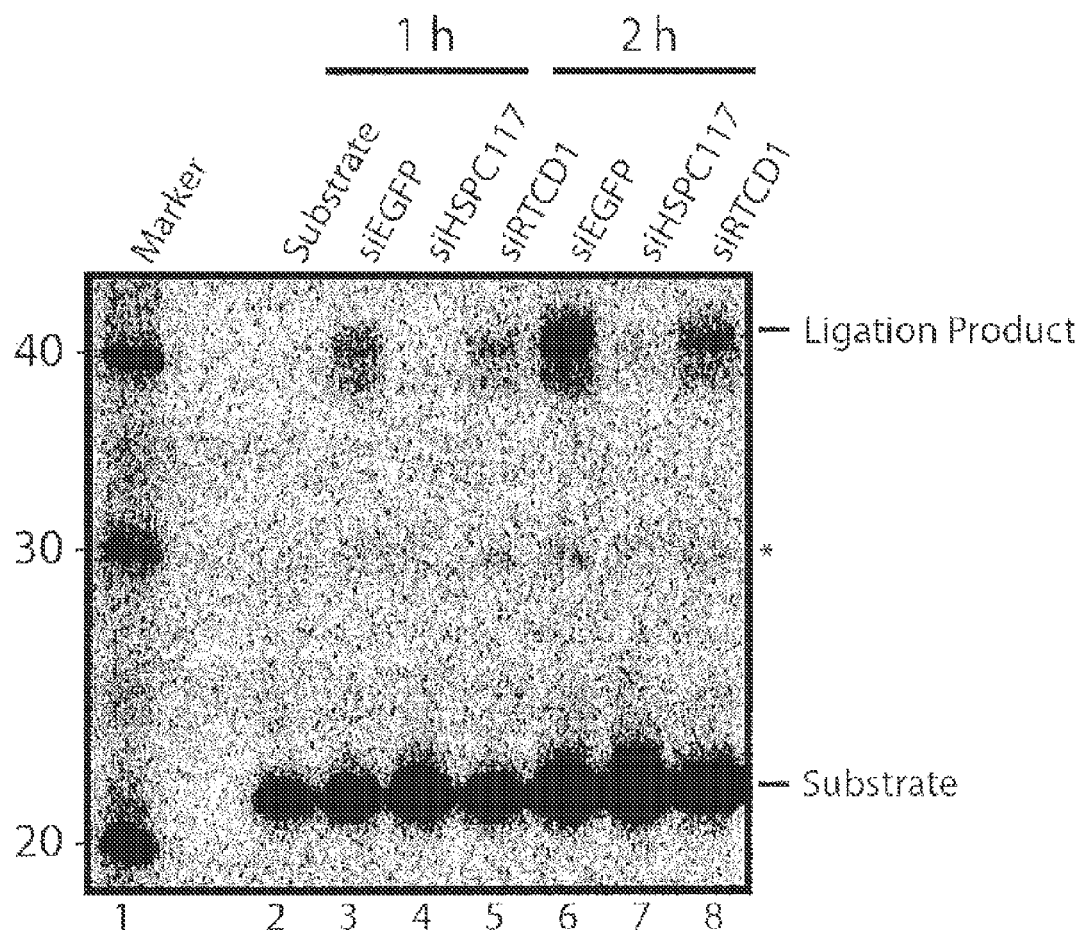
Figure 4B:
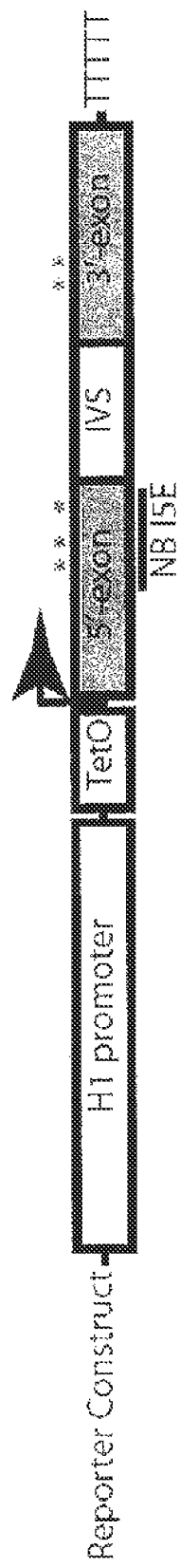
Figure 4C:
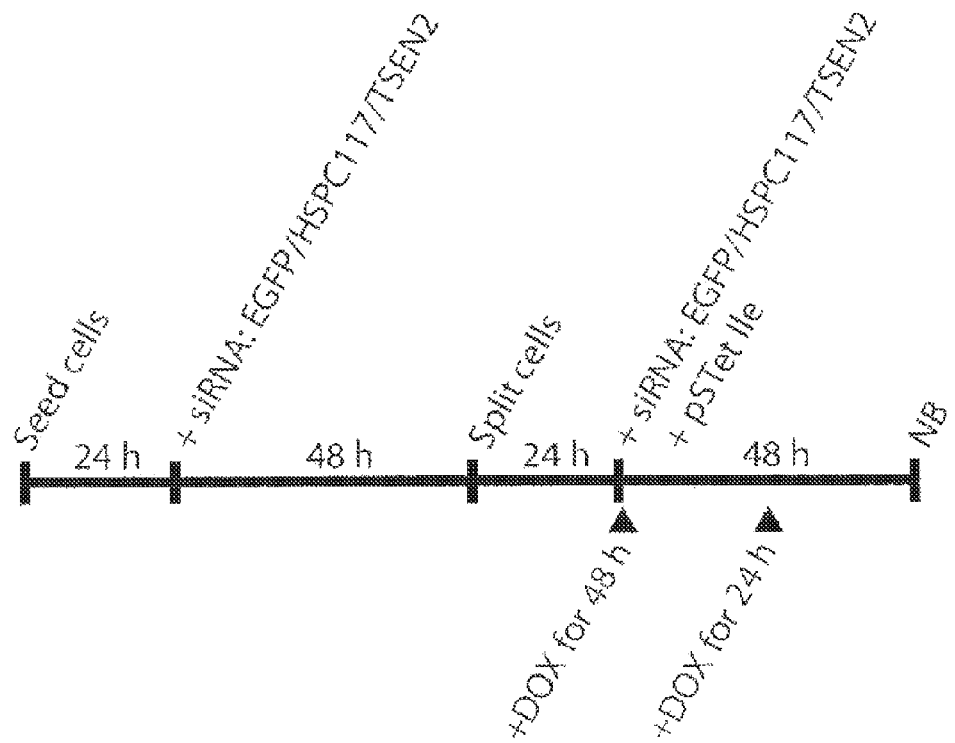
Figure 4D:
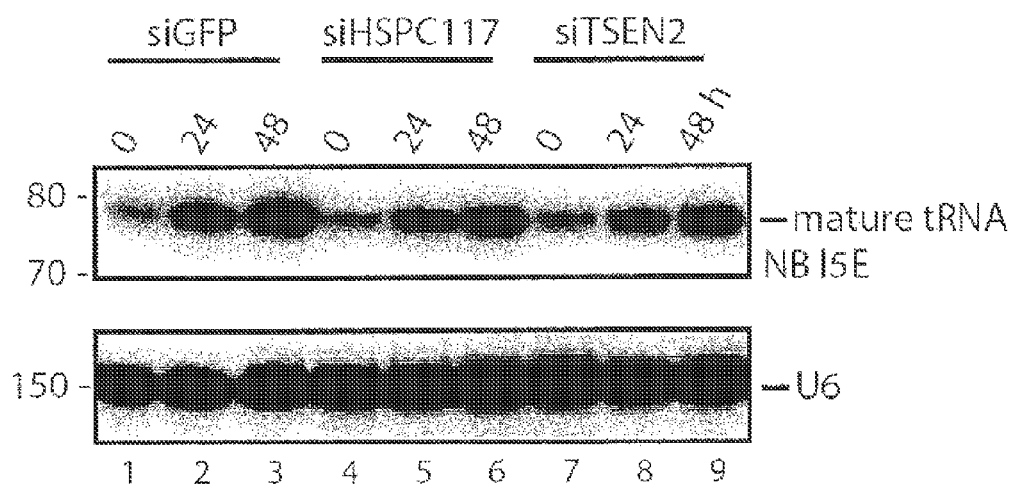
Figure 4E:
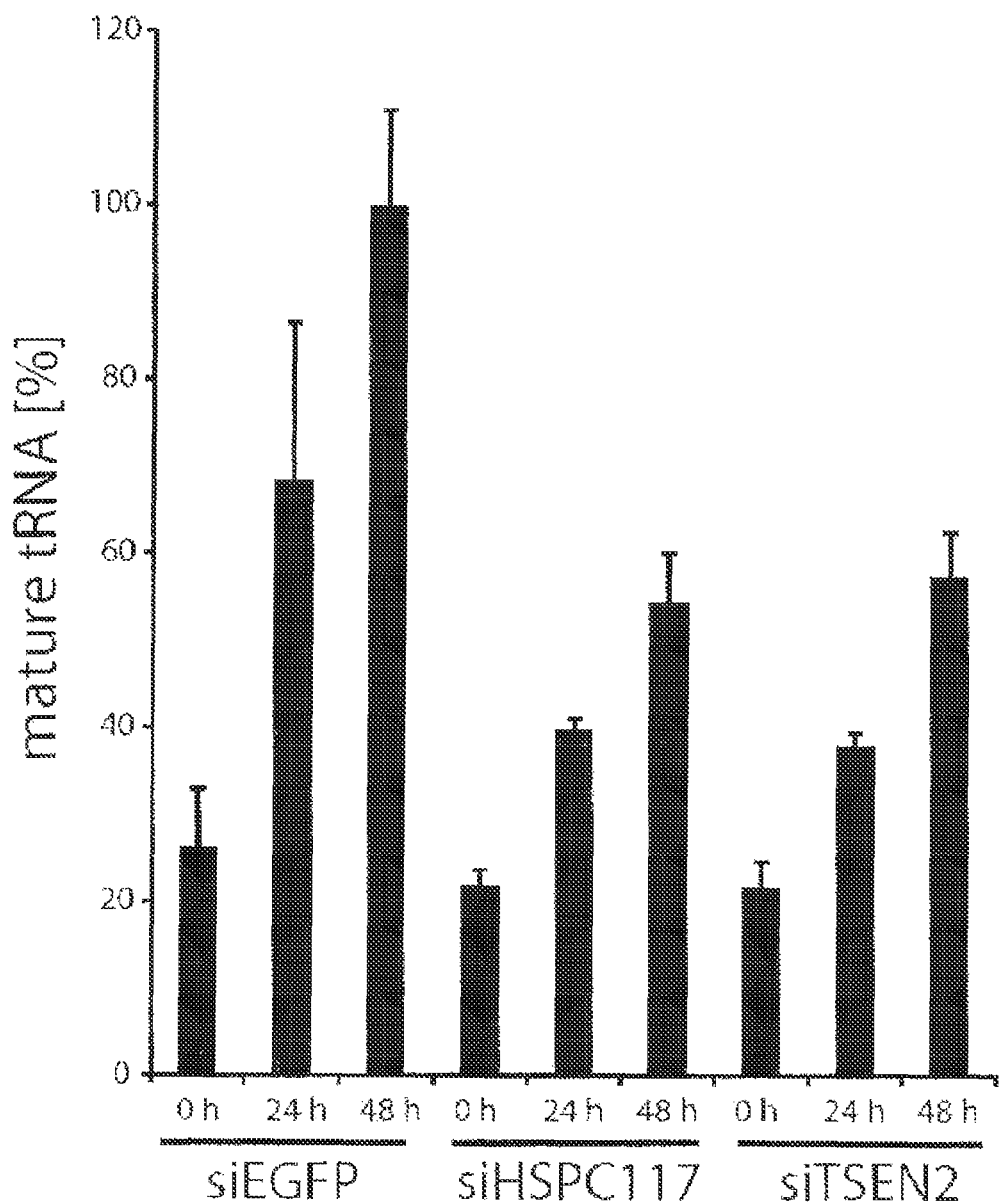

After demonstrating that HSPC117 is a member of a complex capable of directly joining RNA 2',3'-cyclic phosphate and 5'-OH termini in vitro, we next investigated the role of HSPC117 in RNA ligation in vivo. We first tested whether inter-strand ligation can occur in living cells by transfection of [5'-$^{32}$P]-pCp-radiolabeled dsRNA into HeLa cells, RNAi-depleted of RNA terminal cyclase (RTCD1), HSPC117 or EGFP as a control gene (FIG. 4A). Isolation and analysis of total RNA by gel electrophoresis demonstrated that the radiolabeled 3'-P dsRNAs were taken up by the cells and subsequently ligated. In vivo, inter-strand ligation was dependent on HSPC117 (FIG. 4A, compare lanes 4 and 7 with lanes 3 and 6, respectively) and to a less pronounced extent on RTCD1 (FIG. 4A, compare lanes 5 and 8 with lanes 3 and 6, respectively). In order to test the effect of RNAi-mediated depletion of HSPC117 on processing of de novo synthesized pre-tRNA, a system that has previously been applied to study mitochondrial import of tRNA in *Trypanosoma brucei* (Bouzaidi-Tiali et al., 2007) was employed. siRNAs targeting HSPC117, the human splicing endonuclease subunit TSEN2 or EGFP as controls together with a reporter construct, encoding tagged pre-tRNA Ile$^{TAT}$ (FIG. 9) under control of a Tetracyclin (Tet) responsive promoter (FIG. 4B), were transfected into HeLa cells stably expressing Tet-repressor. After induction at selected time points (FIG. 4C), RNA was extracted and analyzed by Northern blot. Probing of the blot for the 5'-exon of the tagged tRNA Ile$^{TAT}$ (probe 15E, FIG. 4B) revealed a clear delay in the formation of mature tRNA upon RNAi-mediated depletion of HSPC117 and TSEN2 but not upon EGFP control siRNA treatment (FIG. 4D, compare lanes 1-3 with lanes 4-6 or 7-9, respectively and FIG. 4E). Taken together, these data establish a role for HSPC117 as an RNA ligase with broad substrate specificity and with a function in tRNA processing.

Example 7

Figure 7B:
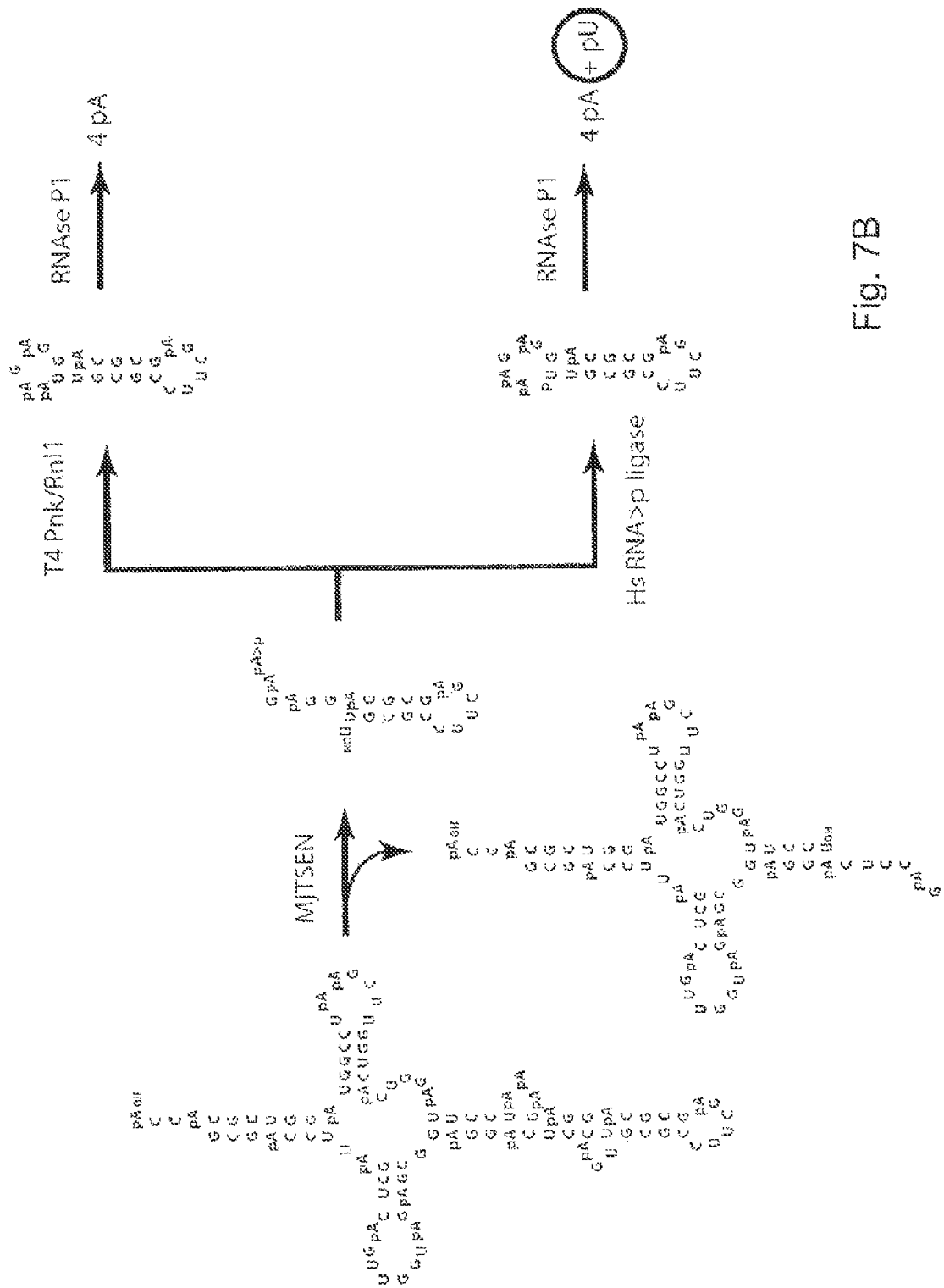

Potential Functions of HSPC117 as the First RNA Ligase to be Discovered in Humans HSPC117 is the catalytic subunit of a human RNA ligase complex. The known ATPase and unwinding activity of helicases suggest a potential role for DDX1 in ATP-dependent conformational changes to support tRNA splicing. In fact, DDX1 is the only polypeptide associated with the RNA>p ligase-dependent tRNA splicing pathway that has been shown to require ATP for its action as a DEAD-box helicase. This could explain the supportive but dispensable role of ATP in the endonuclease-RNA>p ligase reaction cascade which, mechanistically, does not require any additional energy. Little is known about the potential functions of CGI-99, FAM98B and ASW. The data herein, based on RNAi-mediated depletion, suggest a non-essential role for the ligation of tRNA halves (FIGS. 7B and C).

Both RNA>p ligase and T4 Pnk/Rnl1-like ligation mechanisms can be detected in human cells (Filipowicz and Shatkin, 1983). Here, we have identified components of an RNA>p ligase pathway. Proteins catalyzing the 5'-OH kinase and 2',3'-cyclic phosphodiesterase healing reactions as well as the final phosphotransferase step (required for this pathway have been identified in humans. In addition, it has recently been demonstrated by heterocomplementation studies in yeast that these proteins can indeed function as tRNA splicing enzymes in vivo. Earlier studies show that the RNA>p ligase pathway is the prevalent tRNA ligation pathway in mammals (Filipowicz and Shatkin, 1983).

The RNA>p ligase complex described here is the first identified RNA ligase protein that is capable of directly joining the 2',3'-cyclic phosphate, 5'-OH displaying products of the tRNA endonuclease reactions without the necessity of prior "healing" of RNA termini. This implies a more general role of RNA>p ligase in RNA repair pathways. Instructive examples of RNA repair systems are known from prokaryotes. Recently, the role of RNA repair in eukaryotes has received increasing attention. RNA>p ligase is involved in human RNA repair routes and non-canonical splicing events mediated by HSPC117. Stress-induced cleavage and subsequent spliceosome-independent ligation of mRNA during the unfolded protein response (UPR) exemplifies such a non-canonical splicing event requiring an RNA ligase. The pathway has been extensively investigated in S. cerevisiae and has implicated the yeast tRNA ligase Trl1p in the final ligation step. A similar UPR pathway that relies on stress-induced non-conventional splicing of the XBP1 mRNA exists in human cells. However, the responsible ligase was previously unknown. Previous work suggests that the phosphotransferase TPT1, which is a potential component of the T4 Pnk-like RNA ligation pathway in humans, is dispensable for stress-induced splicing of the XBP1 mRNA. HSPC117 acts as an RNA>p ligase in the human UPR pathway.

In addition, RNA ligases have been proposed to be involved in viral replication in humans. For example, a host-encoded ligase has previously been postulated to circularize the RNA genome of Hepatitis Delta virus (HDV) during rolling cycle replication in humans. It appears that the HSPC117-containing ligase complex described here participates in host-mediated viral genome circularization. Recently, both HSPC117 and DDX1 have been reported to be required for replication of HDV in human cells. Furthermore, all members of the described RNA>p ligase complex have been shown to interact with kinesin-associated RNA transport granules in mouse brain extracts. Intriguingly, RTCD1 was also found to be associated with these RNA transport granules, thereby establishing a potential functional link between RNA terminal phosphate cyclization and RNA ligation.

The high degree of conservation of HSPC117/RtcB proteins in organisms as distantly related as humans and E. coli shows the universal and important roles for this protein family. Initial work indeed established an essential function for HSPC117 in mammalian development. On the other hand, no biological function could so far be assigned to the operon harboring HSPC117/RtcB and RtcA in some bacteria. Herein the molecular function of HSPC117/RtcB proteins has been elucidated.

REFERENCES

Abelson, J., Trotta, C. R., and Li, H. (1998). tRNA splicing. The Journal of biological chemistry 273, 12685-12688.

Bouzaidi-Tiali, N., Aeby, E., Charriere, F., Pusnik, M., and Schneider, A. (2007). Elongation factor 1a mediates the specificity of mitochondrial tRNA import in T. brucei. The EMBO journal 26, 4302-4312.

Chan, P. P., and Lowe, T. M. (2009). GtRNAdb: a database of transfer RNA genes detected in genomic sequence. Nucleic acids research 37, D93-97.

Drewett, V., Molina, H., Millar, A., Muller, S., von Hesler, F., and Shaw, P. E. (2001). DNA-bound transcription factor complexes analysed by mass-spectrometry: binding of novel proteins to the human c-fos SRE and related sequences. Nucleic acids research 29, 479-487.

Englert, M. (2005). Mechanismus des pre-tRNA Spleißens: Struktur und Funktion pflanzlicher und animaler RNA Ligasen. In PhD thesis, Faculty of Chemistry and Pharmaceutics (Würzburg, Bayerische Julius-Maximilians-Universität), pp. 139.

Filipowicz, W., and Shatkin, A. J. (1983). Origin of splice junction phosphate in tRNAs processed by HeLa cell extract. Cell 32, 547-557.

Galperin, M. Y., and Koonin, E. V. (2004). 'Conserved hypothetical' proteins: prioritization of targets for experimental study. Nucleic acids research 32, 5452-5463.

Genschik, P., Drabikowski, K., and Filipowicz, W. (1998). Characterization of the Escherichia coli RNA 3'-terminal phosphate cyclase and its sigma54-regulated operon. The Journal of biological chemistry 273, 25516-25526.

Laski, F. A., Fire, A. Z., RajBhandary, U. L., and Sharp, P. A. (1983). Characterization of tRNA precursor splicing in mammalian extracts. The Journal of biological chemistry 258, 11974-11980.

Okada, C., Maegawa, Y., Yao, M., and Tanaka, I. (2006). Crystal structure of an RtcB homolog protein (PH1602-extein protein) from Pyrococcus horikoshii reveals a novel fold. Proteins 63, 1119-1122.

Reid CE, Lazinski DW (2000) A host-specific function is required for ligation of a wide variety of ribozyme-processed RNAs. *Proc Natl Acad Sci USA* 97(1): 424-429

The invention claimed is:

1. A method of ligating two RNA molecule ends comprising contacting a HSPC117 molecule with a first RNA molecule end and a second RNA molecule end, and ligating the first RNA molecule end to the second RNA molecule end by using the HSPC117 molecule as an RNA ligase;
   wherein the RNA molecule having the first RNA molecule end is labelled with a label; and/or wherein the HSPC117 molecule comprises an additional polypeptide sequence.

2. The method of claim 1, wherein the HSPC117 molecule is used for inter- or intra-strand ligation.

3. The method of claim 1, wherein the RNA is double-stranded.

4. The method of claim 1, wherein the HSPC117 molecule is used for RNA splicing.

5. The method of claim 1, wherein the RNA is a mRNA or tRNA.

6. The method of claim 1, wherein the RNA molecule having the first RNA molecule end and/or the RNA molecule having the second RNA molecule end is 2 to 3000 nucleotides or basepairs in length.

7. The method of claim 1, wherein the HSPC117 molecule comprises any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 13, SEQ ID NO: 15, SEQ ID NO: 17, SEQ ID NO: 19, SEQ ID NO: 21, SEQ ID NO: 23.

8. The method of claim 1, wherein the contacting is in vitro.

9. The method of claim 1, wherein the HSPC117 molecule is provided in a complex.

10. The method of claim 1, wherein the label is a radiolabel and/or the additional polypeptide sequence is a c-myc tag.

11. The method of claim 1, wherein the first RNA molecule end comprises a 3' phosphate and/or a 2',3'-cyclic phosphate.

12. The method of claim 1 wherein the second RNA molecule end comprises an 5'-OH terminus.

13. A method of ligating two RNA molecule ends comprising
   expressing a HSPC117 molecule wherein the HSPC117 molecule comprises an additional polypeptide sequence,
   contacting the HSPC117 molecule with a first RNA molecule end and a second RNA molecule end, and
   ligating the first RNA molecule end to the second RNA molecule end by using the HSPC117 molecule as an RNA ligase.

14. The method of claim 13, wherein the additional polypeptide sequence is a tag.

15. The method of claim 14, wherein the additional polypeptide sequence is a c-myc tag.

* * * * *